US007550424B2

(12) United States Patent
Supuran et al.

(10) Patent No.: US 7,550,424 B2
(45) Date of Patent: *Jun. 23, 2009

(54) CA IX-SPECIFIC INHIBITORS

(75) Inventors: Claudiu Supuran, Florence (IT);
Andrea Scozzafava, Florence (IT);
Silvia Pastorekova, Bratislava (SK);
Jaromir Pastorek, Bratislava (SK)

(73) Assignee: Institute of Virology Slovak Academy of Sciences, Bratislava (SK)

(*) Notice: Subject to any disclaimer, the term of this patent is extended or adjusted under 35 U.S.C. 154(b) by 893 days.

This patent is subject to a terminal disclaimer.

(21) Appl. No.: 10/723,795

(22) Filed: Nov. 26, 2003

(65) Prior Publication Data

US 2004/0146955 A1 Jul. 29, 2004

Related U.S. Application Data

(60) Provisional application No. 60/429,089, filed on Nov. 26, 2002, provisional application No. 60/489,473, filed on Jul. 22, 2003, provisional application No. 60/515,104, filed on Oct. 28, 2003.

(51) Int. Cl.
*A01N 37/18* (2006.01)
*C12Q 1/00* (2006.01)
(52) U.S. Cl. ............................................. 514/2; 435/4
(58) Field of Classification Search ............... 514/2; 435/4
See application file for complete search history.

(56) References Cited

U.S. PATENT DOCUMENTS 6,027,887 A * 2/2000 Zavada et al. .................. 435/6
6,034,099 A 3/2000 Pamukcu et al. ............. 514/310

OTHER PUBLICATIONS

Sigma® Product Information for Fluoresceine Isothiocynate (Dec. 2000).*
Loncaster et al. (Cancer Research 2001; 61: 6394-6399).*
Parkkila et al. (PNAS 2000; 97: 2220-2224).*
Parkkila et al. (Histochemical Journal 1995; 27: 974-982).*
Supuran et al. (Expert Opinion on Therapeutic Patents 2000; 10: 575-600).*
Supuran et al. (Curr. Med. Chem.-Imm., Endoc. & Metab. Agents 2001; 1: 61-97).*
Casini et al., "Carbonic Anhydrase Inhibitors: Water-Soluble 4-Sulfamoylphenylthioureas as Topical Intraocular Pressure-Lowering Agents with Long-Lasting Effects," *J. Med. Chem.*, 43: 4884-4892 (2000).
Chegwidden et al., "The Roles of Carbonic Anhydrase Isozymes in Cancer," *Gene Families: Studies of DNA, RNA, Enzymes and Proteins*, Proceedings of the International Isozymes, 10th, Beijing, China, Oct. 5-10, 1999, Meeting Date 1999, 157-169 (Xue, G. ed.; World Scientific Pub. Co.; 2001).
Clare and Supuran, "Carbonic anhydrase iinhibitors. Part 61. Quantum chemical QSAR of a group of benzenedisulfonamides," *Eur. J. Med. Chem.*, 34: 463-474 (1999).
Cuthbert et al., "Bicarbonate-dependent chloride secretion in Calu-3 epithelia in response to 7,8-benzoquinoline," *J Physiol.*, 551 (Pt 1): 79-92 (Aug. 15, 2003).
Franchi et al., "Carbonic Anhydrase Inhibitors. Inhibition of Cytosolic Isozymes I and II and Transmembrane, Cancer-associated Isozyme IX with Lipophilic Sulfonamides," *Journal of Enzyme Inhibition and Medicinal Chemistry*, 18(4): 333-338 (Aug. 2003).
Ilies et al., "Carbonic Anhydrase Inhibitors. Inhibition of Tumor-Associated Isozyme IX by Halogenosulfanilamide and Halogenophenylaminobenzolamide Derivatives," *J. Med. Chem.*, 46: 2187-2196 (2003).
Pastorek et al., "Cloning and characterization of MN, a human tumor-associated protein with a domain homologous to carbonic anhydrase and a putative helix-loop-helix DNA binding segment," *Oncogene*, 9: 2877-2888 (1994).

(Continued)

*Primary Examiner*—Brandon J Fetterolf
(74) *Attorney, Agent, or Firm*—Leona L. Lauder; Joan C. Harland; Barbara A. Shimei

(57) ABSTRACT

Therapeutic methods for inhibiting the growth of preneoplastic/neoplastic vertebrate cells that abnormally express MN protein are disclosed. Screening assays are provided for identifying compounds, preferably membrane-impermeant compounds, which inhibit the enzymatic activity of MN protein/polypeptides and that are useful for treating patients with preneoplastic/neoplastic disease. Further methods are disclosed for the preparation of positively-charged, membrane-impermeant heterocyclic sulfonamide CA inhibitors with high affinity for the membrane-bound carbonic anhydrase CA IX. Preferred CA IX-specific inhibitors are aromatic and heterocylic sulfonamides, preferably that are membrane-impermeant. Particularly preferred CA IX-specific inhibitors are pyridinium derivatives of such aromatic and heterocyclic sulfonamides. The CA IX-specific inhibitors of the invention can also be used diagnostically/prognostically for preneoplastic/neoplastic disease, and for imaging use, for example, to detect precancerous cells, tumors and/or metastases. The CA IX-specific inhibitors can be labelled or conjugated to radioisotopes for radiotherapy. The CA IX-specific inhibitors may be combined with conventional therapeutic anti-cancer drugs, with other different inhibitors of cancer-related pathways, with bioreductive drugs, or with radiotherapy to enhance the efficiency of each treatment. The CA IX-specific inhibitors may also be combined with CA IX-specific antibodies, preferably monoclonal antibodies or biologically active antibody fragments, more preferably humanized or fully human CA IX monoclonal antibodies or biologically active fragments or such monoclonal antibodies. Still further, the CA IX-specific inhibitors can be used for gene therapy coupled to vectors for targeted delivery to preneoplastic/neoplastic cells expressing CA IX on their surfaces.

19 Claims, 13 Drawing Sheets

OTHER PUBLICATIONS

Scozzafava and Supuran, "Carbonic Anhydrase Inhibitors: Synthesis of N-Morpholylthiocarbonylsulfenylamino Aromatic/Heterocyclic Sulfonamides and their Interaction with Isozymes I, II and IV," *Bioorganic & Medicinal Chemistry Letters*, 10: 1117-1120 (2000).

Scozzafava et al., "Carbonic Anhydrase Inhibitors. Synthesis of Water-Soluble, Topically Effective, Intraocular Pressure-Lowering Aromatic/Heterocyclic Sulfonamides Containing Cationic or Anionic Moieties: Is the Tail More Important than the Ring?" *J. Med. Chem.*, 42: 2641-2650 (1999).

Scozzafava et al., "Carbonic Anhydrase Inhibitors: Synthesis of Membrane-Impermeant Low Molecular Weight Sulfonamides Possessing in Vivo Selectivity for the Membrane-Bound versus Cytosolic Isozymes," *J. Med. Chem.*, 43: 292-300 (Jan. 27, 2000).

Sterling et al., "The functional and physical relationship between the DRA bicarbonate transporter and carbonic anhydrase II," *Am. J. Physiol. Cell Physiol.*, 283(5): C1522-C1529 (Nov. 2002).

Supuran and Clare, "Carbonic anhydrase inhibitors. Part 24. A quantitative structure-activity relationship study of positively charged sulfonamide inhibitors," *Eur. J. Med. Chem.*, 30: 687-696 (1995).

Supuran and Clare, "Carbonic anhydrase inhibitors—Part 57: Quantum chemical QSAR of a group of 1,3,4-thiadiazole- and 1,3,4-thiadiazoline disulfonamides with carbonic anhydrase inhibitory properties," *Eur. J. Med. Chem.*, 34: 41-50 (1999).

Supuran and Scozzafava, "Carbonic Anhydrase Inhibitors: Aromatic Sulfonamides and Disulfonamides Act as Efficient Tumor Growth Inhibitors," *J. Enzyme Inhib.*, 15(6): 597-610 (2000).

Supuran and Scozzafava, "Carbonic anhydrase inhibitors—Part 94. 1,3,4-Thiadiazole-2-sulfonamide derivatives as antitumor agents?," *Eur. J. Med. Chem.*, 35(9):867-874 (Sep. 2000).

Supuran et al., "Carbonic anhydrase inhibitors—Part 53. Synthesis of substituted-pyridinium derivatives of aromatic sulfonamides: The first non-polymeric membrane-impermeable inhibitors with selectivity for isozyme IV," *Eur. J. Med. Chem.*, 33: 577-594 (1998).

Supuran et al., "Carbonic anhydrase inhibitors—Part 29: Interaction of isozymes I, II and IV with benzolamide-like derivatives," *Eur. J. Med. Chem.*, 33: 739-751 (1998).

Supuran et al., "Carbonic Anhydrase Inhibitors: Synthesis of Sulfonamides Incorporating 2,4,6-Trisubstituted-Pyridinium-Ethylcarboxamido Moieties Possessing Membrane-Impermeability and In Vivo Selectivity for the Membrane-Bound (CA IV) Versus the Cytosolic (CA I and CA II) Isozymes," *J. Enzyme Inhibition*, 15(4): 381-401 (2000).

Supuran et al., "Carbonic Anhydrase Inhibitors: Sulfonamides as Antitumor Agents?," *Bioorganic& Medicinal Chemistry*, 9(3): 703-714 (Mar. 2001).

Supuran et al., "Carbonic Anhydrase Inhibitors," *Medicinal Research Reviews*, 23(2): 146-189 (Mar. 2003).

Teicher et al., "A Carbonic Anhydrase Inhibitor as a Potential Modulator of Cancer Therapies," *Anticancer Research*, 13: 1549-1556 (1993).

Vullo et al., "Carbonic Anhydrase Inhibitors. Inhibition of Cytosolic Isozymes I and II and Transmembrane, Cancer-associated Isozyme IX with Anions," *Journal of Enzyme Inhibition and Medicinal Chemistry*, 18(5): 403-406 (Oct. 2003).

Vullo et al., "Carbonic Anhydrase Inhibitors: Inhibition of the Tumor-Associated Isozyme IX with Aromatic and Heterocyclic Sulfonamides," *Bioorganic Medicinal Chemistry Letters*, 13(6): 1005-1009 (Mar. 24, 2003).

Wingo et al., "The Catalytic Properties of Human Carbonic Anhydrase IX," *Biochemical and Biophysical Research Communications*, 288: 666-669 (2001).

Anderson et al., "The Process of Structure-Based drug Design," *Chemistry & Biology*, 10: 787-797 (Sep. 2003).

Knight et al., "Features of Selective Kinase Inhibitors," *Chemistry & Biology*, 12: 621-631 (Jun. 2005).

Riendeau et al., "Etoricoxib (MK-0663): Preclinical Profile and Comparison with Other Agents That Selectively Inhibit Cyclooxygenase-2," *The Journal of Pharmacology and Experimental Therapeutics*, 296(2): 558-566 (2001).

Alterio et al., "Carbonic Anhydrase Inhibitors: X-ray and Molecular Modeling Study for the Interaction of a Fluorescent Antitumor Sulfonamide with Isozyme II and IX," *J. Am. Chem. Soc.*, 128: 8329-8335 (2006).

Cecchi et al., "Carbonic Anhydrase Inhibitors. Design of Fluorescent Sulfonamides as Probes of Tumor-Associated Carbonic Anhydrase IX that Inhibit Isozyme IX-Mediated Acidification of Hypoxic Tumors," *J. Med. Chem.*, 48: 4834-4841 (2005).

Robertson et al., "Role of Carbonic Anhydrase IX in Human Tumor Cell Growth, Survival, and Invasion," *Cancer Research*, 64: 6160-6165 (Sep. 1, 2004).

Svastova et al., "Hypoxia Activates the Capacity of Tumor-Associated Carbonic Anhydrase IX to Acidify Extracellular pH," *FEBS Letters*, 577: 439-445 (2004).

Gruneberg et al., "Successful virtual screening for novel inhibitors of human carbonic anhydrase: strategy and experimental confirmation," *J. Med. Chem.*, 45(17): 3588-3602 (Abstract) (Aug. 15, 2002).

Liu et al., "BindingDB: a web-accessible database of experimentally determined protein-ligand binding affinities," *Nucleic Acids Research*, 00 (Database issue): D1-D4 (Dec. 1, 2006).

Taylor et al., "Ligand discovery and virtual screening using the program Lidaeus," *British Journal of Pharmacology*, 153: 555-567 (2008).

Winum et al., "Carbonic Anhydrase Inhibitors. Inhibition of Cytosolic Isozymes I and II and Transmembrane, Tumor-Associated Isozyme Ix with Sulfamates Including Emate Also Acting as Steroid Sulfatase Inhibitors," *J. Med. Chem.*, 46(11): 2197-2204 (May 22, 2003).

Wistrand and Lindqvist, "Design of Carbonic Anhydrase Inhibitors and the Relationship Between the Pharmacodynamics and Pharmacokinetics of Acetazolamide," *In Carbonic Anhydrase—From Biochemistry and Genetics to Physiology and Clinical Medicine*, Botré et al., Eds., VCH, Weinheim, pp. 352-378 (1991).

Wu et al., Cytoplasmic pH Responses to Carbonic Anhydrase Inhibitors in Cultured Rabbit Nonpigmented Ciliary Epithelium, *J. Membrane Biol.*, 162: 31-38 (1998).

* cited by examiner

| | | | | | | | | | | | | |
|---|---|---|---|---|---|---|---|---|---|---|---|---|
| 1<br>1 | ACA | GTC | AGC | CGC | M<br>ATG | A<br>GCT | P<br>CCC | L<br>CTG | C<br>TGC | P<br>CCC | S<br>AGC | P<br>CCC | W<br>TGG | L<br>CTC | P<br>CCT | L<br>CTG | 12<br>48 |
| 13<br>49 | L<br>TTG | I<br>ATC | P<br>CCG | A<br>GCC | P<br>CCT | A<br>GCT | P<br>CCA | G<br>GGC | L<br>CTC | T<br>ACT | V<br>GTG | Q<br>CAA | L<br>CTG | L<br>CTG | S<br>TCA | 28<br>96 |
| 29<br>97 | L<br>CTG | L<br>CTG | L<br>CTT | M<br>CTG | L<br>ATG | M<br>ATG | P<br>CCT | V<br>GTC | H<br>CAT | P<br>CCC | Q<br>CAG | R<br>AGG | L<br>TTG | P<br>CCC | R<br>CGG | M<br>ATG | Q<br>CAG | 44<br>144 |
| 45<br>145 | E<br>GAG | D<br>GAT | S<br>TCC | P<br>CCC | L<br>TTG | G<br>GGA | G<br>GGA | V<br>GTC | P<br>CCT | H<br>CAT | Q<br>CAG | S<br>TCT | S<br>TCT | G<br>GGG | E<br>GAA | L<br>TTG | D<br>GAC | P<br>CCA | 60<br>192 |
| 61<br>193 | G<br>GGA | E<br>GAG | E<br>GAG | D<br>GAT | L<br>CTG | P<br>CCC | S<br>AGT | E<br>GAA | E<br>GAG | D<br>GAT | S<br>TCA | G<br>GGG | E<br>GAG | E<br>GAG | E<br>GAG | E<br>GAG | D<br>GAT | 76<br>240 |
| 77<br>241 | P<br>CCA | P<br>CCC | G<br>GGA | E<br>GAG | E<br>GAG | D<br>GAT | L<br>CTA | P<br>CCT | G<br>GGA | E<br>GAG | E<br>GAG | E<br>GAG | S<br>TCA | K<br>AAA | G<br>GGA | P<br>CCT | E<br>GAG | 92<br>288 |
| 93<br>289 | E<br>GAG | D<br>GAT | L<br>CTA | P<br>CCT | E<br>GAA | V<br>GTT | K<br>AAG | P<br>CCT | T<br>ACT | V<br>GTT | E<br>GAG | S<br>TCA | A<br>GCT | E<br>GAG | E<br>GAG | G<br>GGC | S<br>TCC | L<br>CTG | 108<br>336 |
| 109<br>337 | K<br>AAG | L<br>TTA | E<br>GAG | D<br>GAT | L<br>CTA | P<br>CCT | T<br>ACT | V<br>GTT | E<br>GAG | A<br>GCT | P<br>CCT | G<br>GGA | D<br>GAT | P<br>CCT | Q<br>CAA | E<br>GAA | 124<br>384 |
| 125<br>385 | P<br>CCC | Q<br>CAG | N<br>AAT | N<br>AAT | A<br>GCC | H<br>CAC | R<br>AGG | D<br>GAC | K<br>AAA | E<br>GAA | G<br>GGG | D<br>GAT | D<br>GAC | D<br>GAC | Q<br>CAG | S<br>AGT | H<br>CAT | 140<br>432 |
| 141<br>433 | W<br>TGG | R<br>CGC | Y<br>TAT | G<br>GGC | G<br>GGA | D<br>GAC | P<br>CCG | P<br>CCC | W<br>TGG | P<br>CCC | R<br>CGG | V<br>GTG | S<br>TCC | P<br>CCA | A<br>GCC | C<br>TGC | 156<br>480 |
| 157<br>481 | A<br>GCG | G<br>GGC | R<br>CGC | F<br>TTC | Q<br>CAG | S<br>TCC | P<br>CCG | V<br>GTG | D<br>GAT | I<br>ATC | R<br>CGC | P<br>CCC | Q<br>CAG | L<br>CTC | A<br>GCC | A<br>GCC | 172<br>528 |

*FIG._1A*

| Pos | | | | | | | | | | | | | | | | | | End |
|---|---|---|---|---|---|---|---|---|---|---|---|---|---|---|---|---|---|---|
| 173 | F | C | P | A | L | R | P | L | E | L | L | G | F | Q | L | P | | 188 |
| 529 | TTC | TGC | CCG | GCC | CTG | CGC | CCC | CTG | GAA | CTC | CTG | GGC | TTC | CAG | CTC | CCG | | 576 |
| 189 | P | L | P | E | L | R | L | R | N | N | G | H | S | V | Q | L | | 204 |
| 577 | CCG | CTC | CCA | GAA | CTG | CGC | CTG | CGC | AAT | AAC | GGC | CAC | AGT | GTG | CAA | CTG | | 624 |
| 205 | T | L | P | G | L | H | L | Q | M | A | E | L | L | H | L | L | | 220 |
| 625 | ACC | CTG | CCT | GGG | CTA | CAT | CTG | CAG | ATG | GCT | GAG | CTG | CTG | CAC | CTC | TAC | | 672 |
| 221 | R | A | L | Q | T | V | H | L | H | R | F | P | A | A | G | Y | | 236 |
| 673 | CGG | GCT | CTG | CAG | ACT | GTG | CAT | CTG | CAC | CGT | TTC | CCT | GCA | GCA | GGT | TAC | | 720 |
| 237 | S | E | H | T | V | E | G | H | R | F | P | A | E | I | H | V | | 252 |
| 721 | TCG | GAG | CAC | ACT | GTG | GAA | GGC | CAC | CGT | TTC | CCT | GCC | GAG | ATC | CAC | GTG | | 768 |
| 253 | V | H | L | S | T | A | F | A | R | V | D | E | A | L | G | R | | 268 |
| 769 | GTT | CAC | CTC | AGC | ACC | GCC | TTT | GCC | AGA | GTT | GAC | GAG | GCC | TTG | GGG | CGC | | 816 |
| 269 | P | G | G | L | A | V | F | A | A | F | L | E | G | E | P | E | | 284 |
| 817 | CCG | GGA | GGC | CTG | GCC | GTG | TTT | GCC | GCC | TTT | CTG | GAG | GGC | GAG | CCG | GAA | | 864 |
| 285 | E | N | S | A | Y | E | Q | L | L | S | R | L | E | E | I | A | | 300 |
| 865 | GAA | AAC | AGT | GCC | TAT | GAG | CAG | CTG | TTG | TCT | CGC | TTG | GAA | GAA | ATC | GCT | | 912 |
| 301 | E | G | S | E | T | Q | L | V | P | G | L | D | Y | E | A | L | | 316 |
| 913 | GAG | GGC | TCA | GAG | ACT | CAG | CTG | GTC | CCA | GGA | CTG | GAC | TAT | GAG | GCA | CTC | | 960 |
| 317 | L | P | S | D | F | R | Y | Q | F | Y | E | G | S | L | T | L | | 332 |
| 961 | CTG | CCC | TCT | GAC | TTC | CGC | TAC | CAA | TTC | TAT | GAG | GGG | TCT | CTG | ACT | ACT | | 1008 |
| 333 | T | P | C | A | Q | G | V | I | W | T | V | F | N | Q | T | T | | 348 |
| 1009 | ACA | CCG | CCC | TGT | GCC | CAG | GGT | GTC | ATC | TGG | ACT | GTG | TTT | AAC | CAG | ACA | | 1056 |

FIG._1B

| | | | | | | | | | | | | | | | | |
|---|---|---|---|---|---|---|---|---|---|---|---|---|---|---|---|---|
| 349 | V | M | L | S | A | K | Q | L | H | T | L | S | D | T | L | W | 364 |
| 1057 | GTG | ATG | CTG | AGT | GCT | AAG | CAG | CTC | CAC | ACC | CTC | TCT | GAC | ACC | CTG | TGG | 1104 |
| 365 | G | P | G | D | S | R | L | Q | N | F | S | R | A | T | Q | P | 380 |
| 1105 | GGA | CCT | GGT | GAC | TCT | CGG | CTA | CAG | AAC | TTC | TCC | CGA | GCG | ACG | CAG | CCT | 1152 |
| 381 | L | N | G | R | V | I | E | A | P | V | G | D | S | 396 |
| 1153 | TTG | AAT | GGG | CGA | GTG | ATT | GAG | GCC | CCT | GTG | GGA | GAC | AGC | 1200 |
| 397 | S | P | R | A | A | Q | L | N | S | C | L | A | A | 412 |
| 1201 | AGT | CCT | CGG | GCT | GCT | CAG | CTG | AAT | TCC | TGC | CTG | GCT | GCT | 1248 |
| 413 | G | D | I | L | A | V | F | G | L | F | A | V | S | 428 |
| 1249 | GGT | GAC | ATC | CTA | GCC | GTT | TTT | GGC | CTC | TTT | GCT | GTC | AGC | 1296 |
| 429 | V | A | F | L | V | Q | M | R | R | H | R | Q | T | K | 444 |
| 1297 | GTC | GCG | TTC | CTT | GTG | CAG | ATG | AGA | AGG | CAC | AGA | CAG | ACC | AAA | 1344 |
| 445 | G | G | V | S | Y | R | P | A | E | V | A | E | T | G | A | * | 460 |
| 1345 | GGG | GGT | GTG | AGC | TAC | CGC | CCA | GCA | GAG | GTA | GCC | GAG | ACT | GGA | GCC | TAG | 1392 |
| 1393 | AGG | CTG | GAT | CTT | GGA | GAA | TGT | CCT | GTC | CTG | CTC | AGA | GGC | ATC | TGA | GGG | 1440 |
| 1441 | GGA | GCC | GGT | AAC | TGT | TAA | AAT | AAA | TAT | TTA | TAA | CCA | GCC | AGA | CCT | TTT | 1488 |
| 1489 | TGC | CAA | GAA | ATT | TTT | TAA | AAT | AAA | TAT | TTA | TAA | T | | | | | 1522 |

```
   1 ggatccctgtt gactcgtgac cttaccccca accctgtgct cttctgaaaca tgagctgtgt
  61 ccactcaggg ttaaatggat taaggcggt gcaagatgtg ctttgttaaa cagatgcttg
 121 aaggcagcat gctcgttaag agtcatcacc aatcctaat ctcaagtaat caggacaca
 181 aacactgcgg aaggccgcag ggtcctctgc ctaggaaaac cagagacctt tgttcacttg
 241 tttatctgac cttccctcca ctattgtcca tgaccctgcc aaatccccct ctgtgagaaa
 301 cacccaagaa ttatcaataa aaaaataaat ttaaaaaaaa aatacaaaaa aaaaaaaaaa
 361 aaaaaaaaaa gacttacgaa tagttattga taaatgaata gctattggta aagccaagta
 421 aatgatcata ttcaaaacca gacggccatc atcacagctc aagtctacct gattgatct
 481 ctttatcatt gtcattcttt ggattcacta gattagtcat catcctcaaa attctcccc
 541 aagttctaat tacgttccaa acatttaggg gttacatgaa gcttgaacct actacctct
 601 ttgcttttga gccatgagtt gtaggaatga tgagtttaca ccttacatgc tggggattaa
 661 tttaaacttt acctctaagt cagtgggta gcctttgct tattttgta gctaattttg
 721 tagttaatgg atgcactgtg aatcttgcta tgatagtttt cctccacact ttgccactag
 781 gggtaggtag gtactcagtt ttcagtaatt gcttacctaa gaccctaagc cctattctc
 841 ttgtactggc ctttatctgt aatatgggca tatttaatac aatataattt ttggagtttt
 901 tttgtttgtt tgtttgtttg ttttttttgag acggagtctt acgagctcct gcatctgtca tcacgccagct
 961 ggagtagcag tggtgccatc tcggctcact gcaagctcca cctcccgagt cctgccatt
1021 ttcctgcctc agcctcccga gtagctggga ctacaggcgc ccgccaccat gcccggctaa
1081 ttttttgtat tttgtagta gacggggttt caccgtgtta gccagaatgg tctcgatctc
1141 ctgacttcgt gatccaccg cctcggcctc ccaaagttct ggcttttcct ttgacagcct gtgactgcgg
1201 ccgcacctgg ccaatttttt gagtctttta aagtaaaaat atgtccttgta agctggtaac
1261 tatggtacat ttccttttat taatgtggtg ctgacggtca tataggttct tttgagtttg
1321 gcatgcatat gctactttt gcagtccttt cattacattt ttctctcttc atttgaagag
1381 catgttatat ctttagctt cacttggctt aaaaggttct ccattagcc taacacagtg
1441 tcattgttgg taccacttgg atcataagtg gaaaaacagt caagaaattg cacagtaata
1501 cttgtttgta agagggatga ttcaggtgaa tctgacacta agaaactccc ctacctgagg
1561 tctgagattc ctctgacatt gctgtatata ggcttttcct ttgacagcct gtgactgcgg
1621 actatttttc ttaagcaaga tatgctaaag ttttgtgagc cttttttccag agagaggtct
1681 catatctgca tcaagtgaga acatataatg tctgcatgtt tccatatttc aggaatgttt
1741 gcttgtgttt tatgtcttta tatagacagg gaaacttgtt cctcagtgac ccaaaagagg
1801 tgggaattgt tattgatat catcattgc ccacgctttc tgaccttgga aacaattaag
1861 ggttcataat ctcaattctg tcagaattgg tacaagaaat agctgctatg tttcttgaca
1921 ttccacttgg taggaaataa gaatgtgaaa ctcttcagtt ggtgtgtgtc cct?gtttt
```

```
1981 ttgcaatttc cttcttactg tgttaaaaaa aagtatgatc ttgctctgag aggtgaggca
2041 ttcttaatca tgatctttaa agatcaataa tataatcctt tcaaggatta tgtctttatt
2101 ataataaaga taatttgtct ttaacagaat caataatata atcccttaaa ggattatatc
2161 tttgctgggc gcagtggctc acacctgtaa tcccagcact ttgggtggcc aagtggaag
2221 gatcaaattt gcctacttct atattatctt ctaaagcaga attcatctct cttccctcaa
2281 tatgatgata ttgacagggt ttgccctcac tcactagatt gtgagctcct gctcagggca
2341 ggtagcgttt tttgttttg agtgcaatgg tttttttga tctttttga gacagggtct tgtctgtca
2401 cccaggccag ccatcatcagc tacagtctca gctcactgca gcctcaaccg cctcggctca
2461 aaccatcatc ccatttcagc ctcctgagta gctggacta caggcacatg ccattacacc
2521 tggctaattt tttgtattt ctagtagaga caggtttgg ccatgttgcc cgggctggtc
2581 tcgaactcct ggactcaagc aatccaccca cctcagcctc ccaaaatgag ggaccgtgtc
2641 ttattcattt ccatgtccct agtccatagc ccagtgctgg acctatgta gtactaaata
2701 aatatttgtt gaatgcaata gtaaatagca tttcaggag caagaactag attaacaaag
2761 gtgtaaaag gtttggagaa aaaaataata gttaatttg gctagagtat gagggagagt
2821 agtaggagac aagatggaaa ggtctcttgg gcaaggtttt gaaggaagtt ggaagtcaga
2881 agtacacaat gtgcatatcg tggcaggcag tgggagcca atgaaggctt ttgagcagga
2941 gagtaatgtg ttgaaaaata aatataggtt aaacctatca gagcccctct gacacataca
3001 cttgcttttc attcaagctc aagtttgtct cccacatacc cattacttaa ctcacctcg
3061 ggctcccta gcagcctgcc ctacctcttt acctgcttcc tggtggagtc aggatgtat
3121 acatgagctg ctttccctct cagccagagg acatgggga cccagctcc ctgcctttc
3181 cccttctgtg cctggagctg ggaagcaggc caggttagc tgaggctggc tggcaagcag
3241 ctgggtggtg ccaggagag cctgcatagt gccagtggt gccttgggtt ccaagctagt
3301 ccatgcccc gataaccttc tgcctgtgca cacacctgcc cctcactcca ccccatcct
3361 agctttggta tggggagag ggcacagggc cagacaaacc tgtgagactt tggctccatc
3421 tctgcaaag ggcgtctgt gagtcagcct gctcccctcc aggcttgctc ctccccacc
3481 cagctctcgt ttccaatgca cgtacagccc gtacacaccg tgtgctggga caccACAG
3541 TCAGCCGCAT GGCTCCCCTG TGCCCCAGCC CCTGGCTCTC CACTGCTGCT TCTGTTGATC CCGGCCCCTG
3601 CTCCAGGCCT CACTGTGCAA CTGCTGCTGT CTTGGGAGG AGGCTCTTCT GTCCATCCCC
3661 AGAGGTTGCC CCGGATGCAA GGAGATTCCC CCTTGGGAGG AGGCTCTTCT GGGAAGATG
3721 ACCCACTGGG CGAGGAGGAT CTGCCCAGTG AAGAGGATTC ACCCAGAGAG GAGGATCCAC
3781 CCGGAGAGGA GGATCTACCT GGAGAGGAGG ATCTACCTGG AGAGGAGGAT CTACCTGAAG
3841 TTAAGCCTAA ATCAGAAGAA GAGGGCTCCC TGAAGTTAGA GGATCTACCT ACTGTTGAGG
3901 CTCCTGGAGA TCCTCAAGAA CCCCAGAATA ATGCCCACAG GGACAAAGAA Ggtaagtggt
```

FIG. _2B

```
3961 catcaatctc caaatccagg ttccaggagg ttcatgactc ccctcccata cccagccta
4021 ggctctgttc actcagggaa ggagggaga ctgtactccc cacagaagcc cttccagagg
4081 tcccatacca atatcccat cccactctc ggaggtagaa agggacagat gtggagagaa
4141 aataaaaagg gtgcaaaagg agagaggtga gctggatgag atgggagaga aggggaggc
4201 tggagagag aaaggatga gaactgcaga tgagggaaaa aatgtgcaga cagagaaaa
4261 aaatagtgg agaaggagag tcagagagtt tgagggaag agaaaaggaa agctttgggag
4321 gtgaagtggg taccagagac aagcaagaag agctggtaga agtcatctca tcttagcta
4381 caatgaggaa ttgagaccta acacagcagg tagagaaacg tggcttcttg
4441 actcccaagc caggaatttg gggaaagggg ttgagacca tacaaggcag aggatgagt
4501 gggagaaga aagaaggag aaagaaaaa tgtgtactc actcatttgg gactcaggac
4561 tgaagtgccc actcactttt tttttttttt ttttttgagac aaactttcac tttgttgcc
4621 caggctggag tgcaatgcg cgatctcggc tcactgcaac ctccacctcc cgggttcaag
4681 tgattctcct gcctcagcct ctagccaagt agctgcgatt acagcatgc gccaccacgc
4741 ccggctaatt tttgtatttt tagtagagac ggggtttcgc catgttggtc agctggtct
4801 cgaactcctg atctcaggtg atccaaccac ctggcctcc caaagtgctg ggattatagg
4861 cgtgagccac agcgcctggc ctgaagcagc cactcacttt tacagaccct aagacaatga
4921 ttgcaagctg gtaggattgc tgtttggccc accagctgc ggtgttgagt ggtggtgcgg
4981 tctcctgtgc tttgcacctg gcccgcttaa ggcatttgtt accgtaatg ctcctgtaag
5041 gcatctgcgt ttgtgacatc gttttggtcg ccaggaaggg attgggctc taagcttgag
5101 cggttcatcc ttttcattta tacagGGGAT GACCAGAGTC ATTGGCGCTA TGGAGgtgag
5161 acaccaccc gctgcacaga cccaatctgg gaacccagct ctgtgatct ccctacagc
5221 cgtccctgaa cactggtccc gggcgtccca cccgccgccc accgtcccac ccctcacct
5281 tttctacccg ggttcctaa gttcctgacc taggcgtcag acttcctcac tatactctcc
5341 caccccagGC GACCCGCCCT GGCCCCGGGT GTCCCCAGCC TGCGCGGGGCC GCTTCCAGTC
5401 CCCGGTGGAT ATCCGCCCCG AGCTCGCCGC CTTCTGCCCG GCCCTGCGCG CCCTGGAACT
5461 CCTGGGCTTC CAGCTCCCCG CGCTCCCAGA ACTGCGCCTG CGCAACAATG GCCACAGTGg
5521 tgaggggtc tccccgccga gacttgggga tgggcgggg cgcagggaag ggaaccgtcg
5581 cgcagtgcct gccccgggt tgggctgcc ctaccgggcg gggccggctc acttgcctct
5641 ccctacgcag TGCAACTGAC CCTGCCTCCT GGGCTAGAGA TGGCTCTGGG TCCCGGGCGG
5701 GAGTACCGGG CTCTGCAGCT GCATCTGCAC TGGGGGCTG CAGGTCGTCC GGGCTCGGAG
5761 CACACTGTGG AAGGCCACCG GAGtgagcg gtgccctct cctaccctg tgtcctttc
5821 aaagaggcgg ggcggacggg ggcagagac TTTCCCTGCC GAGtgagcg gtgccctct cctaccctg tgtcctttc
5881 agATCCACGT GGTTCACCTC AGCACCGCCT TGACGAGAGT TTGCCAGAGT TGGGGCGCC TTGGGGCGCC
```

FIG._2C

```
5941  CGGGAGGCCT  GGCCGTGTTG  GCCGCCTTTC  TGGAGgtacc  agatcctgga  cacccctac
6001  tcccgcttt   cccatcccat  gctcctccg   gactctatcg  tggagccaga  gacccatcc
6061  cagcaagctc  actcagccc   ctggctgaca  aactcattca  cgcactgttt  gttcatttaa
6121  cacccactgt  gaaccaggca  ccagccccca  acaaggattc  tgaagctgta  ggtcctgcc
6181  tctaaggagc  ccacagccag  tggggaggc   acaagtgaca  gacacatagg  aaggacatag
6241  taaagatggt  ggtcacagag  gaggtgacac  ttaaagcctt  cactggtaga  aagaaaagg
6301  agtgttcat   tgcagaggaa  acagaatgtg  caaagactca  gaatatggcc  tatttaggga
6361  atggctacat  acaccatgat  tagaggagc   ccagtaaagg  gaagggatgg  tgagatgcct
6421  gctaggttca  ctcactcact  tttatttatt  tattttattt  tttgacagtc  tctctgtcgc
6481  ccaggctgga  gtgcagtggt  gtgatcttgg  gtcactgcaa  cttccgcctc  ccggttcaa
6541  gggattctcc  tgcctcagct  tcctgagtag  ctggggttac  agtgtgtgc   caccatgccc
6601  agctaatttt  tttttgtatt  tttagtagac  agggtttcac  catgttggtc  agctgtgtct
6661  caaactcctg  gcctcaagtg  atccgcctga  ctcagcctac  caaagtgctg  attacaagtg
6721  tgagccaccg  tgcccagcca  cactcactga  ttctttaatg  ccagccacac  agcacaaagt
6781  tcagagaaat  gcctccatca  tagcatgtca  atatgttcat  actcttaggt  tcatgatgtt
6841  cttaacatta  ggttcataag  caaaataaga  aaaagaata   atacaatgaaa gaagtggcat
6901  gtcagaacct  cacctgaaaa  gccaaacaca  gaatcatgaa  ggtgaatgca  gaggtgacac
6961  caacacaaag  gtgtatatat  ggtttcctgt  gggagtatg   tacggaggca  gcagtgagtg
7021  agactgcaaa  cgtcagaagg  gcacgggtca  ctgagagcct  agtatcctag  taaagtgggc
7081  tctctccctc  tctctcccagc ttgtcattga  aaaccagtcc  accaagcttg  ttggttcgca
7141  cagcaagagt  acatagagtt  tgaaataata  catagagattt taagagggag  acactgtctc
7201  taaaaaaaa   aacaacagca  acaacaaaaa  gcaacaacca  ttacaatttt  atgttccctc
7261  agcattctca  gagctgagga  atgggagagg  actatgggaa  ccccctcat   gttccggcct
7321  tcagccatgg  ccctggatac  atgcactcat  ctgtcttaca  atgtcattcc  cccagGAGGG
7381  CCCGGAAGAA  AACAGTGCCT  ATGAGCAGTT  GCTGTCTCGC  TTGGAAGAAA  TCGCTGAGGA
7441  AGtcagttt   gttggtctgg  ccactaatct  ctgtggccta  gttcataaag  aatcaccctt
7501  tggagcttca  ggtctgaggc  tggagatggg  ctcccctccag tgcaggaggg  attgaagcat
7561  gagccagcgc  tcatcttgat  aataaccatg  aagctgacag  acacagttac  ccgcaaacgg
7621  ctgcctacag  attgaaaaac  aagcaaaaac  cgccgggcac  ggtggctcac  gcctgtaatc
7681  ccagcactt   gggaggccaa  ggcaggtgga  tcacgaggtc  aagagatcaa  gaccatcctg
7741  gccaacatgg  tgaaacccca  tctctactaa  aaatacgaaa  aaatagccag  gcgtggtggc
7801  gggtgcctgt  aatcccagct  actcgggagg  ctgaggcagg  agaatggcat  gaacccggga
7861  ggcagaagtt  gcagtgagcc  gagatcgtgc  cactgcactc  cagcctgggc  aacagagcga
```

FIG.\_2D

```
7921  gactcttgtc  tcaaaaaaaa  aaaaaaaaa   gaaaaccaag  caaaaaccaa  aatgagacaa
7981  aaaaaacaag  accaaaaaat  ggtgtttgga  aattgtcaag  gtcaagtctg  gagagctaaa
8041  cttttcctga  gaactgttta  tctttaataa  gcatcaaata  tttaacttt   gtaaatactt
8101  ttgttggaaa  tcgttctctt  cttagtcact  cttgggtcat  tttaaatctc  acttactcta
8161  ctagaccttt  taggtttctg  ctagactagg  tagaactctg  cctttgcatt  tcttgtgtct
8221  gttttgtata  gttatcaata  ttcatatttta tttacaagtt attcagatca  ttttttcttt
8281  tcttttttt   tttttttttt  tttttttacat ctttagtaga  gacagggttt  caccatattg
8341  gccaggctgc  tctcaaactc  ctgacctgt   gatccaccag  cctcgcctc   ccaaagtgct
8401  gggattcatt  tttctttt    aatttgctct  gggcttaaac  ttgtgccca   gcactttatg
8461  atggtacaca  gagttaagag  tgtagactca  gacggtcttt  ctccttttcct tctcttcctt
8521  cctccccttcc ctcccacctt  cccttctctc  cttcctttct  ttcttcctct  cttgcttcct
8581  caggcctctc  ccagttgctc  caaagccctg  tacttttttt  tgagttaacg  tcttatggga
8641  agggcctgca  cttagtgaag  aagtggtctc  agagttgagt  tacctttggct tctggaggt
8701  gaaactgtat  ccctatacc   tgaagcttta  aggggggtgca atgtagatga  gaccccaaca
8761  tagatcctct  tcacagGCTC  AGAGACTCAG  GTCCCCAGGAC TGGACATATC  TGCACTCCTG
8821  CCCTCTGACT  TCAGCCGCTA  CTTCCAATAT  GAGGGGTCTC  TGACTACACC  GCCCTGTGCC
8881  CAGGGTGTCA  TCTGGACTGT  GTTTAACCAG  ACAGTGATGC  TGAGTGCTAA  GCAGtgggc
8941  ctgggtgtg   tgtgacaca   gtgggtgcgg  gggaaagagg  atgtaagatg  agatgagaaa
9001  caggagaaga  aagaaatcaa  ggctgggctc  tgtgcttac   gcctataatc  ccaccacgtt
9061  gggaggctga  ggtgggagaa  tggtttgagc  ccaggagttc  aagacaaggc  gggcaacat
9121  agtgtgaccc  catctctacc  aaaaaaaacc  caacaaaaac  aaaaaatagc  gggcatggtg
9181  gtatgcgggcc tagtcccagc  tactcaagga  ggctgaggtg  ggaagatcgc  ttgattccag
9241  gagtttgaga  ctgcagtgag  ctatgatccc  accactgcct  accatcttta  ggatacattt
9301  atttattat   aaaagaaatc  aagaggctgg  atgggaata   caggagctgg  agggtggagc
9361  cctgaggtgc  tggttgtgag  ctgcctgag   acccttgttt  cctgtcatgc  catgaaccca
9421  cccacactgt  ccactgacct  ccctagCTCC  ACACCCTCTC  TGACACCCTG  TGGGGACCTG
9481  GTGACTCTCG  GCTACACAGCTG AACTTCCGAG GTGGACAGCA  CGACGCAGCC  TTTGAATGGG CGAGTGATTG
9541  AGGCCTCCTT  CCCTGCTGGA  GTGGACAGCA  GTCCTCGGGC  TGCTGAGCCA  Ggtacagctt
9601  tgtctggttt  cccccagcc   agtagtccct  tatcctccca  tgtgtgtgcc  agtgtctgtc
9661  attggtgtc   acagcccgcc  tctcacatct  cctttttctc  tccagTCCAG  CTGAATTCCT
9721  GCCTGGCTGC  TGgtgagtct  gccccctcc   ttggtcctga  tgccaggaga  ctcctcagca
9781  ccattcagcc  ccaggctgc   tcagggccgc  tcctgctccc  tctccttttc  tgcagaacag
9841  accccaaccc  caatattaga  gaggcagatc  atggtggggga ttccccccatt gtcccccagag
```

FIG._2E

```
 9901 gctaattgat tagaatgaag cttgagaaat ctcccagcat ccctctcgca aagaatccc
 9961 ccccctttt tttaaagata gggtctcact ctgtttgccc caggctgggg tgttgtggca
10021 cgatcatagc tcactgcagc ctcgaactcc taggctcagg caatccttc accagctt
10081 ctcaaagcac tgggactgta ggcatgagcc actgtgcctg gccccaaacg gccctttac
10141 ttggcttta ggaagcaaaa acggtgctta tcttaccct tctcgtgtat ccacccctcat
10201 cccttggctg gcctcttctg gagactgagg cactatgggg ctgcctgaga actcggggca
10261 gggtggtgg agtgcactga ggcaggtgtt gaggaactct gcagacccct cttccttccc
10321 aaagcagccc tctctgctct ccatcgcagG TGACATCCTA GCCCTGGTTT TTGGCCTCCT
10381 TTTTGCTGTC ACCAGCGTCG CGTTCCTTGT GCAGCAGCACA AGGCAGCACA Gtattacac
10441 tgaccctttc ttcaggcaca agcttcccc acccttgtgg agtcacttca tgcaaagcgc
10501 atgcaaatga gctgctcctg ggccagtttt ctgattagcc tttcctgttg tgtacacaca
10561 gAAGGGGAAC CAAAGGGGT GTGAGCTACC GCCCAGCAGA GGTAGCCGAG ACTGGAGCCT
10621 AGAGGGCTGGA TCTTGGAGAA TGTGAGAAGC CAGCCAGAGG CATCTGAGGG GGAGCCGTA
10681 ACTGTCCCTGT CCTGCTCATT ATGCCACTTC CTTTTAACTG CCAAGAAATT TTTTAAAATA
10741 AATATTATA ATactgttat tgttagtcac ctttgttccc caaatcagaa ggaggtattt
10801 gaatttccta ttactgttat tagcaccaat ttagtggtaa tgcatttatt ctattacagt
10861 tcggccctcct tccacacatc actccaatgt gttgctcc
```

FIG._2F

| FIG._2A |
| FIG._2B |
| FIG._2C |
| FIG._2D |
| FIG._2E |
| FIG._2F |

FIG._2

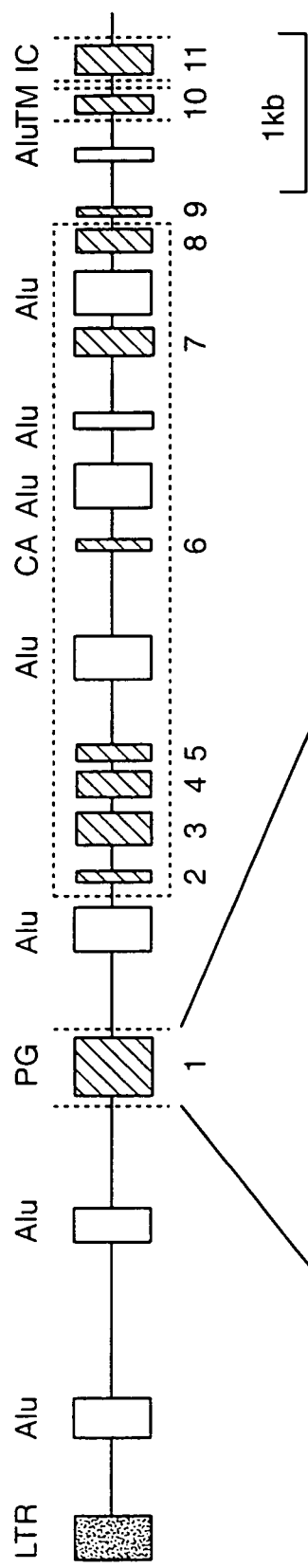
FIG._3

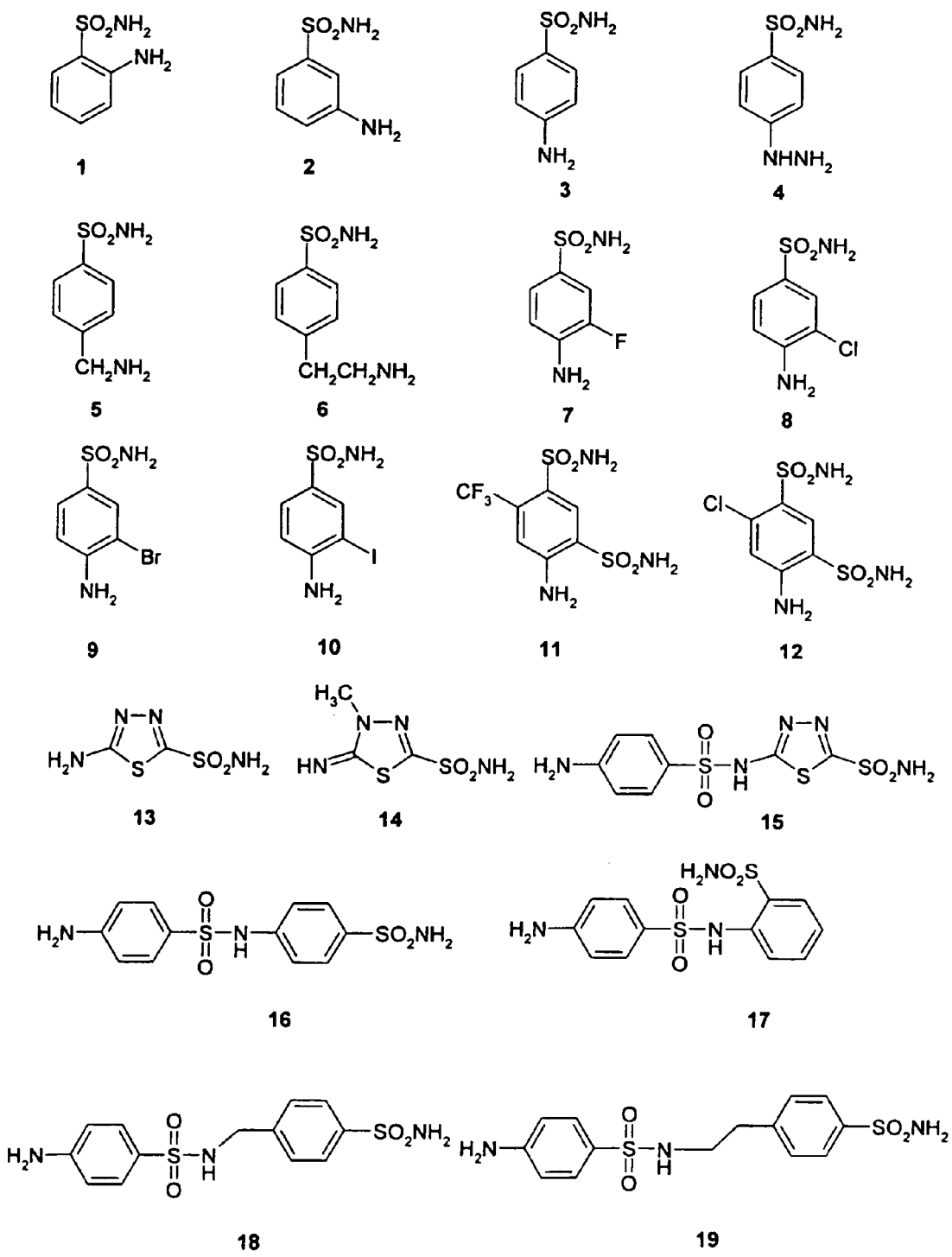
FIG._4A

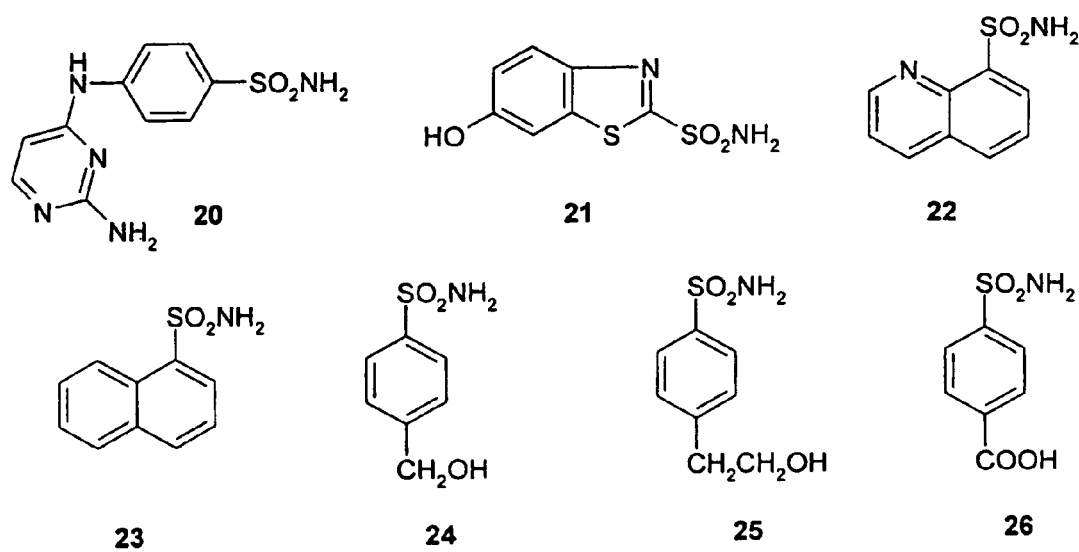
FIG._4B

Scheme 1
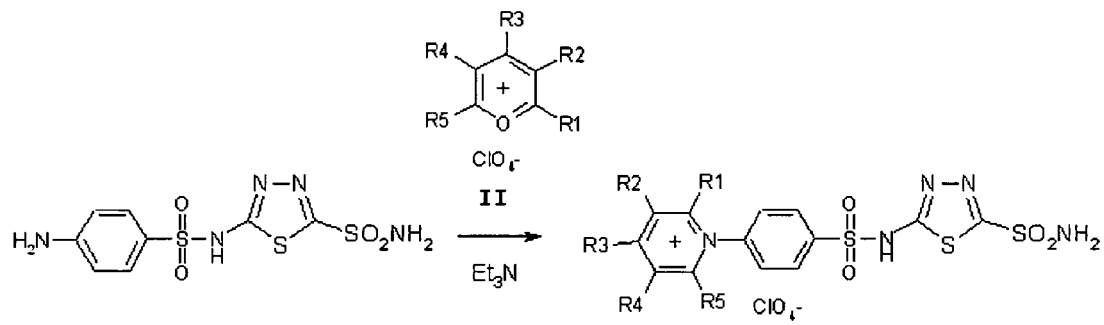
FIG._5
Scheme 2
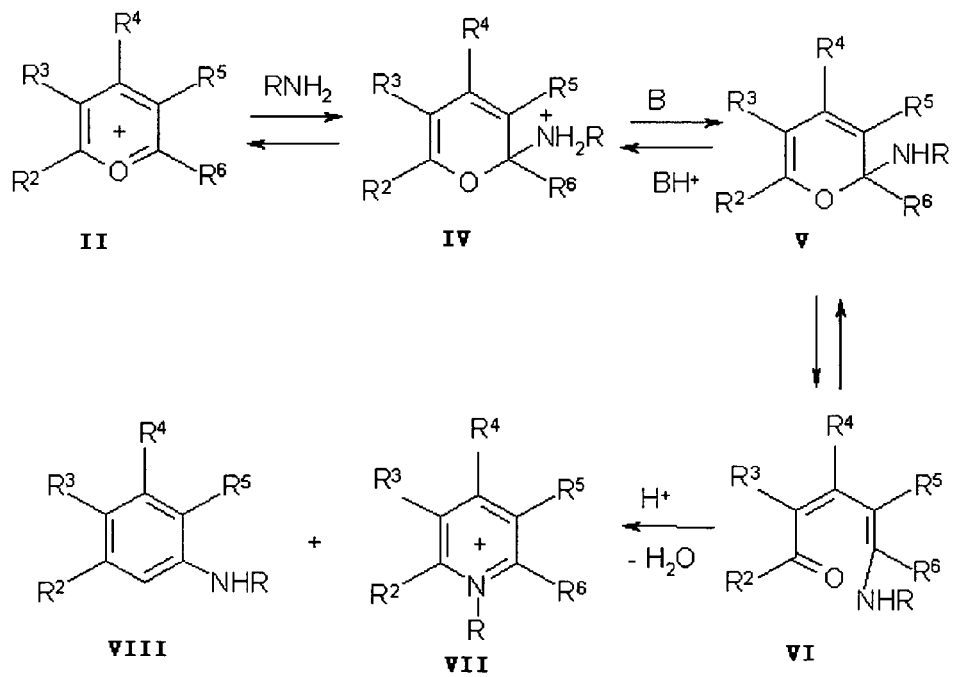
(For R6 or R2 Me)
FIG._6 ized to a remarkable degree. The MN/CA9 gene is assigned to chromosome 17 (17q21.2) and contains 11 exons.

CA IX-SPECIFIC INHIBITORS

This application claims priority from U.S. Provisional Application Nos. 60/429,089 (filed on Nov. 26, 2002), 60/489,473 (filed on Jul. 22, 2003) and 60/515,104 (filed on Oct. 28, 2003).

FIELD OF THE INVENTION

The present invention is in the general area of medical genetics and in the fields of chemistry, biochemical engineering, and oncology. More specifically, it relates to the use of organic and inorganic compounds, preferably aromatic and heterocyclic sulfonamides, to treat preneoplastic and/or neoplastic diseases by specifically inhibiting the carbonic anhydrase activity of the oncoprotein now known alternatively as the MN protein, the MN/CA IX isoenzyme, the MN/G250 protein or simply MN/CA IX or CA IX or MN. The present invention also relates to methods of treating preneoplastic and/or neoplastic diseases characterized by MN/CA IX overexpression by administering cell membrane-impermeant, inhibitors of MN/CA IX, preferably pyridinium derivatives of aromatic and heterocyclic sulfonamides. The invention further concerns diagnostic/prognostic methods including imaging methods, for preneoplastic/neoplastic diseases, using the disclosed potent CA IX-specific inhibitors, and gene therapy with vectors conjugated to said inhibitors.

BACKGROUND OF THE INVENTION

The instant inventors, Dr. Silvia Pastorekova and Dr. Jaromir Pastorek, with Dr. Jan Zavada ["Zavada et al."], discovered MN/CA IX, a cancer related cell surface protein originally named MN. [73, 123; Zavada et al., U.S. Pat. No. 5,387,676 (Feb. 7, 1995).] Zavada et al., WO 93/18152 (published Sep. 16, 1993) and Zavada et al., WO 95/34650 (published Dec. 21, 1995) disclosed the discovery of the MN gene and protein and the strong association of MN gene expression and tumorigenicity led to the creation of methods that are both diagnostic/prognostic and therapeutic for cancer and precancerous conditions. Zavada et al. disclosed further aspects of the MN/CA IX protein and the MN/CA9 gene in Zavada et al., WO 00/24913 (published May 4, 2000).

Zavada et al. cloned and sequenced the MN cDNA and gene, and revealed that MN belongs to a carbonic anhydrase family of enzymes that catalyze the reversible hydration of carbon dioxide to bicarbonate and proton [66, 72]. MN protein (renamed to carbonic anhydrase IX, CA IX) is composed of an extracellular part containing a N-terminal proteoglycan-like region and a catalytically active carbonic anhydrase domain. It is anchored in the plasma membrane by a single transmembrane region and a short intracytoplasmic tail.

Expression of CA IX is restricted to only few normal tissues [74], but is tightly associated with tumors [123]. It is also regulated by cell density in vitro [52] and is strongly induced by tumor hypoxia both in vitro and in vivo [121]. Numerous clinical papers describe the value of CA IX as an indicator of poor prognosis. All CA IX-related studies performed so far support the assumption made in the original Zavada et al., U.S. Pat. No. 5,387,676 that CA IX is useful as a diagnostic and/or prognostic tumor marker and as a therapeutic target.

MN/CA IX consists of an N-terminal proteoglycan-like domain that is unique among the CAs, a highly active CA catalytic domain, a single transmembrane region and a short intracytoplasmic tail [66, 72, 74, 116]. CA IX is particularly interesting for its ectopic expression in a multitude of carcinomas derived from cervix uteri, ovarian, kidney, lung, esophagus, breast, colon, endometrial, bladder, colorectal, prostate, among many other human carcinomas, contrasting with its restricted expression in normal tissues, namely in the epithelia of the gastrointestinal tract [8, 11, 21, 35, 41, 48, 50, 51, 56, 66, 72, 74, 86, 110, 111, 113, 116, 121, 122].

Uemura et al. [112] reported in 1997 that the G250 antigen was identical to MN/CA IX, years after MN/CA IX had been discovered and sequenced by Zavada et al. {[73, 123]; see also Pastorek et al. [72] and Opavsky et al. [66]}. Uemura et al. [112] stated: "Sequence analysis and database searching revealed that G250 antigen is identical to MN a human tumor-associated antigen identified in cervical carcinoma (Pastorek et al., 1994)."

MN/CA9 and MN/CA IX—Sequence Similarities

FIGS. 1A-C shows the full-length MN/CA9 cDNA sequence of 1522 base pairs (bps) [SEQ ID NO: 1], and the full-length MN/CA IX amino acid (aa) sequence of 459 aa [SEQ ID NO: 2]. FIGS. 2A-F provides the 10,898 bp genomic sequence of MN/CA9 [SEQ ID NO: 3].

Computer analysis of the MN cDNA sequence was carried out using DNASIS and PROSIS (Pharmacia Software packages). GenBank, EMBL, Protein Identification Resource and SWISS-PROT databases were searched for all possible sequence similarities. In addition, a search for proteins sharing sequence similarities with MN was performed in the MIPS databank with the FastA program [75].

The proteoglycan-like domain [aa 53-111; SEQ ID NO: 4] which is between the signal peptide and the CA domain, shows significant homology (38% identity and 44% positivity) with a keratan sulphate attachment domain of a human large aggregating proteoglycan aggrecan [28].

The CA domain [aa 135-391; SEQ ID NO: 5] is spread over 265 aa and shows 38.9% amino acid identity with the human CA VI isoenzyme [5]. The homology between MN/CA IX and other isoenzymes is as follows: 35.2% with CA II in a 261 aa overlap [63], 31.8% with CA I in a 261 aa overlap [7], 31.6% with CA IV in a 266 aa overlap [65], and 30.5% with CA III in a 259 aa overlap [55].

In addition to the CA domain, MN/CA IX has acquired both N-terminal and C-terminal extensions that are unrelated to the other CA isoenzymes. The amino acid sequence of the C-terminal part, consisting of the transmembrane anchor and the intracytoplasmic tail, shows no significant homology to any known protein sequence.

The MN gene (MN/CA9 or CA9) was clearly found to be a novel sequence derived from the human genome. The overall sequence homology between the cDNA MN/CA9 sequence and cDNA sequences encoding different CA isoenzymes is in a homology range of 48-50% which is considered by ones in the art to be low. Therefore, the MN/CA9 cDNA sequence is not closely related to any CA cDNA sequences.

Very few normal tissues have been found to express MN protein to any significant degree. Those MN-expressing normal tissues include the human gastric mucosa and gallbladder epithelium, and some other normal tissues of the alimentary tract. Paradoxically, MN gene expression has been found to be lost or reduced in carcinomas and other preneoplastic/neoplastic diseases in some tissues that normally express MN, e.g., gastric mucosa.

CA IX and Hypoxia

Strong association between CA IX expression and intratumoral hypoxia (either measured by microelectrodes, or detected by incorporation of a hypoxic marker pimonidazole, or by evaluation of extent of necrosis) has been demonstrated in the cervical, breast, head and neck, bladder and non-small cell lung carcinomas (NSCLC) [8, 11, 21, 35, 48, 56, 111, 122]. Moreover, in NSCLC and breast carcinomas, correlation between CA IX and a constellation of proteins involved in angiogenesis, apoptosis inhibition and cell-cell adhesion disruption has been observed, possibly contributing to strong relationship of this enzyme to a poor clinical outcome [8]. Hypoxia is linked with acidification of extracellular milieu that facilitates tumor invasion and CA IX is believed to play a role in this process via its catalytic activity [86]. Thus, inhibition of MN/CA IX by specific inhibitors is considered to constitute a novel approach to the treatment of cancers in which CA IX is expressed.

CAIs

Teicher et al. [106] reported that acetazolamide—the prototypical CA inhibitor (CAI)—functions as a modulator in anticancer therapies, in combination with different cytotoxic agents, such as alkylating agents; nucleoside analogs; platinum derivatives, among other such agents, to suppress tumor metastasis and to reduce the invasive capacity of several renal carcinoma cell lines (Caki-1, Caki-2, ACHN, and A-498). Such studies demonstrate that CAIs may be used in the management of tumors that overexpress one or more CA isozymes. It was hypothesized that the anticancer effects of acetazolamide (alone or in combination with such drugs) might be due to the acidification of the intratumoral environment ensuing after CA inhibition, although other mechanisms of action of this drug were not excluded [20]. Chegwidden et al. 2001 hypothesized that the in vitro inhibition of growth in cell cultures, of human lymphoma cells with two other potent, clinically used sulfonamide CAIs, methazolamide and ethoxzolamide, is probably due to a reduced provision of bicarbonate for nucleotide synthesis ($HCO_3^-$ is the substrate of carbamoyl phosphate synthetase II) as a consequence of CA inhibition [20].

All the six classical CAIs (acetazolamide, methazolamide, ethoxzolamide, dichlorophenamide, dorzolamide, and dichlorophenamide) used in clinical medicine or as diagnostic tools, show some tumor growth inhibitory properties [18, 78, 101, 102].

The inventors, Dr. Claudia Supuran and Dr. Andrea Scozzafava, reported the design and in vitro antitumor activity of several classes of sulfonamide CAIs, shown to act as nanomolar inhibitors against the classical isozymes known to possess critical physiological roles, such as CA I, CA II and CA IV. Those compounds were also shown to exert potent inhibition of cell growth in several leukemia, non-small cell lung, ovarian, melanoma, colon, CNS, renal, prostate and breast cancer cell lines, with $GI_{50}$ values of 10-75 nM in some cases [77, 91, 92, 100].

Wingo et al. reported that three classic sulfonamide drugs (acetozolamide, ethoxzolamide and methoxzolamide) inhibited CA IX carbonic anhydrase activity with values of $K_I$ in the nanomolar range [116]. However, until the present invention, no systematic structure-activity relationship study of sulfonamide inhibition of CA IX, alone or in comparison to other CA isozymes had been been performed.

Certain pyridinium derivatives of aromatic/heterocyclic sulfonamides have shown nanomolar affinities both for CA II, as well as CA IV, and more importantly, they were unable to cross the plasma membranes in vivo [17].

Sterling et al. [85] investigated the functional and physical relationship between the downregulated in adenoma bicarbonate transporter and CA II, by using membrane-impermeant sulfonamide inhibitors (in addition to the classical inhibitors such as acetazolamide), which could clearly discriminate between the contribution of the cytosolic and membrane-associated isozymes in these physiological processes.

CAS

Carbonic anhydrases (CAs) form a large family of genes encoding zinc metalloenzymes of great physiological importance. As catalysts of reversible hydration of carbon dioxide, these enzymes participate in a variety of biological processes, including respiration, calcification, acid-base balance, bone resorption, formation of aqueous humor, cerebrospinal fluid, saliva and gastric acid [reviewed in Dodgson et al. (27)]. CAs are widely distributed in different living organisms. In higher vertebrates, including humans, 14 different CA isozymes or CA-related proteins (CARP) have been described, with very different subcellular localization and tissue distribution [40, 93, 95, 94, 102]. Basically, there are several cytosolic forms (CA I-III, CA VII), four membrane-bound isozymes (CA IV, CA IX, CA XII and CA XIV), one mitochondrial form (CA V) as well as a secreted CA isozyme, CA VI [40, 93, 94, 95, 102].

It has been shown that some tumor cells predominantly express only some membrane-associated CA isozymes, such as CA IX and CA XII [2, 67, 68, 78, 87, 93, 95]. Occasionally, nuclear localization of some isoenzymes has been noted [64, 69, 70]. Not much is presently known about the cellular localization of the other isozymes.

CAs and CA-related proteins show extensive diversity in their tissue distribution, levels, and putative or established biological functions [105]. Some of the CAs are expressed in almost all tissues (CA II), while the expression of others appears to be more restricted (e.g., CA VI and CA VII in salivary glands [32, 69, 71]. The CAs and CA-related proteins also differ in kinetic properties and susceptibility to inhibitors [82].

Most of the clinically used sulfonamides mentioned above are systemically acting inhibitors showing several undesired side effects due to inhibition of many of the different CA isozymes present in the target tissue/organ (14 isoforms are presently known in humans) [93, 94, 95, 102]. Therefore, many attempts to design and synthesize new sulfonamides were recently reported, in order to avoid such side effects [13, 17, 42, 62, 80, 99, 100]. At least four CA isozymes (CA IV, CA IX, CA XII and CA XIV) are associated to cell membranes, with the enzyme active site generally oriented extracellularly [93, 94, 95, 102]. Some of these isozymes were shown to play pivotal physiological roles (such as for example CA IV and XII in the eye, lungs and kidneys, CA IX in the gastric mucosa and many tumor cells) [3, 18, 22, 29, 49, 67, 68, 83, 93, 94, 95, 102], whereas the function of other such isozymes (CA XIV) is for the moment less well understood [93, 95]. Due to the extracellular location of these isozymes, if membrane-impermeant CA inhibitors (CAIs) could be designed, only membrane-associated CAs would be affected.

The first approach towards introducing the membrane-impermeability to CAIs from the historical point of view was that of attaching aromatic/heterocyclic sulfonamides to polymers, such as polyethyleneglycol, aminoethyldextran, or dextran [39, 60, 107]. Such compounds, possessing molecular weights in the range of 3.5-99 kDa, prepared in that way, showed indeed membrane-impermeability due to their high molecular weights, and selectively inhibited in vivo only CA IV and not the cytosolic isozymes (primarily CA II), being used in several renal and pulmonary physiological studies

[39, 60, 107]. Due to their macromolecular nature, such inhibitors could not be developed as drugs/diagnostic tools, since in vivo they induced potent allergic reactions [39, 60, 93, 95, 107]. A second approach for achieving membrane-impermeability is that of using highly polar, salt-like compounds. Only one such sulfonamide has until recently been used in physiological studies, QAS (quaternary ammonium sulphanilamide), which has been reported to inhibit only extracellular CAs in a variety of arthropods (such as the crab *Callinectes sapidus*) and fish [57]. The main draw-back of QAS is its high toxicity in higher vertebrates [57].

Enzyme activity of carbonic anhydrases (including that of CA IX) can be efficiently blocked by sulfonamide inhibitors. That fact has been therapeutically exploited in diseases caused by excessive activities of certain CA isoforms (e.g. CA II in glaucoma). There is also an experimental evidence that sulfonamides may block tumor cell proliferation and invasion in vitro and tumor growth in vivo, but the targets of those sulfonamides have not been identified yet. However, the sulfonamides available so far indiscriminately inhibit various CA isoenzymes (14 are presently known in humans) that are localized in different subcellular compartments and play diverse biological roles. This lack of selectivity compromises the clinical utilization of these compounds (due to undesired side effects caused by concurrent inhibition of many CA isoforms) and represents a main drawback also for the sulfonamide application against CA IX in anticancer therapy.

Thus, there is a need in the art for membrane-impermeant, potent CA IX inhibitors, which would become doubly selective inhibitors for CA IX. The inventors have previously made and described some of the membrane-impermeant molecules described here; however, they were characterized only for their ability to inhibit CA I, CA II and CA IV. While others have studied effects of selective inhibition of extracellular CA by membrane impermeant agents in retinal prigmented epithelia or muscle [34, 120], these agents have not been characterized for their ability to inhibit CA IX. Since CA IX is one of the few extracellular carbonic anhydrases, a membrane-impermeant selective inhibitor of CA IX would be doubly selective for this enzyme and thereby avoid side effects associated with nonspecific CA inhibition.

SUMMARY OF THE INVENTION

The inventors approached the problem of lack of selectivity of CAIs by taking advantage of features that distinguish CA IX from the other CA isoforms. First of all, CA IX is an integral plasma membrane protein with an active site exposed on the extracellular side. In this respect, it is similar to some CAs (CA IV, CA XII and CA XIV) but differs from all other isoforms. Among these membrane-bound isoenzymes, CA IX shows some differences in the amino acid sequence of the catalytic domain that may influence the topology of the active site cavity and hence the interaction with sulfonamides. In addition, unlike the other CA isoforms, CA IX is expressed preferentially in hypoxic areas of tumors with poor prognosis.

The inventors evaluated inhibition profiles of CA IX with a series of aromatic and heterocyclic compounds and found that some of them inhibit CA IX more efficiently than the other widely distributed isoforms CA I, II and IV. Several nanomolar CA IX inhibitors have been detected both among the aromatic and the heterocyclic compounds. This finding is very promising for the design of CA IX-specific inhibitors by modification of their physico-chemical properties such as charge, size and bioreductivity to conform the characteristic properties of CA IX.

The inventors found that some of the more bulky compounds that strongly inhibited CA IX were very weak inhibitors of CA I, II and IV, possibly due to the fact that the CA IX active site cavity is larger than that of the other investigated isoenzymes. The compounds of such type, identified by screening as disclosed herein, based on the selective inhibition of tumor-associated isoform CA IX may be particularly preferred CA IX specific inhibitors, that could be used in new anticancer therapies and in the diagnostic/prognostic methods of this invention.

The inventors have shown that CA IX is capable of reducing E-cadherin-mediated cell-cell adhesion that may be important for increased invasion capacity of the cells [103]. CA IX was found by the inventors also to contribute to acidification of extracellular pH in hypoxia but not in normoxia (unpublished data). The latter result indicates that hypoxia up-regulates both expression level and enzyme activity of CA IX, that is, hypoxia activates the CA catalytic activity of CA IX. That is a very important finding because intratumoral hypoxia is a clinically relevant factor increasing aggressiveness of tumor cells and reducing success of therapy. Hypoxia is usually accompanied by acidification of extracellular microenvironment, which facilitates tumor invasion and metastasis. CA IX appears to participate in this phenomenon by catalyzing hydration of carbon dioxide to generate bicarbonate ions that are then transported into cell interior and protons that acidify extracellular pH. Therefore, inhibition of the CA IX catalytic activity resulting in reduced extracellular acidification may have direct anticancer effects or may modulate efficiency of those conventional chemotherapeutic drugs whose uptake is pH-dependent.

The instant invention is related to (1) the recognition that certain carbonic anhydrase inhibitors (CAIs), preferably sulfonamides, selectively target the cancer-related, hypoxia-induced MN/CA IX; (2) the use of such CAIs, preferably sulfonamides, as lead compounds for the design and synthesis of MN/CA IX-specific inhibitors; (3) the employment of said MN/CA IX-specific inhibitors for anticancer therapy based upon the inhibition of MN/CA IX-mediated acidification of tumor microenvironments; and (4) the use of the specificity of potent MN/CA IX-specific inhibitors for diagnostic/prognostic methods including imaging methods, such as scintigraphy, and for gene therapy. The invention is particularly directed to the use of CA IX-specific inhibitors for the development of drugs possessing anticancer properties and to modulate conventional chemotherapy for preneoplastic and neoplastic disease characterized by CA IX expression, particularly CA IX overexpression.

In one aspect, the invention concerns methods of treating a mammal for a pre-cancerous or cancerous disease, wherein said disease is characterized by overexpression of MN/CA IX protein, comprising administering to said mammal a therapeutically effective amount of a composition comprising a compound, wherein said compound is selected from the group consisting of organic and inorganic molecules, and wherein said compound is determined to be a potent inhibitor of MN/CA IX enzymatic activity in a screening assay comprising:

a) preparing serial dilutions of said compound and serial dilutions of MN/CA IX protein or a fragment of the MN/CA IX protein that comprises the carbonic anhydrase domain;

b) preincubating a dilution of said compound with a dilution of said MN/CA IX protein or said MN/CA IX protein fragment for ten minutes at 20° C.;

c) combining said preincubated mixture of said diluted compound and said diluted MN/CA IX protein or protein fragment with a substrate, consisting essentially of a saturated $CO_2$ solution, phenol red to 0.2 mM, $Na_2SO_4$ to 0.1M, and Hepes buffer (pH 7.5) to 10 mM, in a reaction vessel for a period of 10 to 100 seconds at 20° C.;

d) concurrently measuring the optical density, at the absorbance maximum of 557 nm, of the contents of said reaction vessel, using a stopped flow spectrophotometer; and e) determining the inhibition constant $K_I$ of said compound;

wherein if said inhibition constant $K_I$ is determined to be less than about 50 nanomolar, said compound is determined be a potent inhibitor of MN/CA IX enzymatic activity; and wherein said compound is not selected from the group consisting of acetazolamide, ethoxzolamide, methazolamide and cyanate. Said mammal is preferably human, and said $K_I$ is preferably less than about 35 nanomolar, more preferably less than about 25 nanomolar, and still more preferably less than about 10 nanomolar.

Such methods can also be framed as methods of treating precancer and/or cancer, or inhibiting the growth of precancerous and/or cancerous cells in a mammalian subject, wherein said precancer and cancer are characterized by the overexpression of MN/CA IX. Said methods can also be framed as inhibiting the growth of such precancerous or cancerous mammalian cells overexpressing MN/CA IX comprising contacting said cells with a CA IX-specific inhibitor of this invention.

The CA IX-specific inhibitors of this invention can be administered in a therapeutically effective amount, preferably dispersed in a physiologically acceptable nontoxic liquid vehicle. Different routes of administration may be preferred depending on the site or type of preneoplastic/neoplastic disease, for example, solid or non-solid tumor or metastasis. In general, parenteral administration would be preferred to avoid undesired effects of systemic treatment, for example, those that could be occasioned by binding of the inhibitors to the gastrointestinal mucosa. Injection into or into the vicinity of the preneoplastic/neoplastic disease would be generally preferred. For example, such injections could be intravenous, intraperitoneal, rectal, subcutaneous, intramuscular, intraorbital, intracapsular, intraspinal, intrasternal, intramedullary, intralesional, intradermal, among other routes of injection. Also, other modes of administration, for example, by suppository or topically, can be used as would be appropriate to the target disease. The pharmaceutical formulation would be designed in accordance with known standards as suitable for the route of administration.

Said CA IX-specific inhibitors are preferably organic, more preferably aromatic or heterocyclic, and still more preferably an aromatic sulfonamide or a heterocyclic sulfonamide. Said aromatic sulfonamide may be a substituted aromatic sulfonamide, wherein said aromatic sulfonamide comprises an aromatic ring structure bearing a sulfonamide moiety bonded to said ring structure and optionally bearing one or more substituents independently selected from the group consisting of halogeno, nitro, and an alkylamino group, wherein the alkyl radical of said alkylamino group comprises 1 to 4 carbon atoms.

Preferably the CA IX-specific inhibitors of this invention are more potent inhibitors of MN/CA IX enzymatic activity than of the enzymatic activity of a carbonic anhydrase selected from the group consisting of CA I, CA II and CA IV. More preferably, the CA IX-specific inhibitors are more potent inhibitors of MN/CA IX enzymatic activity than of the enzymatic activity of at least two carbonic anhydrases selected from the group consisting of CA I, CA II and CA IV. Still more preferably, the CA IX-specific inhibitors are more potent inhibitor of MN/CA IX enzymatic activity than of the enzymatic activity of each of the carbonic anhydrases in the group consisting of CA I, CA II and CA IV.

However, since CA II is a particularly abundant and significant CA, that is cytosolic, it is important when the CA IX-specific inhibitors of this invention are not membrane-impermeant, that they may be more potent inhibitors of MN/CA IX enzymatic activity than of the enzymatic activity of CA II. A method comprising the following steps provides an exemplary screening assay that can be used to determine the $K_I$ of a compound in inhibiting the enzymatic activity of CA II:

a) preparing serial dilutions of said compound and serial dilutions of CA II;

b) preincubating a dilution of said compound with a dilution of CA II for ten minutes at 20° C.;

c) combining said preincubated mixture of said compound and said CA II with a substrate solution, consisting essentially of 4-nitrophenylacetate in anhydrous acetonitrile, in a reaction vessel for a period of 1 to 3 minutes at 25° C.;

d) concurrently measuring the optical density, at the absorbance maximum of 400 nm, of the contents of said reaction vessel, using a spectrophotometer; and e) determining the inhibition constant $K_I$ of said compound.

Exemplary and preferred aromatic sulfonamide or heterocyclic sulfonamide CA IX-specific inhibitors of this invention are selected from the group consisting of:

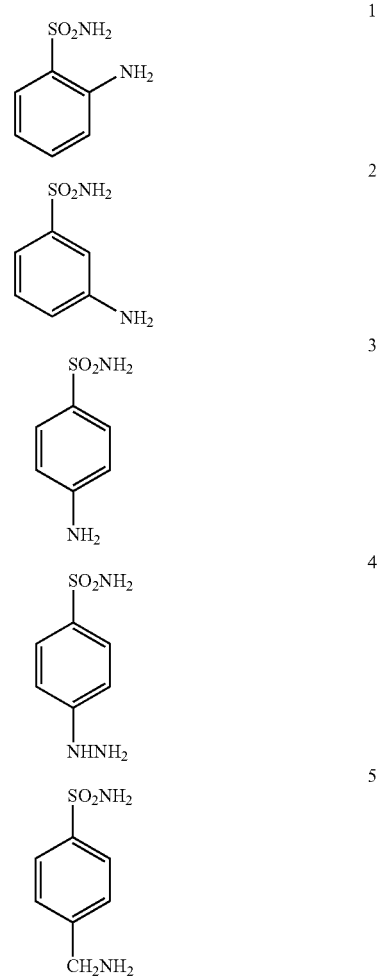

-continued
6
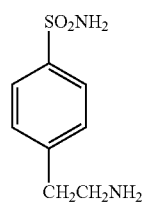
7
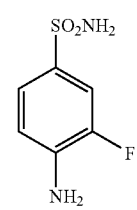
8
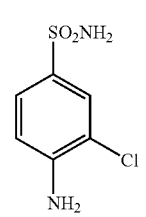
9
10
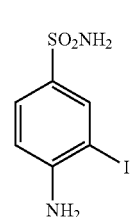
11
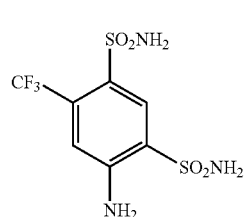
12
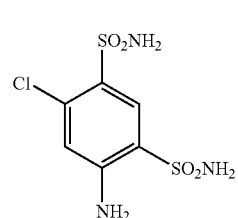
13
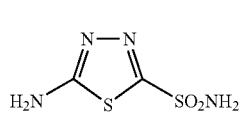
-continued
14
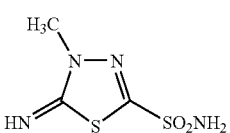
15
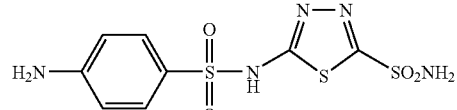
16
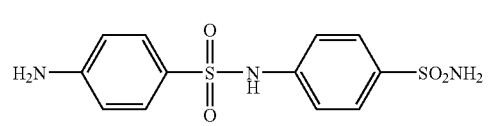
17
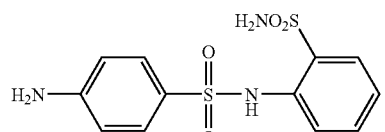
18
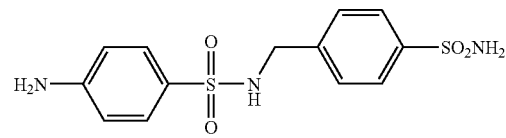
19
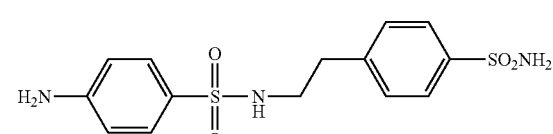
20
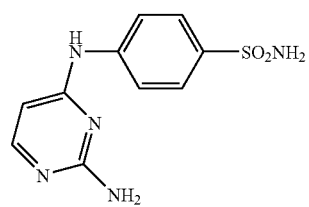
21
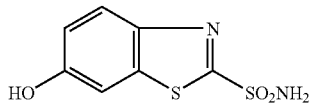
22
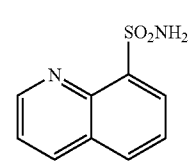
23
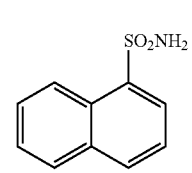

-continued

24
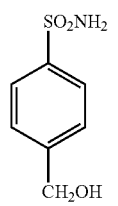

25
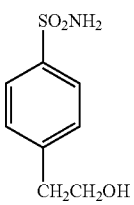

26
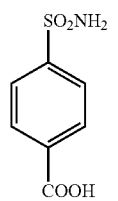

Exemplary preferred aromatic sulfonamide CA IX-specific inhibitors are selected from the group consisting of:

1
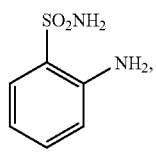

6
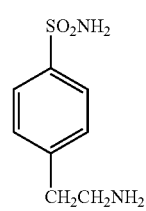

23
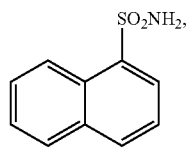

24
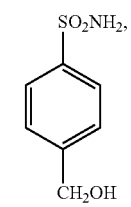

-continued

25
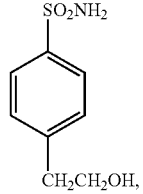

26
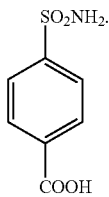

A preferred aromatic sulfonamide CA IX-specific inhibitor can be that wherein a halogen atom is bonded to at least one carbon atom in the aromatic ring of said aromatic sulfonamide.

Preferred heterocyclic sulfonamide CA IX-specific inhibitors can be substituted heterocyclic sulfonamides, wherein said substituted heterocyclic sulfonamide comprises a heterocyclic ring structure bearing a sulfonamide moiety bonded to said ring structure and optionally bearing one or more substituents independently selected from a group consisting of halogeno, nitro, and an alkylamino group, wherein the alkyl radical of said alkylamino group comprises 1 to 4 carbon atoms. Preferred heterocyclic sulfonamide CA IX-specific inhibitors may be halogenated.

Further preferred heterocyclic sulfonamide CA IX-specific inhibitors are selected from the group consisting of:

14
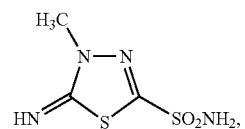

15
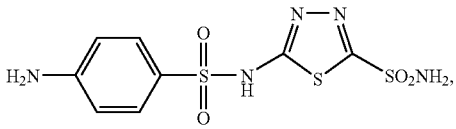

21
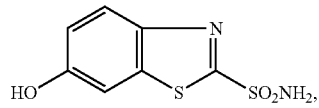

22
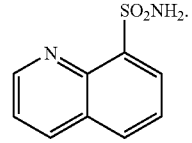

Further preferred methods of treating mammals for precancerous or cancerous disease, wherein said disease is characterized by overexpression of MN/CA IX protein, comprise administering to said mammal membrane-impermeant CA IX-specific inhibitors. A therapeutically effective amount of such a membrane-impermeant CA IX-specific inhibitor can be administered in a composition comprising the membrane-impermeant compound, wherein said membrane-impermeant inhibitor compound is selected from the group consisting of organic and inorganic molecules, and wherein said membrane-impermeant compound is determined to be a potent inhibitor of MN/CA IX enzymatic activity in a screening assay comprising:

a) preparing serial dilutions of said membrane-impermeant compound and serial dilutions of MN/CA IX protein or a fragment of the MN/CA IX protein that comprises the carbonic anhydrase domain;

b) preincubating a dilution of said membrane-impermeant compound with a dilution of said MN/CA IX protein or said MN/CA IX protein fragment for ten minutes at 20° C.;

c) combining said preincubated mixture of said diluted compound and said diluted MN/CA IX protein or protein fragment with a substrate, consisting essentially of a saturated $CO_2$ solution, phenol red to 0.2 mM, $Na_2SO_4$ to 0.1M, and Hepes buffer (pH 7.5) to 10 mM, in a reaction vessel for a period of 10 to 100 seconds at 20° C.;

d) concurrently measuring the optical density, at the absorbance maximum of 557 nm, of the contents of said reaction vessel, using a stopped flow spectrophotometer; and e) determining the inhibition constant $K_I$ of said membrane-impermeant compound, wherein if said inhibition constant $K_I$ is determined to be less than about 50 nanomolar, said membrane-impermeant compound is determined be a potent inhibitor of MN/CA IX enzymatic activity. The mammal is preferably a human, and the $K_I$ is preferably less than 35 nM, more preferably less than about 25 nM, and still more preferably less than about 10 nanomolar.

Such a membrane-impermeant CA IX specific inhibitor compound is preferably organic, and more preferably a pyridinium derivative of an aromatic sulfonamide or a pyridinium derivative of a heterocyclic sulfonamide. Such membrane-impermeant CA IX-specific inhibitor compounds are preferably more potent inhibitors of MN/CA IX enzymatic activity than of the enzymatic activity of a carbonic anhydrase selected from the group consisting of CA I, CA II and CA IV, and still more preferably more potent inhibitors of MN/CA IX enzymatic activity than of the enzymatic activity of at least two carbonic anhydrases selected from the group consisting of CA I, CA II and CA IV. Further more preferably, said membrane-impermeant CA IX-specific inhibitor compounds are more potent inhibitors of MN/CA IX enzymatic activity than of the enzymatic activity of each of the carbonic anhydrases in the group consisting of CA I, CA II and CA IV. Since both CA IX and CA IV are membrane bound CAs, it is particularly important that the membrane-impermeant CA IX-specific inhibitor compounds are more potent inhibitors of MN/CA IX enzymatic activity than of the enzymatic activity of CA IV.

A method comprising the following steps provides an exemplary screening assay that can be used to determine the $K_I$ of a compound inhibiting the enzymatic activity of CA IV:

a) preparing serial dilutions of said membrane-impermeant compound and serial dilutions of CA IV;

b) preincubating a dilution of said membrane-impermeant compound with a dilution of CA IV for ten minutes at 20° C.;

c) combining said preincubated mixture of said compound and said CA IV with a substrate solution, consisting essentially of 4-nitrophenylacetate in anhydrous acetonitrile, in a reaction vessel for a period of 1 to 3 minutes at 25° C.;

d) concurrently measuring the optical density, at the absorbance maximum of 400 nm, of the contents of said reaction vessel using a spectrophotometer; and e) determining the inhibition constant $K_I$ of said membrane-impermeant compound.

Preferred membrane-impermeant CA IX-specific inhibitor compounds that are pyridinium derivatives of aromatic sulfonamides are selected from the group consisting of sulfanilamide, homosulfanilamide and 4-aminoethyl-benzenesulfonamide. Preferred pyridinium derivatives of aromatic sulfonamides can have the general formula of:

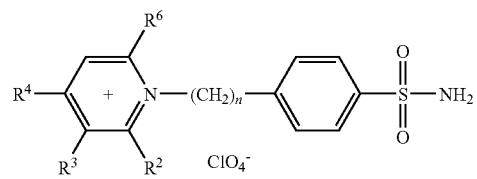

wherein
n is 0, 1, or 2;
R2, R3, R4 and R6 are each independently selected from the group consisting of hydrogen, alkyl moieties comprising from 1 to 12 carbon atoms, and aryl moieties. Further preferred are such compounds wherein
R2 is selected from the group consisting of methyl, ethyl, n-propyl, iso-propyl, n-butyl, tert-butyl and phenyl;
R3 is selected from the group consisting of hydrogen and methyl;
R4 is selected from the group consisting of hydrogen, methyl and phenyl; and
R6 is selected from the group consisting of methyl, ethyl, n-propyl, iso-propyl, and phenyl. Still further preferred are such compounds wherein
R3 is hydrogen;
R4 and R6 are phenyl;
when n is 0, R2 is selected from the group consisting of methyl, ethyl, n-propyl, iso-propyl, n-butyl, and phenyl; and
when n is 1 or 2, R2 is selected from the group consisting of methyl, ethyl, n-propyl, iso-propyl, n-butyl, tert-butyl, and phenyl. Other preferred such compounds include those wherein
R3 is hydrogen;
R4 is phenyl; and
when n is 0, R2 and R6 are the same and are selected from the group consisting of methyl, ethyl, n-propyl, and iso-propyl; and
when n is 1 or 2, R2 and R6 are the same and are selected from the group consisting of methyl, ethyl, n-propyl and iso-propyl. Other preferred compounds include those wherein R2, R3, R4 and R6 are methyl. Still further preferred are such CA IX-specific inhibitor compounds wherein
when n is 0, 1 or 2, R2, R4 and R6 are methyl, and R3 is hydrogen; or
when n is 1 or 2, R2 is iso-propyl, R3 is hydrogen, R4 is methyl, and R6 is methyl or iso-propyl; or
when n is 1 or 2, R2 and R6 are phenyl, and R3 and R4 are hydrogen.

Still more preferred such compounds are those wherein
when n is 2, R2 and R6 are methyl, R3 is hydrogen, and R4 is phenyl; or
when n is 2, R2 and R6 are ethyl, R3 is hydrogen, and R4 is phenyl; or
when n is 2, R2, R3, R4 and R6 are methyl.

When said CA IX-specific inhibitors are membrane-impermeant pyridinium derivatives of a heterocyclic sulfonamides, a preferred compound is a pyridinium derivative of aminobenzolamide.

Preferred CA IX-specific inhibitor compounds that are pyridinium derivatives of heterocyclic sulfonamides may have the general formula of:

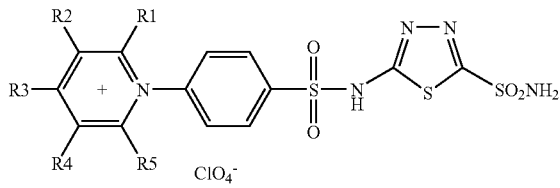

wherein R1, R2, R3, R4 and R5 are each independently selected from the group consisting of hydrogen, alkyl moieties comprising from 1 to 12 carbon atoms, and aryl moieties. Further preferred are such compounds wherein
R1 is selected from the group consisting of methyl, ethyl, iso-propyl, n-propyl, n-butyl, tert-butyl and phenyl;
R2 is selected from the group consisting of hydrogen and methyl;
R3 is selected from the group consisting of hydrogen, methyl, n-nonyl, and phenyl;
R4 is selected from the group consisting of hydrogen and methyl; and
R5 is selected from the group consisting of methyl, ethyl, iso-propyl, n-propyl, n-butyl, tert-butyl, n-nonyl and phenyl. Further preferred are such compounds wherein
R2 and R4 are hydrogen;
R3 is methyl; and
R1 and R5 are the same and selected from the group consisting of methyl, iso-propyl, and tert-butyl. Still further preferred are such compounds wherein
R2 and R4 are hydrogen;
R3 is phenyl; and
R1 and R5 are the same and selected from the group consisting of methyl, ethyl, iso-propyl, n-propyl, n-butyl, and phenyl. Additionally are preferred such compounds wherein
R1 is selected from the group consisting of methyl, ethyl, iso-propyl, n-propyl, and n-butyl;
R2 and R4 are hydrogen; and
R3 and R5 are phenyl. Other preferred such compounds are those wherein
R2 and R4 are hydrogen, R3 is hydrogen or methyl, and R1 and R5 are phenyl; or
R1, R2, and R5 are methyl, R3 is phenyl, and R4 is hydrogen; or
R1 and R4 are methyl, R2 is hydrogen, and R3 and R5 are n-nonyl.

Also preferred such compounds are those wherein
R1 is methyl or iso-propyl, R3 and R5 are methyl, and R2 and R4 are hydrogen; or
R1 and R5 are the same and are methyl or ethyl, R2 and R4 are hydrogen, and R3 is phenyl; or
R1, R2, R3 and R5 are methyl, and R4 is hydrogen.

In another aspect, this invention concerns methods of inhibiting tumor growth in a patient having a tumor, the cells of which tumor are characterized by overexpression of MN/CA IX protein, comprising administering to said patient a therapeutically effective amount of a composition comprising a compound, wherein said compound is selected from the group consisting of organic and inorganic molecules, and wherein said compound is determined to be a potent inhibitor of MN/CA IX enzymatic activity in a screening assay as outlined above for MN/CA IX using a saturated $CO_2$ solution.

Still further, this invention concerns novel compounds that are useful as CA IX-specific inhibitors in a variety of methods disclosed herein. Such novel compounds include pyridinium derivatives of heterocyclic sulfonamides with the general formula of:

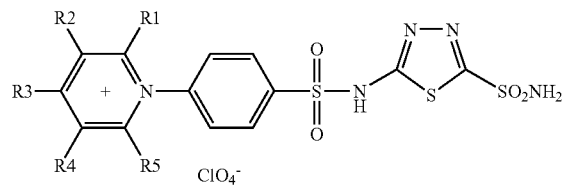

wherein
R1 is selected from the group consisting of methyl, ethyl, iso-propyl, n-propyl, n-butyl, tert-butyl and phenyl;
R2 is selected from the group consisting of hydrogen and methyl;
R3 is selected from the group consisting of hydrogen, methyl, n-nonyl and phenyl;
R4 is selected from the group consisting of hydrogen and methyl; and
R5 is selected from the group consisting of methyl, ethyl, iso-propyl, n-propyl, n-butyl, tert-butyl, n-nonyl and phenyl, except that
R1 cannot be methyl when R2 and R4 are hydrogen and R3 and R5 are methyl; and
R1 cannot be methyl when R2 and R4 are hydrogen, R3 is phenyl and R5 is methyl; and
R1 cannot be phenyl when R2 and R4 are hydrogen and R3 and R5 are phenyl. Preferred such pyridinium derivatives of heterocyclic sulfonamides include those wherein
R2 and R4 are hydrogen;
R3 is methyl; and
R1 and R5 are the same and selected from the group consisting of iso-propyl and tert-butyl, and those wherein
R2 and R4 are hydrogen;
R3 is phenyl; and
R1 and R5 are the same and selected from the group consisting of ethyl, iso-propyl, n-propyl, and n-butyl, and further preferably those wherein
R1 is selected from the group consisting of methyl, ethyl, iso-propyl, n-propyl, n-butyl, and tert-butyl;
R2 and R4 are hydrogen; and
R3 and R5 are phenyl. Still further preferred are those pyridinium derivatives of heterocyclic sulfonamides, wherein
R1 is iso-propyl, R3 and R5 are methyl, and R2 and R4 are hydrogen; or
R2 and R4 are hydrogen, R3 is hydrogen or methyl, and R1 and R5 are phenyl; or
R1, R2, and R5 are methyl, R3 is phenyl, and R4 is hydrogen; or
R1, R2, R3 and R5 are methyl and R4 is hydrogen; or
R1 and R4 are methyl, R2 is hydrogen and R3 and R5 are n-nonyl.

In another therapeutic aspect of the invention, the CA IX-specific inhibitors can be conjugated to radioisotopes for administration. Also, the CA IX-specific inhibitors can be administred concurrently and/or sequentially with radiation and/or with a therapeutically effective amount in a physiologically acceptable formulation of one or more of the following compounds selected from the group consisting of: conventional anticancer drugs, chemotherapeutic agents, different inhibitors of cancer-related pathways, bioreductive drugs, CA IX-specific antibodies and CA IX-specific antibody fragments that are biologically active. Preferably said CA IX-specific antibodies and/or CA IX-specific antibody fragments are humanized or fully human, and may be attached to a cytotoxic entity.

In another therapeutic aspect, this invention concerns methods of treating a mammal for a precancerous or cancerous disease, wherein said disease is characterized by overexpression of MN/CA IX protein, comprising administering to said mammal a therapeutically effective amount in a physiologically acceptable formulation of a vector conjugated to a potent CA IX-specific inhibitor, wherein said vector expresses a wild-type gene that is absent from or mutated in a CA IX expressing cell, that is precancerous or cancerous, and wherein the wild type gene product has an anticancer effect in said cell; or wherein said vector comprises a gene that expresses a cytotoxic protein. An exemplary wild-type gene would be the von Hippel-Lindau gene known to be directly involved in the constitutive expression of CA IX in renal cell carcinoma.

Preferably said vector comprises a MN/CA IX promoter or a MN/CA IX promoter fragment, wherein said promoter or promoter fragment comprises one or more hypoxia response elements (HREs), and wherein said promoter or promoter fragment is operably linked to said wild-type gene or to said gene that expresses a cytotoxic protein. Preferably the CA IX-specific inhibitor conjugated to the vector has a $K_I$ as determined above in the $CO_2$ saturation assay to be less than about 50 nM, more preferably less than about 35 nM, still more preferably less than about 25 nM and still further more preferably less than about 10 nM. Preferably, said potent MN/CA IX inhibitor is not selected from the group consisting of acetazolamide, ethoxzolamide, methazolamide and cyanate.

Still in another aspect, this invention concerns methods that are diagnostic or diagnostic and prognostic for precancer or cancer. For example, such methods may comprise contacting a mammalian sample with a CA IX-specific inhibitor conjugated to a label or a visualizing means, and detecting or detecting and quantifying binding of said CA IX-specific inhibitor to cells in said sample by detecting or detecting and quantifying said label or said visualizing means on cells in said sample, wherein said detection or said detection and quantitation at a level above that for a control sample is indicative of precancerous or cancerous cells that overexpress CA IX in said sample.

Such methods can be of particular diagnostic and prognostic importance by detecting or detecting and quantitating CA IX activated by hypoxic conditions. Hypoxia combined with CA IX overepression indicates that the mammal from whom the sample was taken is considered to have a poorer prognosis, and decisions on treatment for said mammal are made in view of the presence of said hypoxic conditions. MN/CA IX as a hypoxia marker is useful in general in making therapeutic decisions. For example, a cancer patient whose tumor is known to express MN/CA IX at an abnormally high level would not be a candidate for certain kinds of chemotherapy and radiotherapy, but would be a candidate for hypoxia-selective chemotherapy.

Brown, J. M. [16] points out at page 157 that "solid tumours are considerably less well oxygenated than normal tissues. This leads to resistance to radiotherapy and anticancer chemotherapy, as well as predisposing to increased tumour metastases." Brown explains how tumor hypoxia can be exploited in cancer treatment. One strategy to exploit tumor hypoxia for cancer treatment proposed by Brown [16] is to use drugs that are toxic only under hypoxic conditions. Exemplary and preferred drugs that could be used under that strategy include tirapazamine and AQ4N, a di-N-oxide analogue of mitozantrome.

A second mode of exploiting hypoxia proposed by Brown [16] is by gene therapy strategies developed to take advantage of the selective induction of HIF-1. Brown notes that a tumor-specific delivery system can be developed wherein a promoter that is highly responsive to HIF-1 would drive the expression of a conditionally lethal gene under hypoxic but not normoxic conditions. The MN/CA IX promoter is just such a promoter highly responsive to hypoxia, as well as MN/CA IX promoter fragments comprising one or more HREs. "Expression of an enzyme not normally found in the human body could, under the control of a hypoxia-responsive promoter [the MN/Ca IX promoter], convert a nontoxic pro-drug into a toxic drug in the tumour." [Brown [16], page 160.] Exemplary is the use of the bacterial cytosine deaminase, which converts the nontoxic 5-fluorocytosine to the anticancer drug 5-fluorouracil (5FU) cited by Brown to Trinh et al. [109].

Ratcliffe et al., U.S. Pat. Nos. 5,942,434 and 6,265,390 explain how anti-cancer drugs become activated under hypoxia [119], but that the use of a drug activation system, wherein the enzyme that activates the drug is significantly increased under hypoxia, results in much enhanced therapeutic effect.

This invention further concerns methods for imaging tumors and/or metastases that express CA IX in a patient comprising the administration of a CA IX-specific inhibitor linked to an imaging agent to said patient. A preferred imaging method would encompass scintigraphy.

The assays of this invention are both diagnostic and/or prognostic, i.e., diagnostic/prognostic. The term "diagnostic/prognostic" is herein defined to encompass the following processes either individually or cumulatively depending upon the clinical context: determining the presence of disease, determining the nature of a disease, distinguishing one disease from another, forecasting as to the probable outcome of a disease state, determining the prospect as to recovery from a disease as indicated by the nature and symptoms of a case, monitoring the disease status of a patient, monitoring a patient for recurrence of disease, and/or determining the preferred therapeutic regimen for a patient. The diagnostic/prognostic methods of this invention are useful, for example, for screening populations for the presence of neoplastic or pre-neoplastic disease, determining the risk of developing neoplastic disease, diagnosing the presence of neoplastic and/or pre-neoplastic disease, monitoring the disease status of patients with neoplastic disease, and/or determining the prognosis for the course of neoplastic disease.

The present invention is useful for treating and for screening the presence of a wide variety of preneoplastic/neoplastic diseases including carcinomas, such as, mammary, colorectal, urinary tract, ovarian, uterine, cervical, endometrial, squamous cell and adenosquamous carcinomas; head and neck cancers; mesodermal tumors, such as, neuroblastomas and retinoblastomas; sarcomas, such as osteosarcomas and Ewing's sarcoma; and melanomas. Of particular interest are gynecological cancers including ovarian, uterine, cervical, vaginal, vulval and endometrial cancers, particularly ovarian, uterine cervical and endometrial cancers. Also of particular interest are cancers of the breast, of gastrointestinal tract, of the stomach including esophagus, of the colon, of the kidney, of the prostate, of the liver, of the urinary tract including bladder, of the lung, and of the head and neck. Gynecologic cancers of particular interest are carcinomas of the uterine cervix, endometrium and ovaries; more particularly such gynecologic cancers include cervical squamous cell carcinomas, adenosquamous carcinomas, adenocarcinomas as well as gynecologic precancerous conditions, such as metaplastic cervical tissues and condylomas.

The invention provides methods and compositions for evaluating the probability of the presence of malignant or pre-malignant cells, for example, in a group of cells freshly removed from a host. Such an assay can be used to detect tumors, quantitate their growth, and help in the diagnosis and prognosis of disease. The assays can also be used to detect the presence of cancer metastasis, as well as confirm the absence or removal of all tumor tissue following surgery, cancer chemotherapy and/or radiation therapy. It can further be used to monitor cancer chemotherapy and tumor reappearance.

The presence of MN antigen can be detected and/or quantitated using a number of well-defined diagnostic assays. Those in the art can adapt any of the conventional immunoassay formats to detect and/or quantitate MN antigen as herein disclosed. The immunoassays of this invention can be embodied in test kits which comprise the potent CA IX-specific inhibitors of this invention, appropriately labeled and/or linked to a visualizing means, as known in the art. Such test kits can be in solid phase formats, but are not limited thereto, and can also be in liquid phase format, and can be based on immunohistochemical assays, ELISAS, particle assays, radiometric or fluorometric assays either unamplified or amplified, using, for example, avidin/biotin technology, among other assay formats.

Exemplary CA IX-specific inhibitors of the invention are shown herein to treat transfected cells that constitutively express MN/CA IX compared to non-transfected cells with no MN/CA IX expression. The exemplary CA IX-specific inhibitors are shown to inhibit acidification of extracellular pH induced by MN/CA IX in cell cultures exposed to hypoxia.

Further, labeled exemplary CA IX-specific inhibitors, such as labeled sulfonamides, for example, conjugated to fluorescein isothiocyanate (FITC), are shown to bind to the surface of MN/CA IX transfected cells, and not to control cells, only in hypoxia but not in normoxia. Those experiments confirm that CA IX-specific inhibitors, such as the sulfonamide compounds described herein, can specifically target MN/CA IX under conditions characteristic of intratumoral microenvironments.

The CA IX-specific inhibitors of this invention can be used diagnostically and prognostically for precancer and cancer, and to determine the status of a patient, and therapeutically, individually or in different combinations with conventional therapeutic regimens to treat precancers and/or cancer. The CA IX-specific inhibitors may also be used in cancer research.

More particularly for treating precancer and/or cancer, the CA IX-specific inhibitors of this invention can be used to hinder cancer expansion and/or progression by blocking CA IX activity. The CA IX-specific inhibitors can be conjugated to radioisotopes for radiotherapy. The CA IX-specific inhibitors can be combined with CA IX-specific antibodies and a variety of conventional therapeutic drugs, different inhibitors of cancer-related pathways, bioreductive drugs, and/or radiotherapy, wherein different combinations of treatment regimens with the CA IX-specific inhibitors of this invention may increase overall treatment efficacy. Particularly, the CA IX-specific inhibitors of this invention may be combined with therapy using MN/CA IX-specific antibodies and/or CA IX-specific antibody fragments, preferably humanized CA IX-specific antibodies and/or biologically active fragments thereof, and more preferably fully human CA IX-specific antibodies and/or fully human CA IX-specific biologically active antibody fragments. Said CA IX-specific antibodies and biologically active CA IX-specific antibody fragments, preferably humanized and more preferably fully human, may be conjugated to a cytotoxic entity, for example, a cytotoxic protein, such as ricin A, among many other cytotoxic entities.

Still further, a CA IX-specific inhibitor of this invention could be coupled to a vector for targeted delivery to CA IX-specific expressing cells for gene therapy (for example, with the wild-type von Hippel-Lindau gene), or for effecting the expression of cytotoxic proteins, preferably wherein said vector comprises a MN/CA IX promoter or MN/CA IX promoter fragment comprising the MN/CA IX hypoxia response element (HRE) or a HRE of another gene, and more preferably wherein the CA IX promoter or CA IX promotor fragment comprises more than one HRE, wherein said HRE or HREs is or are either of MN/CA IX, and/or of other genes and/or of genetically engineered HRE consensus sequences in a preferred context.

Particularly, the CA IX-specific inhibitors of this invention can be used diagnostically/prognostically to detect precancerous and/or cancerous cells by binding to CA IX, preferably to CA IX activated by hypoxic conditions, wherein said CA IX specific inhibitors are coupled to a label or to some visualizing means. Such detection, particularly of hypoxic conditions, and CA IX overexpression, can be helpful in determining effective treatment options, and in predicting treatment outcome and the prognosis of disease development. Further the CA IX-specific inhibitors when labeled or linked to an appropriate visualizing means can be used for imaging tumors and/or metastases that express CA IX.

The CA IX-specific inhibitors of this invention can also be used in basic and pre-clinical research. For example, the CA IX-specific inhibitors can be used to study the regulation of CA IX enzyme activity, to study the role of CA IX in tumor growth and metabolism, and to study the role of CA IX in response to treatment by drugs, radiation, inhibitors and other therapeutic regimens.

Further methods are disclosed for the preparation of positively-charged, membrane-impermeant heterocyclic sulfonamide CA inhibitors with high affinity for the membrane-bound carbonic anhydrase CA IX. Particularly preferred CA IX-specific inhibitors are pyridinium derivatives of such aromatic and heterocyclic sulfonamides. The general structure of the preferred pyridinium derivatives of sulfonamides can be described as a pyridinium portion attached to the "tail" of an aromatic or heterocyclic sulphonamide portion of the compound.

Further provided are screening assays for compounds that are useful for inhibiting the growth of a vertebrate, preferably mammalian, more preferably human, preneoplastic or neoplastic cell that abnormally expresses MN protein. Said screening assays comprise tests for the inhibition of the enzymatic activity of MN by said compounds. Additional assays provided herein test said compounds for their cell membrane impermeance.

Aspects of the instant invention disclosed herein are described in more detail below.

References

The following references are cited throughout the application by numbers in italics keyed to the list below:
1. Abbate et al., *J. Med. Chem.*, 45: 3583-3587 (2002).
2. Abbate et al., *J. Enz. Inhib. Med. Chem.*, 18: 303-308 (2003a).
3. Abbate et al., *Bioorg. Med. Chem. Lett.*, 13: In Press (2003b).
4. Abdine et al., *J. Assoc. Off. Anal. Chem.*, 61: 695-701 (1978).
5. Aldred et al., *Biochemistry*, 30: 569-575 (1991).
6. Balaban et al., "Pyrylium Salts: Syntheses, Reactions and Physical Properties," In *Advances in Hetercyclic Chemistry*, Katritzky, A. R., Ed., Academic Press, New York, pp. 8-360 (1982).
7. Barlow et al., *Nucl. Acids Res.*, 15: 2386 (1987).
8. Bartosova et al., *J. Pathol.*, 197: 314-321 (2002).
9. Bayer, A., *Ber. Dtsch. Chem. Ges.*, 43: 2337-2349 (1910).
10. Bayer and Piccard, Liebigs *Ann. Chem.*, 384: 208-223 (1911).
11. Beasley et al., *Cancer Res.*, 61: 5262-5267 (2001).
12. Behravan et al., *Eur. J. Biochem*, 190: 351-357 (1990).
13. Borras et al., *Bioorg. Med. Chem.*, 7: 2397-2406 (1999).
14. Briganti et al., *Biochemistry*, 36: 10384-10392 (1997).
15. Briganti et al., *Inorg. Chim. Acta.*: 275-276, 295-300 (1998).
16. Brown, J. M., "Exploiting the hypoxic cancer cell: mechanisms and therapeutic strategies," *Molecular Medicine Today*, 6: 157-162 (April 2000).
17. Casini et al., *J. Med. Chem.*, 43: 4884-4892 (2000).
18. Casini et al., *Curr. Cancer Drug Targets*, 2: 55-75 (2002).
19. a) Casini et al., *Bioorg. Med. Chem. Lett.*, 13: 841-845 (2003)
    b) Casini et al., *Biorg. Med. Chem. Lett.*, 13: 2763-2769 (2003).
20. Chegwidden et al., "The Roles of carbonic anhydrase isozymes in cancer," *Gene Families: Studies of DNA, RNA, Enzymes and Proteins*, Xue et al., Eds., World Scientific, Singapore, pp. 157-169 (2001).
21. Chia et al., *J. Clin. Oncol.*, 19: 3660-3668 (2001).
22. Chirica et al., *Biochim. Biophys. Acta*, 1544: 55-63 (2001).
23. Clare and Supuran, *Eur. J. Med., Chem.*: 32: 311-319 (1997).
24. Clare and Supuran, *Eur. J. Med. Chem.*, 34: 463-474 (1999).
25. Cuthbert et al., *J. Physiol.*, 551 (Pt.1) 79-92, (2003).
26. Dinculescu and Balaban, *Rev. Roum. Chem.*, 25: 1505-1528 (1980).
27. Dodgson et al., *The Carbonic Anhydrases*, Plenum Press, New York-London, pp. 398 (1991).
28. Doege et al., *J. Biol. Chem.*, 266: 894-902 (1991).
29. Elleby et al., *Eur. J. Biochem.*, 268: 1613-1619 (2001).
30. Ferraroni et al., Biochemistry, 41: 6237-6244 (2002a).
31. Ferraroni et al., Inorg. Chim. Acta, 339: 135-144 (2002b).
32. Fleming et al., *J. Clin. Invest.*, 96: 2907-2913 (1995).
33. Franchi et al., *J. Enz. Inhib. Med. Chem.*, 18: 333-338 (2003).
34. Geers and Gros, *Physiol. Rev.* 80:681-715 (2000).
35. Giatromanolaki et al., *Cancer Res.*, 61: 7992-7998 (2001).
36. Gomaa, Z. S., *Biomed. Chromatogr.*, 7: 134-135 (1993).
37. Gruneberg et al., *Angew. Chem. Int. Ed.*, 40: 389-393 (2001).
38. Hakansson et al., *J. Mol. Biol.*, 227: 1192-1204 (1992).
39. Heming et al., *J. Appl. Physiol.*, 61: 1849-1856 (1986).
40. Hewett-Emmett, D., "Evolution and distribution of the carbonic anhydrase gene families," In *The Carbonic Anhydrases—New Horizons*, Chegwidden et al., Eds., Birkhauser Verlag: Basel, Switzerland, pp. 29-78 (2000).
41. Höckel and Vaupel, *J. Natl. Cancer Inst.*, 93: 266-276 (2001).
42. Ilies et al., *Bioorg. Med. Chem.*, 8: 2145-2155 (2000).
43. Ilies et al., *J. Med. Chem.*, 46: 2187-2196 (2003).
44. Khalifah, R. G., *J. Biol. Chem.*, 246: 2561-2573 (1971).
45. Khalifah et al., *Biochemistry*, 16: 2241-2247 (1977).
46. Kim et al., *J. Am. Chem. Soc.*, 122: 12125-12134 (2000).
47. Kim et al., *J. Am. Chem. Soc.*, 123: 9620-9627 (2001).
48. Koukourakis et al., *Clin. Cancer Res.*, 7: 3399-3403 (2001).
49. Krungkrai et al., *Int. J. Parasitol.*, 31: 661-668 (2001).
50. Liao et al., *Am. J. Pathol.*, 145: 598-609 (1994).
51. Liao et al., *Cancer Res.*, 57: 2827-2831 (1997).
52. Lieskovska et al., *Neoplasma*, 46: 17-24 (1999).
53. Lindskog and Coleman, *Proc. Natl. Acad. Sci.* (USA) 70: 2505-2508 (1964).
54. Lindskog et al., "Structure-function relations in human carbonic anhydrase II as studied by site-directed mutagenesis," in *Carbonic anhydrase—From biochemistry and genetics to physiology and clinical medicine*, Botre et al., Eds., VCH, Weinheim, pp. 1-13 (1991)].
55. Lloyd et al., *Genes. Dev.*, 1: 594-602 (1987).
56. Loncaster et al., *Cancer Res.*, 61: 6394-6399 (2001).
57. Maren, T. H., *Physiol. Rev.*, 47: 595-781 (1967).
58. Maren, T. H., "Benzolamide—a renal carbonic anhydrase inhibitor," In *Orphan Drugs*, Karch, T. E., Ed., M. Dekker, New York, pp. 89-115 (1982).
59. Maren et al., *Mol. Pharmacol.*, 44: 901-906 (1993).
60. Maren et al., *J. Pharmacol. Exp. Ther.*, 280: 98-104 (1997).
61. Mendelsohn and Lippman, "Growth Factors," pp. 114-133, IN: DeVita et al. (eds.), *Cancer: Principles and Practice of Oncology* (4$^{th}$ Ed.; Lippincott; Philadelphia, 1993).
62. Mincione et al., *Eur. J. Pharm. Sci.*, 9: 185-199 (1999).
63. Montgomery et al., *Nucl. Acids. Res.*, 15: 4687 (1987).
64. Mori et al., *Gastroenterol.*, 105: 820-826 (1993).
65. Okuyama et al., *PNAS* (USA) 89: 1315-1319 (1992).
66. Opavsky et al., *Genomics*, 33: 480-487 (1996).
67. Owa and Nagasu, *Exp. Opin. Ther. Patents*, 10: 1725-1740 (2000).
68. Owa et al., *J. Med. Chem.*, 42: 3789-3799 (1999).
69. Parkkila et al., *Gut*, 35: 646-650 (1994).
70. Parkkilla et al., *Histochem. J.*, 27: 133-138 (1995).
71. Parkkila et al., *Hepatology*, 24: 104 (1996).
72. Pastorek et al., *Oncogene*, 9: 2788-2888 (1994).
73. Pastorekova et al., *Virology*, 187: 620-626 (1992).
74. Pastorekova et al., *Gastroenterology*, 112: 398-408 (1997).
75. Pearson and Lipman, *PNAS* (USA), 85: 2444 (1988).
76. Pocker and Stone, *Biochemistry*, 6: 668-678 (1967).
77. Scozzafava and Supuran, *Bioorg. Med. Chem. Lett.*, 10: 1117-1120 (2000).
78. Scozzafava et al., *Curr. Med. Chem.*, 10: 925-953 (2003).
79. Scozzafava et al., *J. Med. Chem.*, 42: 2641-2650 (1999).
80. Scozzafava et al., *J. Med. Chem.*, 42: 3690-3700 1999)
81. Scozzafava et al., *J. Med. Chem.*, 43: 292-300 (2000).
82. Sly and Hu, *Annu. Rev. Biochem.*, 64: 375-401 (1995).
83. Smith and Ferry, *FEMS Microbiol. Rev.*, 24: 335-366 (2000).

84. Steiner et al., *Eur. J. Biochem.*, 59: 253-259 (1975).
85. Sterling et al., *Am. J. Physiol.-Cell Physiol.*, 283: C1522-C1529 (2002).
86. Stubbs et al., *Mol. Med. Today*, 6: 15-19 (2000).
87. Supuran, C. T., *Opin. Investig. Drugs*, 12: 283-287 (2003).
88. Supuran and Clare, *Eur. J. Med. Chem.*, 30: 687-696 (1995).
89. Supuran and Clare, *Eur. J. Med. Chem.*, 33: 489-500 (1998).
90. Supuran and Clare, *Eur. J. Med. Chem.*, 34: 41-50 (1999).
91. Supuran and Scozzafava, *J. Enzyme Inhib.*, 15: 597-610 (2000a).
92. Supuran and Scozzafava, *Eur. J. Med. Chem.*, 35: 867-874 (2000b).
93. Supuran and Scozzafava, *Exp. Opin. Ther. Patents*, 10: 575-600 (2000c).
94. Supuran and Scozzafava, *Curr. Med. Chem.-Imm., Endoc. Metab. Agents*, 1: 61-97 (2001).
95. Supuran and Scozzafava, *Exp. Opin. Ther. Patents*, 12: 217-242 (2002).
96. Supuran et al., *Eur. J. Med. Chem.*, 33: 577-594 (1998a).
97. Supuran et al., *Eur. J. Med. Chem.*, 33: 739-752 (1998b).
98. Supuran et al., *J. Enz. Inhib.*, 15: 381-401 (2000a).
99. Supuran et al., *J. Med. Chem.*, 35: 309-321 (2000b).
100. Supuran et al., *Bioorg. Med. Chem.*, 9: 703-714 (2001a).
101. Supuran et al., *Curr. Med. Chem.-Imm., Endoc. Metab. Agents*, 1: 61-97 (2001b)
102. Supuran et al., *Med. Res. Rev.*, 23: 146-189 (2003).
103. Svastova et al., *Experimental Cell Research*, 290: 332-345, (2003).
104. Symington, *J. Biol. Chem.*, 267: 25744 (1992).
105. Tashian, R. E., *Adv. in Genetics*, 30: 321-356 (1992).
106. Teicher et al., *Anticancer Research*, 13: 1549-1556 (1993).
107. Tinker et al., *J. Pharmacol. Exp. Ther.*, 218: 600-607 (1981).
108. Toma and Balaban, *Tetrahedron, Suppl.* 7: 27-34 (1966).
109. Trinh et al., *Cancer Res.*, 55: 4808-4812 (1995).
110. Turner, et al., *Hum. Pathol.*, 28: 740-744 (1997).
111. Turner et al., *Br. J. Cancer*, 86: 1276-1282 (2002).
112. Uemura et al. [*J. Urology*, 1571 (4 Supp.): 377 (Abstract 1475) (Apr. 16, 1997)]
113. Vermylen et al., *Eur. Respir. J.*, 14: 806-811 (1999);
114. Vullo et al., *Bioorg. Med. Chem. Lett.*, 13: 1005-1009 (2003a).
115. Vullo et al. *J. Enz. Inhib. Med. Chem.*, 18: 403-406 (2003b).
116. Wingo et al., *Biochem. Biophys. Res. Comm.*, 288: 666-669 (2001).
117. Winum et al., *J. Med. Chem.*, 46: 2197-2204 (2003).
118. Wistrand and Lindqvist, "Design of carbonic anhydrase inhibitors and the relationship between the pharmacodymanics and pharmacokinetics of acetazolamide," In *Carbonic Anhydrase—FromBiochemistry and Genetics to Physiology and Clinical Medicine*, Botrè et al., Eds., VCH, Weinheim, pp. 352-378 (1991).
119. Workman and Straford, *Cancer and Metastasis Reviews*, 12: 73-82 (1993)
120. Wu et al., *J. Membr. Biol.* 162: 31-38 (1998).
121. Wykoff et al., *Cancer Research*, 60: 7075-7083 (2000).
122. Wykoff et al., *Am. J. Pathol.*, 158: 1011-1019(2001).
123. Zavada et al., *Int. J. Cancer*, 54: 268-274 (1993).

Abbreviations

The following abbreviations are used herein:
aa—amino acid
AAZ—acetazolamide
ATCC—American Type Culture Collection
bp—base pairs
BRL—Bethesda Research Laboratories
BRZ—brinzolamide
BSA—bovine serum albumin
CA—carbonic anhydrase
CAI—carbonic anhydrase inhibitor
CAM—cell adhesion molecule
CARP—carbonic anhydrase related protein
Ci—curie
cm—centimeter
CNS—central nervous system
cpm—counts per minute
C-terminus—carboxyl-terminus
° C.—degrees centigrade
DCP—dichlorophenamide
DEAE—diethylaminoethyl
DMEM—Dulbecco modified Eagle medium
ds—double-stranded
DZA—dorzolamide
EDTA—ethylenediaminetetraacetate
EZA—ethoxzolamide
F—fibroblasts
FCS—fetal calf serum
FITC—fluorescein isothiocyanate
H—HeLa cells
IC—intracellular
kb—kilobase
kbp—kilobase pairs
kd or kDa—kilodaltons
$K_I$—inhibition constant
KS—keratan sulphate
LTR—long terminal repeat
M—molar
mA—milliampere
MAb—monoclonal antibody
ME—mercaptoethanol
MEM—minimal essential medium
min.—minute(s)
mg—milligram
ml—milliliter
mM—millimolar
MMC—mitomycin C
mmol—millimole
MZA—methazolamide
N—normal concentration
NEG—negative
ng—nanogram
nm—nanometer
nM—nanomolar
nt—nucleotide
N-terminus—amino-terminus
ODN—oligodeoxynucleotide
ORF—open reading frame
PA—Protein A
PBS—phosphate buffered saline
PCR—polymerase chain reaction
PG—proteoglycan
pI—isoelectric point
PMA—phorbol 12-myristate 13-acetate POS—positive
Py—pyrimidine
QAS—quaternary ammonian sulfonilamide
QSAR—quantitative structure-activity relationship(s)
RACE—rapid amplification of cDNA ends
RCC—renal cell carcinoma
RIA—radioimmunoassay
RIP—radioimmunoprecipitation
RIPA—radioimmunoprecipitation assay
RNP—RNase protection assay
RT-PCT—reverse transcription polymerase chain reaction
SAC—*Staphylococcus aureus* cells
SAR—structure-activity relationship
sc—subcutaneous
SDS—sodium dodecyl sulfate
SDS-PAGE—sodium dodecyl sulfate-polyacrylamide gel electrophoresis
SINE—short interspersed repeated sequence
SP—signal peptide
SP-RIA—solid-phase radioimmunoassay
TBE—Tris-borate/EDTA electrophoresis buffer
TC—tissue culture
TCA—trichloroacetic acid
TC media—tissue culture media
TC—tissue culture
tk—thymidine kinase
TM—transmembrane
Tris—tris (hydroxymethyl) aminomethane
µCi—microcurie
µg—microgram
µl—microliter
µM—micromolar Cell Lines BL21 (DE3)—*Escherichia coli* strain described by Lindskog's group (for CA I, II expression)[Lindskog et al., "Structure-function relations in human carbonic anhydrase II as studied by site-directed mutagenesis," in *Carbonic anhydrase—From biochemistry and genetics to physiology and clinical medicine*, Botre et al., Eds., VCH, Weinheim, pp. 1-13 (1991)]
BL21-GOLD—*Escherichia coli* strain (from Stratagene) used for CA IX
(DE3) expression)

Nucleotide and Amino Acid Sequence Symbols

The following symbols are used to represent nucleotides herein:

| Base Symbol | Meaning |
|---|---|
| A | adenine |
| C | cytosine |
| G | guanine |
| T | thymine |
| U | uracil |
| I | inosine |
| M | A or C |
| R | A or G |
| W | A or T/U |
| S | C or G |
| Y | C or T/U |
| K | G or T/U |
| V | A or C or G |

| Base Symbol | Meaning |
|---|---|
| H | A or C or T/U |
| D | A or G or T/U |
| B | C or G or T/U |
| N/X | A or C or G or T/U |

There are twenty main amino acids, each of which is specified by a different arrangement of three adjacent nucleotides (triplet code or codon), and which are linked together in a specific order to form a characteristic protein. A three-letter or one-letter convention is used herein to identify said amino acids, as, for example, in FIG. 1 as follows:

| Amino acid name | 3 Ltr. Abbrev. | 1 Ltr. Abbrev. |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown or other | | X |

BRIEF DESCRIPTION OF THE FIGURES

FIGS. 1A-C provides the nucleotide sequence for MN/CA IX full-length cDNA [SEQ ID NO: 1]. FIGS. 1A-C also sets forth the predicted amino acid sequence [SEQ ID NO: 2] encoded by the cDNA.

FIGS. 2A-F provides a 10,898 bp complete genomic sequence of MN/CA9 [SEQ ID NO: 3]. The base count is as follows: 2654 A; 2739 C; 2645 G; and 2859 T. The 11 exons are in general shown in capital letters, but exon 1 is considered to begin at position 3507 as determined by RNase protection assay.

FIG. 3 provides an exon-intron map of the human MN/CA9 gene. The positions and sizes of the exons (numbered, cross-hatched boxes), Alu repeat elements (open boxes) and an LTR-related sequence (first unnumbered stippled box) are adjusted to the indicated scale. The exons corresponding to individual MN/CA IX protein domains are enclosed in dashed frames designated PG (proteoglycan-like domain), CA (carbonic anhydrase domain), TM (transmembrane anchor) and IC (intracytoplasmic tail). Below the map, the alignment of amino acid sequences illustrates the extent of homology between the MN/CA IX protein PG region (aa 53-111) [SEQ ID NO: 4] and the human aggrecan (aa 781-839) [SEQ ID NO: 5].

FIGS. 4 A-B shows the chemical structures of the 26 different sulfonamide compounds tested in Example 1.

FIG. 5 shows the scheme for the general synthesis of compounds 71-91 of Example 3 (Scheme 1).

FIG. 6 shows the scheme for the reaction between a pyrylium salt and an amine (Scheme 2), as described in Example 3.

DETAILED DESCRIPTION

The novel methods of the present invention comprise inhibiting the growth of tumor cells which overexpress MN protein with compounds that inhibit the enzymatic activity of MN protein. Said compounds are organic or inorganic, preferably organic, more preferably sulfonamides. Still more preferably, said compounds are pyridinium derivatives of aromatic or heterocyclic sulfonamides. These preferred pyridinium derivatives of sulfonamides are likely to have fewer side effects than other compounds in three respects: they are small molecules, they are membrane-impermeant, and they are specific potent inhibitors of the enzymatic activity of the tumor-associated MN/CA IX protein.

The use of oncoproteins as targets for developing new cancer therapeutics is considered conventional by those of skill in the art. [See, e.g., Mendelsohn and Lippman [61]. However, the application of such approaches to MN is new. In comparison to other tumor-related molecules (e.g. growth factors and their receptors), MN has the unique property of being differentially expressed in preneoplastic/neoplastic and normal tissues, which are separated by an anatomic barrier.

The pyridinium derivatives of sulfonamides of the present invention can be formed, for example, by creating bonds between pyrylium salts and aromatic or heterocyclic sulfonamide reagents, as described below. The aromatic or heterocyclic sulfonamide portion of a pyridinium salt of a sulfonamide compound can be called the "head," and the pyridinium portion can be called the "tail."

It can be appreciated by those of skill in the art that various other types of linkages can couple the pyridinium portion with the sulfonamide portion. It can further be appreciated that alternate methods, in addition to those disclosed herein, can be used to make the pyridinium derivatives of the present invention.

As used herein, "cancerous" and "neoplastic" have equivalent meanings, and "precancerous" and "preneoplastic" have equivalent meanings.

As used herein, the term "aromatic" when applied to sulphonamide structures means "comprising an aromatic ring, without an additional heterocyclic ring." The term "heterocyclic" when applied to sulphonamide structures means "comprising a heterocyclic ring, with or without an additional aromatic ring."

As used herein, the term "alkyl", alone or in combination, refers to a straight-chain or branched-chain alkyl radical containing from 1 to 12, preferably from 1 to 6 and more preferably from 1 to 4, carbon atoms. Examples of such radicals include, but are not limited to, methyl, ethyl, n-propyl, isopropyl, n-butyl, isobutyl, sec-butyl, tert-butyl, pentyl, isoamyl, hexyl, decyl and the like.

The term "aryl", alone or in combination, means a phenyl or naphthyl radical which optionally carries one or more substituents selected from alkyl, alkoxy, halogen, hydroxy, amino, nitro, cyano, haloalkyl, carboxy, alkoxycarbonyl, cycloalkyl, heterocycloalkyl, amido, mono and dialkyl substituted amino, mono and dialkyl substituted amido and the like, such as phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-I-naphthyl, 2-methyl-3-amino-1-naphthyl, 6-amino-2-naphthyl, 4,6-dimethoxy-2-naphthyl and the like.

Preferred sulfonamides of the present invention are aromatic and heterocyclic sulfonamides. The structures of representative sulfonamides of this group, designated 1-26, are shown in FIG. 4.

More preferred sulfonamides of the present invention are pyridinium derivatives of aromatic sulfonamides and have the general formula (A) below,

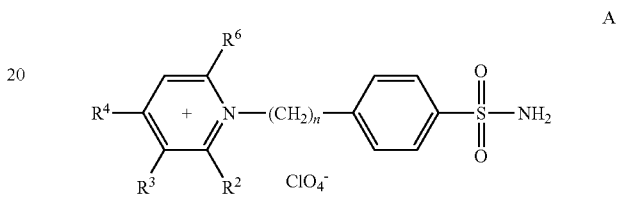

A wherein n is 0, 1, or 2; and R2, R3, R4 and R6 are each independently selected from the group consisting of hydrogen, alkyls and aryls. The structures of representative sulfonamides of this group, designated 27 through 70, are shown as derivatives of the general structure (A), in Table 2.

Alternatively, more preferred sulfonamides of the present invention are pyridinium derivatives of heterocyclic sulfonamides and have the general formula (B) below, wherein said pyridinium derivative of a heterocyclic sulfonamide has the general formula of:

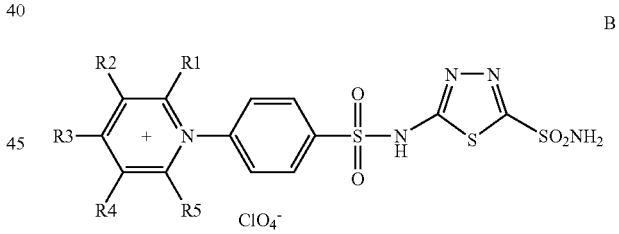

B wherein R1, R2, R3, R4 and R5 are each independently selected from the group consisting of hydrogen, akyls and aryls. The structures of representative sulfonamides of this group, designated 71 through 91, are shown as derivatives of the general structure (B), in Table 3.

Representative sulfonamide derivatives of the group of compounds represented by the general formulas (A) and (B) have CA IX inhibitory activity, and are potentially useful therapeutically as anticancer agents in treating MN-associated tumors.

Further, biologic activity of the identified sulfonamides will be tested in vitro by inhibition of the carbonic anhydrase enzymatic activity of the MN protein, by effects on cell morphology and growth characteristics of MN-related tumor cells (HeLa) and of control cells [104]. In vivo screening will be carried out in nude mice that have been injected with HeLa cells.

Representative Sulfonamide Inhibitors of CA IX

The sulfonamides investigated in Example 1 for the inhibition of the tumor-associated isozyme CA IX, of types 1-26 are shown in FIGS. 4A-B. Compounds 1-6, 11-12, 20 and 26 are commercially available, whereas 7-10 [43], 13-19 [24, 90, 97] and 21-25 [79] were prepared as reported earlier. The six clinically used compounds were also assayed. For Example 2 compounds (pyridinium derivatives of aromatic sulfonamides), reaction of sulfanilamide, homosulfanilamide or 4-(2-aminoethyl)-benzenesulfonamide with 2,6-di-, 2,4,6-tri- or 2,3,4,6-tetrasubstituted pyrylium salts afforded the pyridinium salts 27-70 investigated here, by the general Bayer-Piccard synthesis [9,10, 97].

As described in Example 3, a series of positively-charged sulfonamides, designated here as compounds 71-91, were obtained by reaction of aminobenzolamide (5-(4-aminobenzenesulfonylamino)-1,3,4-thiadiazole-2-sulfonamide) with tri-/tetra-substituted pyrylium salts possessing alkyl-, aryl- or combinations of alkyl and aryl groups at the pyridinium ring (described below). Three of these compounds (71, 75, and 87) have been described elsewhere [25, 85]; all other compounds of this series are new.

Heterocyclic Sulfonamide Inhibitors of CA IX:
Synthesis of Pyridinium Derivatives of
Aminobenzolamide Chemistry: Reaction of aminobenzolamide (5-(4-aminobenzenesulfonylamino)-1,3,4-thiadiazole-2-sulfonamide) [97] with 2,6-di-, 2,4,6-tri- or 2,3,4,6-tetrasubstituted pyrylium salts afforded the pyridinium salts 71-91 investigated here, by the general synthesis of such derivatives with nucleophiles (Scheme 1 as shown in FIG. 5) [6, 26, 108].

Preparation of compounds: A large number of positively-charged sulfonamides, prepared by reaction of amino-sulfonamides with pyrylium salts [23, 88, 89] were recently reported by this group, and generally tested as inhibitors of the "classical" isozymes CA I, II and IV [81, 96, 97, 98]. Based on QSAR studies on several series of CA inhibitors, including some positively-charged derivatives [23, 88, 89], it emerged that the enhancement of CA inhibitory activity is correlated with increased positive charges on the heterocyclic/aromatic ring incorporated in such molecules, as well as with "long" inhibitor molecules per se (i.e., molecules extending on the direction passing through the Zn(II) ion of the enzyme, the sulfonamide nitrogen atom and the long axis of the inhibitor) [23, 88, 89]. It appeared thus of interest to try to explore this result, designing positively-charged, long sulfonamide CAIs. Thus, we thought of attaching substituted-pyridinium moieties to an already potent and long-molecule CAI suitable for reaction with pyrylium salts, i.e., aminobenzolamide [97]. Indeed, this compound acts as a very potent CAI against isozymes I, II and IV (with inhibition constants in the low nanomolar range—see later in the text). The substitution pattern of the pyridinium ring was previously shown [81, 96, 97, 98] to be critical for the biological activity of this type of sulfonamide CAIs. Thus, a large series of of 2,4,6-trialkylpyridinium-; 2,6-dialkyl-4-phenylpyridinium-; 2-alkyl-4,6-diphenylpyridinium-; 2,4,6-triphenylpyridinium-, together with various 2,6-disubstituted-pyridinium and 2,3,5,6-tetrasubstituted-pyridinium aminobenzolamide derivatives have been prepared by the reaction described in Scheme 1 (Shown in FIG. 5).

Although apparently simple, the reaction between a pyrylium salt and an amine, leading to pyridinium salts, is in reality a complicated process (Scheme 2, shown in FIG. 6), as established by detailed spectroscopic and kinetic data from Balaban's and Katritzky's groups [6, 26, 108]. Thus, the nucleophilic attack of a primary amine $RNH_2$ on pyrylium cations generally occurs in the α position, with the formation of intermediates of type IV (depicted in FIG. 6), which by deprotonation in the presence of bases lead to the 2-amino-tetradehydropyran derivatives V. In many cases the deprotonation reaction is promoted by the amine itself, when this is basic enough (this being the reason why in many cases one works at molar ratios pyrylium:amine of 1:2 when pyridinium salts are prepared by this method), or by external catalysts added to the reaction mixture, such as triethylamine [6, 26, 108].The derivatives V are generally unstable, being tautomers with the ketodieneamines VI which are the key intermediates for the conversion of pyryliums into pyridiniums [6, 26, 108]. In acidic media, in the rate-determining step of the whole process, ketodieneamines VI may be converted to the corresponding pyridinium salts VII, although other products, such as vinylogous amides with diverse structures have also been isolated in such reactions [6, 26, 108]. A supplementary complication appears when the moiety substituting the 2- and/or 6-position(s) of the pyrylium ring is methyl, cases in which a concurrent cyclisation with formation of the anilines VIII in addition to the pyridinium salts VII, may take place too [6, 26, 108]. These concurrent reactions mentioned above are generally important when the amine to be converted into the pyridinium salt possesses weak nucleophilicity or basicity. This happens to be the case of aminobenzolamide. In fact, reaction of aminobenzolamide with several pyrylium salts, performed in a variety of conditions (different solvents, such as low molecular weight alcohols (MeOH, EtOH, i-PrOH); DMF; methylene chloride; acetonitrile; diverse molar ratios of the reagents; temperatures from 25 to 150° C.; reaction times between 15 min and 48 hours, etc) led only to the isolation of the unreacted raw materials. The only conditions which led to the formation of the pyridinium salts III (depicted in FIG. 5) were the following: anhydrous methanol in the presence of acetic anhydride as solvent and triethylamine as catalysts for the deprotonation of the intermediates IV. Acetic anhydride had the role of reacting with the water formed in the condensation reaction. This water may in fact act as a competitive nucleophile with aminobenzolamide when reacting with the pyrylium cation, and as a consequence the yields in pyridinium salts would dramatically be decreased. After the rapid formation of the ketodieneamine, catalyzed by triethylamine (and in the presence of the acetic anhydride as water scavenging agent), the cyclisation to the pyridinium ring (the rate-determining step) has been achieved by refluxation in the presence of acetic acid (2-5 hours). Still the yields were not always good, especially for the 2-methyl-containing derivatives.

Preparation of MN Proteins and/or Polypeptides

The terms "MN/CA IX" and "MN/CA9" are herein considered to be synonyms for MN. Also, the G250 antigen is considered to refer to MN protein/polypeptide [112].

Zavada et al., WO 93/18152 and/or WO 95/34650 disclose the MN cDNA sequence shown herein in FIGS. 1A-1C [SEQ ID NO: 1], the MN amino acid sequence [SEQ ID NO: 2] also shown in FIGS. 1A-1C, and the MN genomic sequence [SEQ ID NO: 3] shown herein in FIGS. 2A-2F. The MN gene is organized into 11 exons and 10 introns.

The first thirty seven amino acids of the MN protein shown in FIGS. 1A-1C is the putative MN signal peptide [SEQ ID NO: 6]. The MN protein has an extracellular domain [amino acids (aa) 38-414 of FIGS. 1A-1C [SEQ ID NO: 7], a transmembrane domain [aa 415-434; SEQ ID NO: 8] and an intracellular domain [aa 435-459; SEQ ID NO: 9]. The extracellular domain contains the proteoglycan-like domain [aa 53-111: SEQ ID NO: 4] and the carbonic anhydrase (CA) domain [aa 135-391; SEQ ID NO: 5].

The phrase "MN proteins and/or polypeptides" (MN proteins/polypeptides) is herein defined to mean proteins and/or polypeptides encoded by an MN gene or fragments thereof. An exemplary and preferred MN protein according to this invention has the deduced amino acid sequence shown in FIG. 1. Preferred MN proteins/polypeptides are those proteins and/or polypeptides that have substantial homology with the MN protein shown in FIG. 1. For example, such substantially homologous MN proteins/polypeptides are those that are reactive with the MN-specific antibodies, preferably the Mab M75 or its equivalent. The VU-M75 hybridoma that secretes the M75 Mab was deposited at the ATCC under HB 11128 on Sep. 17, 1992.

A "polypeptide" or "peptide" is a chain of amino acids covalently bound by peptide linkages and is herein considered to be composed of 50 or less amino acids. A "protein" is herein defined to be a polypeptide composed of more than 50 amino acids. The term polypeptide encompasses the terms peptide and oligopeptide.

It can be appreciated that a protein or polypeptide produced by a neoplastic cell in vivo could be altered in sequence from that produced by a tumor cell in cell culture or by a transformed cell. Thus, MN proteins and/or polypeptides which have varying amino acid sequences including without limitation, amino acid substitutions, extensions, deletions, truncations and combinations thereof, fall within the scope of this invention. It can also be appreciated that a protein extant within body fluids is subject to degradative processes, such as, proteolytic processes; thus, MN proteins that are significantly truncated and MN polypeptides may be found in body fluids, such as, sera. The phrase "MN antigen" is used herein to encompass MN proteins and/or polypeptides.

It will further be appreciated that the amino acid sequence of MN proteins and polypeptides can be modified by genetic techniques. One or more amino acids can be deleted or substituted. Such amino acid changes may not cause any measurable change in the biological activity of the protein or polypeptide and result in proteins or polypeptides which are within the scope of this invention, as well as, MN muteins.

The MN proteins and polypeptides of this invention can be prepared in a variety of ways according to this invention, for example, recombinantly, synthetically or otherwise biologically, that is, by cleaving longer proteins and polypeptides enzymatically and/or chemically. A preferred method to prepare MN proteins is by a recombinant means. Particularly preferred methods of recombinantly producing MN proteins are described below. A representative method to prepare the MN proteins shown in FIG. 1 or fragments thereof would be to insert the full-length or an appropriate fragment of MN cDNA into an appropriate expression vector as exemplified in the Materials and Methods section.

MN Gene

FIGS. 1A-C provides the nucleotide sequence for a full-length MN cDNA clone [SEQ ID NO: 1] isolated as described in Zavada et al., WO 95/34650. FIGS. 2A-F provides a complete MN genomic sequence [SEQ ID NO: 3].

The ORF of the MN cDNA shown in FIG. 1 has the coding capacity for a 459 amino acid protein with a calculated molecular weight of 49.7 kd. The overall amino acid composition of the MN/CA IX protein is rather acidic, and predicted to have a pI of 4.3. Analysis of native MN/CA IX protein from CGL3 cells by two-dimensional electrophoresis followed by immunoblotting has shown that in agreement with computer prediction, the MN/CA IX is an acidic protein existing in several isoelectric forms with pIs ranging from 4.7 to 6.3.

The CA domain is essential for induction of anchorage independence, whereas the TM anchor and IC tail are dispensable for that biological effect. The MN protein is also capable of causing plasma membrane ruffling in the transfected cells and appears to participate in their attachment to the solid support. The data evince the involvement of MN in the regulation of cell proliferation, adhesion and intercellular communication.

Enzymatic Screening Assays

Assays are provided herein for the screening of compounds for inhibition of the enzymatic activity of the MN protein. Such assays comprise the incubation of said compound with said MN protein and with a substrate selected from the group consisting of saturated $CO_2$ and 4-nitrophenylacetate, preferably saturated $CO_2$, and determination of the inhibition constant $K_I$ of said compound, wherein said enzymatic activity of the MN protein is measured by the pH change of an indicator by stopped flow spectrophotometer.

Screening of representative heterocyclic and aromatic sulfonamides for inhibition of MN protein: From Example 1, it was found that the inhibition profile of isozyme CA IX is very different from that of the classical isozymes CA I and II (cytosolic) as well as CA IV (membrane-bound). The following particular features may be noted: (i) all the 32 sulfonamides investigated in Example 1 act as CA IX inhibitors, with inhibition constants in the range of 14-285 nM (the corresponding affinities for the other three isozymes vary in a much wider range, as seen from data of Table 1). Based on these data, it can be noted that CA IX is a sulfonamide avid CA, similarly to CA II, the isozyme considered up to now to be responsible for the majority of pharmacological effect of sulfonamides [22, 29, 83,93, 94, 95, 102]. Still, many other differences are observed between CA IX and other isozymes for which inhibitors were developed for clinical use; (ii) for CA I, II and IV, generally, aromatic sulfonamides behave as weaker inhibitors as compared to heterocyclic derivatives (compare 1-6, or DCP), as aromatic compounds, with 15,21, AAZ, MZA, EZA, DZA or BRZ among others (as heterocyclic sulfonamides). In the case of CA IX, such a fine distinction is rather difficult to be made, since both aromatic (such as 1, 6, 11, 12, 17, 18, 22-26) derivatives, as well as heterocyclic compounds (such as 14, 15, 21, and the clinically used sulfonamides—except dichlorophenamide) possess rather similar inhibition constants, in the range of 14-50 nM; (iii) orthanilamide derivatives (such as 1, 17 and 22) behave as very potent CA IX inhibitors ($K_I$-s in the range of 20-33 nM), although they are weak or medium-weak inhibitors of CA I, II and IV; (iv) 1,3-benzene-disulfonamide derivatives (such as 11, 12 and DCP) are again strong CA IX inhibitors, with $K_I$-s in the range of 24-50 nM, although their CA II, I and IV inhibition profile is not particularly strong; (v) metanilamide 2, sulfanilamide 3, and 4-hydrazino-benzenesulfonamide 4 show CA IX inhibition data quite similar with those against CA II, whereas homosulfanilamide 5 and 4-aminoethyl-benzensulfonamide 6 act as better CA IX inhibitors as compared to CA II inhibition; (vi) the halogenosulfanilamides 7-10 are much weaker inhibitors of CA IX than of CA II, a finding difficult to interpret at this moment; (vii) the strongest CA II inhibitor among the investigated compounds, 4-aminobenzolamide 15 ($K_I$ of 2 nM) is not the strongest CA IX inhibitor ($K_I$ of 38 nM). Instead, the best CA IX inhibitor detected so far is the ethoxzolamide phenol 21 ($K_I$ of 14 nM). It is interesting to note that 21 and EZA have the same affinity for CA II, whereas their affinity for CA IX is rather different, with the phenol more active than the ethoxy-derivative; (viii) among the clinically used compounds, the best inhibitor is acetazolamide, followed by methazolamide, ethoxzolamide and brinzolamide. The most ineffective (but appreciably inhibiting the isozyme IX) are dichlorophenamide and dorzolamide; (ix) sulfonamides 20 and 22-26 behave as very good CA IX inhibitors, with $K_I$-s in the range of 16-32 nM, being slightly more effective than the clinically used CAIs mentioned above, and among the best CA IX inhibitors detected so far. It is thus envisageable that such compounds may be used as lead molecules for obtaining more potent and eventually specific CA IX inhibitors, with applications as antitumor agents.

Screening of representative pyridinium derivatives of aromatic sulfonamides for inhibition of MN protein: From Example 2, wherein membrane-impermeant pyridinium derivatives of sulfonamides were tested for their ability to inhibit the enzymatic activity of CA IX, the following conclusions were drawn from data of Table 2: (i) for a given substitution pattern of the pyridinium ring, the 4-aminoethyl-benzenesulfonamide derivatives 55-70 were more active than the corresponding homosulfanilamide derivatives 39-54, which in turn were more active than the corresponding sulfanilamides 27-38. This behavior has also been observed for the other three investigated isozymes [96]; (ii) some of the derivatives possessing bulky substitutents at the pyridinium ring (mainly phenyls, tert-butyls; n-butyl, n-propyl or isopropyl), such as 34-37, 51 and 67, were very ineffective CA IX inhibitors, showing inhibition constants >500 nM; (iii) another group of compounds, including 27, 30-33, 44, and 60 showed a moderate inhibitory power towards the tumor-associated isozyme IX, showing $K_I$ values in the range of 160-450 nM. Most of these compounds are sulfanilamide derivatives (except 44 and 60), and the substitution pattern at the pyridinium ring includes (with one exception, 27) at least one phenyl group in 4, or two phenyls in the 2 and 4 positions. It should be noted that the corresponding homosulfanilamides and 4-aminoethylbenzene-sulfonamides incorporating the same substitution pattern as the compounds mentioned above (sulfanilamides), lead to much better CA IX inhibitors (see later in the text); (iv) a third group of derivatives, including 38, 45-50, 52, 53, 61, 63-66, 68 and 69, showed good CA IX inhibitory properties, with $K_I$ values in the range of 64-135 nM. As mentioned above, except for the tetramethyl-pyridinium-substituted derivative 38, most of these compounds incorporate 4-phenyl-pyridinium or 2,4-diphenylpyridinium moieties, whereas the group in position 6 is generally quite variable (alkyls or phenyl are tolerated). The most interesting observation regarding this subtype of CA IX inhibitors is constituted by the fact that the 2,4,6-triphenyl-pyridinium- and 2,6-diphenyl-pyridinium derivatives of homosulfanilamide and 4-aminoethylbenzenesulfonamide (52-53 and 68-69) efficiently inhibit isozyme IX, although they act as very weak inhibitors for isozymes I, II and IV (Table 2). As it will be discussed shortly, this may be due to the fact that the hCA IX active site is larger than that of the other investigated isozymes, notably CA II, I and IV; (v) a last group of derivatives (28-29; 39-43; 54; 55-59; 62 and 70) showed very good CA IX inhibitory properties, these compounds possessing $K_I$ values in the range of 6-54 nM, similarly to the clinically used inhibitors acetazolamide, methazolamide, dichlorophenamide and indisulam, for which the inhibition data are provided for comparison. It should be noted that three derivatives 58, 59 and 70 showed inhibition constants <10 nM, these being the most potent CA IX inhibitors ever reported up to now. Correlated with their membrane-impermeability [96, 85], it may be assumed that in vivo such compounds may lead for the first time to a selective CA IX inhibition. Thus, the best substitution pattern at the pyridinium ring includes either only compact alkyls (39-41, 54, 55 and 70), or 2,6-dialkyl-4-phenyl-pyridinium moieties (all compounds mentioned above except 62, which incorporates a 2-methyl-4,6-diphenylpyridinium ring); (vi) the number of the substituents at the pyridinium ring seems to be less important for the activity of this series of CAIs, since both di-, tri- or tetrasubstituted derivatives showed good inhibitory potency. The nature of these groups on the other hand—as discussed in detail above—is the most important parameter influencing CA inhibitory properties (together with the linker between the benzenesulfonamide moiety and the substituted pyridinium ring); (vii) the isozyme most similar to hCA IX regarding the affinity for these inhibitors was hCA II (which has 33% homology with hCA IX) [Pastorek et al. (1994), supra] whereas the affinities of isozymes I and IV were rather different.

Screening of representative Dyridinium derivatives of heterocyclic sulfonamides for inhibition of MN protein, and comparison with inhibition of other CA isozymes: Isozyme I. As seen from data of Table 3, all derivatives 71-91 reported here act as very efficient CAIs against this isozyme which is generally the most "resistant" to inhibitors of this type [30, 31, 100, 102]. Indeed, aminobenzolamide is already a highly potent CA I inhibitor ($K_I$ of 6 nM), whereas inhibitors 71-91 show inhibition constants in the range of 3-12 nM, in contrast to the clinically used sulfonamide CAIs which are much less effective inhibitors, with $K_I$ values in the range of 30-1200 nM (Table 3). Thus, derivatives possessing several bulky groups (i-Pr; t-Bu; n-Pr; n-Bu; Ph, etc) substituting the pyridinium moiety, such as 73, 74, 77, 78, 82, 84, 85 showed a decreased inhibitory activity as compared to aminobenzolamide, with $K_I$ values in the range of 7-12 nM (aminobenzolamide has a $K_I$ of 6 nM against hCA I). The rest of the compounds were more efficient as compared to aminobenzolamide in inhibiting this isozyme, with $K_I$ values in the range of 3-5 nM. Best CA I inhibitors were 75, and 89-91 ($K_I$ of 3 nM), all of which containing either only alkyl moieties or 4-Ph and other alkyl moieties substituting the pyridinium ring. These are probably the best CA I inhibitors ever reported up to now, since the clinically used CAIs show much higher inhibition constants against isozyme I (Table 3).

Isozyme II. Aminobenzolamide is already a very potent CA II inhibitor, with an inhibition constant around 2 nM. Several of the new inhibitors, such as 74, 77, 78, 82-88 act as weaker CA II inhibitors as compared to aminobenzolamide, with $K_I$ values in the range of 3.13-5.96 nM (but all these compounds act as potent inhibitors, being much more effective than the clinically used CAIs acetazolamide, methazolamide, dichlorophenamide or indisulam—see Table 3). Again the substitution pattern at the pyridinium ring is the main discriminator of activity for these compounds: all the less active derivatives mentioned above incorporate at least two bulky/long aliphatic groups, mainly in positions 2- and 6- of the pyridinium ring (n-Pr; t-Bu; n-Bu; and Ph). The best CA II inhibitors among derivatives 71-91 were those incorporating more compact 2,6-substituents at the pyridinium ring (such as Me, Et) together with a 4-Me or 4-Phe moiety, or those incorporating only aliphatic such groups, such as 71-73, 75, 76, 79-81, 89-91, which showed $K_I$ values in the range of 0.20-1.61 nM (thus, for the best inhibitors a factor of 10 increase in inhibitory power as compared to aminobenzolamide). It should be mentioned that iso-propyl-substituted compounds (73, 79) are active as CA II inhibitors, although their activity against CA I was not so good.

Isozyme IV. Most sulfonamides show inhibitory activity against CA IV intermediate between those towards CA I (less susceptible) and CA II (very high affinity for sulfonamides). This is also the trend observed with the sulfonamides investigated here, derivatives of aminobenzolamide. Thus, the parent sulfonamide (shown in FIG. 5) is a potent CA IV inhibitor, with a $K_I$ value around 5 nM. The new derivatives of general formula (B) incorporating bulky pyridinium-ring substituents (such as 74, 77, 78, 82, 84-88, 90) were less effective than aminobenzolamide, showing $K_I$ values in the range of 5.2-10.3 nM, whereas the compounds showing the other substitution pattern mentioned above were better CA IV inhibitors, showing $K_I$ values in the range of 2.0-4.7 nM.

Isozyme IX. Aminobenzolamide is less inhibitory against this isozyme ($K_I$ of 38 nM) as compared to other isozymes discussed above. This behavior is difficult to explain at this point, since no X-ray crystal structure of this isozyme has been reported. A very encouraging result obtained with the new derivatives of general formula (B) reported here, was the observation that several of them show very high affinity for CA IX, with $K_I$ values in the range of 3-9 nM (derivatives 71, 72, 75, 76, and 89). It may be seen that all of them incorporate aliphatic moieties (Me, Et and i-Pr) in positions 2- and 6- of the pyridinium ring, and either 4-Me or 4-Ph moieties. Only one compound is tetrasubstituted (89), again possessing only methyl moieties. The best CA IX inhibitor (and the best ever reported up to now) was 71, which is almost 13 times more effective than benzolamide in inhibiting this isozyme. Another group of new derivatives, such as 73, 74, 77, 79, 80, 81, 83, 86-88, 90, 91, showed effective CA IX inhibition, with $K_I$ values in the range of 12-35 nM, being thus more effective than aminobenzolamide. They incorporate slightly bulkier groups as compared to the previously discussed ones. Again the less effective inhibitors ($K_I$ values in the range of 40-43 nM) were those incorporating several bulky pyridinium substituents, such as 78, 84, 85 which contained either two n-Bu or one Ph and n-Bu/t-Bu in positions 2- and 6- of the pyridinium ring. Thus, SAR is now rather clear for this type of CAIs: best CA IX inhibitors should contain either only small, compact aliphatic moieties substituting the pyridinium ring, or they tolerate a 4-Ph moiety, but the 2,6-substituents should again be small, compact aliphatic moieties. In this particular case, 2,4,6-trisubstituted-pyridinium derivatives were more effective CA IX inhibitors as compared to the tetrasubstituted derivatives.

Membrane impermeability of Heterocyclic Sulfonamide Inhibitors of CA IX. As seen from data of Table 4 of Example 3, incubation of human red cells (which contain high concentrations of isozymes I and II, i.e., 150 μM hCA I and 20 μM hCA II, but not the membrane-bound CA IV or CA IX) [118] with millimolar concentrations of different sulfonamide inhibitors, such as acetazolamide, or methazolamide, led to saturation of the two isozymes present in erythrocytes with inhibitor, already after short periods of incubation (30 min), whereas for benzolamide or aminobenzolamide, a similar effect is achieved after somehow longer periods (60 min) (Table 4). This is obviously due to the high diffusibility through membranes of the first three inhibitors, whereas benzolamide/aminobenzolamide with a $pK_a$ of 3.2 for the second sulfonamido group [58] being present mainly as an (di)anion at the pH at which the experiment has been done (7.4), is already less diffusible and penetrates membranes in a longer time. Different cationic sulfonamides synthesized by us here, such as 71, 76, 89, 91, in the same conditions, were detected only in very small amounts within the blood red cells, proving that they were unable to penetrate through the membranes, obviously due to their cationic nature. Even after incubation times as long as one hour (and longer, data not shown), only traces of such cationic sulfonamides were present inside the blood red cells, as proved by the three assay methods used for their identification in the cell lysate, which were in good agreement with each other (Table 4). This demonstrates that the proposed approach for achieving membrane impermeability works well for the designed positively-charged sulfonamide CAIs of the general formula (B) (shown above), since the very small amount of sulfonamide detected may be due to contamination of the lysates with very small amount of membranes.

Design of Membrane-Impermeant Sulfonamide Inhibitors of CA IX

No X-ray crystal structure of isozyme IX is available up to now, in strong contrast with hCA II, for which many X-ray crystal structures are available (alone or in complexes with inhibitors and activators) [1, 2, 14, 15, 19a, 19b, 37, 38]. Examining the active site residues of these two isozymes and the architecture of hCA II, may help explain the above inhibition data and their relevance for CA IX specific inhibitors.

First of all, the zinc ligands and the proton shuttle residue of these two isozymes are identical [33, 43, 72, 100, 101, 102, 114, 115, 117]. An important difference is constituted by the amino acid in position 131, which is Phe for hCA II and Val for hCA IX. Phe 131 is known to be very important for the binding of sulfonamide inhibitors to hCA II [2, 46, 47]: in many cases this bulky side chain limits the space available for the inhibitor aromatic moieties, or it may participate in stacking interactions with groups present in it (for recent examples see refs. [2, 46, 47]. Thus, the presence of a less bulky such residue in hCA IX (i.e., a valine) which is also unavailable for participation to stacking interactions has as a consequence the fact that the hCA IX active site is larger than that of hCA II. A second potentially important residue is 132, which is Gly in hCA II and Asp in hCA IX. This residue is situated on the rim of the hydrophilic half of the entrance to the active site of hCA II (and presumably also of hCA IX) and it is critical for the interaction with inhibitors possessing elongated molecules, as recenly shown by us [19b]. Strong hydrogen bonds involving the CONH moiety of Gly 132 were shown to stabilize the complex of this isozyme with a p-aminoethylbenzene-sulfonamide derived inhibitor [19b]. In the case of hCA IX, the presence of aspartic acid in this position at the entrance of the active site may signify that: (i) stronger interactions with polar moieties of the inhibitor bound within the active site should be possible, since the COOH moiety possesses more donor atoms; (ii) this residue may have flexible conformations, fine-tuning in this way the interaction with inhibitors. Thus, the stronger hCA IX inhibition with some of these inhibitors (as compared to their affinity for isozyme II), such as for example 46-50, 52, 53, 55, 58, 62 and 68-70, might be explained just by the different interactions with the two active site residues mentioned above.

Therapeutic Use of MN-Specific Inhibitors

The MN-specific inhibitors of this invention, organic and/or inorganic, preferably organic, and as outlined above, may be used therapeutically in the treatment of neoplastic and/or pre-neoplastic disease, either alone or in combination with other chemotherapeutic drugs.

The MN-specific inhibitors can be administered in a therapeutically effective amount, preferably dispersed in a physiologically acceptable, non-toxic liquid vehicle.

Materials and Methods

General. Melting points: heating plate microscope (not corrected); IR spectra: KBr pellets, 400-4000 cm$^{-1}$ Perkin-Elmer 16PC FTIR spectrometer; $^1$H-NMR spectra: Varian 300CXP apparatus (chemical shifts are expressed as δ values relative to Me$_4$Si as standard); Elemental analysis: Carlo Erba Instrument CHNS Elemental Analyzer, Model 1106. All reactions were monitored by thin-layer chromatography (TLC) using 0.25-mm precoated silica gel plates (E. Merck). Pyrylium salts were prepared by literature procedures, generally by olefin (or their precursors) bisacylation, as described in the literature [6, 26, 108], whereas aminobenzolamide as described earlier [97]. Other sulfonamides used as standards were commercially available.

General Procedure for the Preparation of Compounds 71-91 (Pyridinium Derivatives of Aminobenzolamide)

An amount of 2.9 mM of aminobenzolamide [97] and 2.9 mM of pyrylium salt II (depicted in FIG. 5) were suspended in 5 mL of anhydrous methanol and poured into a stirred mixture of 14.5 mM of triethylamine and 5.8 mM of acetic anhydride. After five minutes of stirring, another 10 mL of methanol were added to the reaction mixture, which was heated to reflux for 15 min. Then 14.5 mM of acetic acid was added and heating was continued for 2-5 hours. The role of the acetic anhydride is to react with the water formed during the condensation reaction between the pyrylium salt and the aromatic amine, in order to shift the equilibrium towards the formation of the pyridinium salts of the general formula (B) (shown above). In the case of aminobenzolamide, this procedure is the only one which gave acceptable yields in pyridinium salts, probably due to the deactivating effect of the sulfamoylaminothiadiazole moiety on the amine group, which becomes poorly nucleophilic and unreactive towards these reagents. The precipitated pyridinium salts obtained were purified by treatment with concentrated ammonia solution (which also converts the eventually unreacted pyrylium salt to the corresponding pyridine which is soluble in acidic medium), reprecipitation with perchloric acid and recrystallization from water with 2-5% HClO$_4$.

Purification of Catalytic Domain of CA IX

The cDNA of the catalytic domain of hCA IX (isolated as described by Pastorek et al. [72]) was amplified by using PCR and specific primers for the vector pCAL-n-FLAG (from Stratagene). The obtained construct was inserted in the PCAL-n-FLAG vector and then cloned and expressed in *Escherichia coli* strain BL21-GOLD(DE3) (from Stratagene). The bacterial cells were lysed and homogenated in a buffered solution (pH 8) of 4 M urea and 2% Triton X-100, as described by Wingo et al. [116]. The homogenate thus obtained was extensively centrifuged in order to remove soluble and membrane associated proteins as well as other cellular debris. The resulting pellet was washed by repeated homogenation and centrifugation in water, in order to remove the remaining urea and Triton X-100. Purified CA IX inclusion bodies were denaturated in 6 M guanidine hydrochloride and refolded into the active form by snap dilution into a solution of 100 mM MES (pH 6), 500 mM L-arginine, 2 mM ZnCl$_2$, 2 mM EDTA, 2 mM reduced glutathione, 1 mM oxidized glutathione. Active hCA IX was extensively dialysed into a solution of 10 mM Hepes (pH 7.5), 10 mM Tris HCl, 100 mM Na$_2$SO$_4$ and 1 mM ZnCl$_2$. The amount of protein was determined by spectrophometric measurements and its activity by stopped-flow measurements, with CO$_2$ as substrate [44]. Optionally, the protein was further purified by sulfonamide affinity chromatography [44], the amount of enzyme was determined by spectrophometric measurements and its activity by stopped-flow measurements, with CO$_2$ as substrate [44].

CA I, II and IV Purification

Human CA I and CA II cDNAs were expressed in *Escherichia coli* strain BL21 (DE3) from the plasmids pACA/hCA I and pACA/hCA II described by Lindskog's group [54]. Cell growth conditions were those described in ref. [12], and enzymes were purified by affinity chromatography according to the method of Khalifah et al. [45]. Enzyme concentrations were determined spectrophotometrically at 280 nm, utilizing a molar absorptivity of 49 mM$^{-1}$.cm$^{-1}$ for CA I and 54 mM$^{-1}$.cm$^{-1}$ for CA II, respectively, based on $M_r$=28.85 kDa for CA I, and 29.3 kDa for CA II, respectively [53, 84]. CA IV was isolated from bovine lung microsomes as described by Maren et al, and its concentration has been determined by titration with ethoxzolamide [59].

Enzyme Assays

CA CO2 Hydrase Activity Assay

An SX.18MV-R Applied Photophysics stopped-flow instrument has been used for assaying the CA CO$_2$ hydration activity assays [44]. A stopped flow variant of the Poker and Stone spectrophotometric method [76] has been employed, using an SX.18MV-R Applied Photophysics stopped flow instrument, as described previously [43]. Phenol red (at a concentration of 0.2 mM) has been used as indicator, working at the absorbance maximum of 557 nm, with 10 mM Hepes (pH 7.5) as buffer, 0.1 M Na$_2$SO$_4$ (for maintaining constant the ionic strength), following the CA-catalyzed CO$_2$ hydration reaction for a period of 10-100 s. Saturated CO$_2$ solutions in water at 20° C. were used as substrate [44]. Stock solutions of inhibitor (1 mM) were prepared in distilled-deionized water with 10-20% (v/v) DMSO (which is not inhibitory at these concentrations) and dilutions up to 0.01 nM were done thereafter with distilled-deionized water. Inhibitor and enzyme solutions were preincubated together for 10 min at room temperature prior to assay, in order to allow for the formation of the E-I complex. Triplicate experiments were done for each inhibitor concentration, and the values reported throughout the paper are the mean of such results.

CA Esterase Activity Assay

Initial rates of 4-nitrophenylacetate hydrolysis catalysed by different CA isozymes were monitored spectrophotometrically, at 400 nm, with a Cary 3 instrument interfaced with an IBM compatible PC [76]. Solutions of substrate were prepared in anhydrous acetonitrile; the substrate concentrations varied between $2.10^{-2}$ and $1.10^{-6}$ M, working at 25° C. A molar absorption coefficient ε of 18,400 M$^{-1}$.cm$^{-1}$ was used for the 4-nitrophenolate formed by hydrolysis, in the conditions of the experiments (pH 7.40), as reported in the literature [76]. Non-enzymatic hydrolysis rates were always subtracted from the observed rates. Triplicate experiments were done for each inhibitor concentration, and the values reported throughout the paper are the mean of such results.

Stock solutions of inhibitor (1-3 mM) were prepared in distilled-deionized water with 10-20% (v/v) DMSO (which is not inhibitory at these concentrations) and dilutions up to 0.01 nM were done thereafter with distilled-deionized water. Inhibitor and enzyme solutions were preincubated together for 10 min at room temperature prior to assay, in order to allow for the formation of the E-I complex. The inhibition constant $K_I$ was determined as described in references [44, 76].

Membrane Permeance Assay: Ex vivo Penetration through Red Blood Cells

An amount of 10 mL of freshly isolated human red cells thoroughly washed several times with Tris buffer (pH 7.40, 5 mM) and centrifuged for 10 min were treated with 25 mL of a 2 mM solution of sulfonamide inhibitor. Incubation has been done at 37° C. with gentle stirring, for periods of 30-120 min. After the incubation times of 30, 60 and 120 min., respectively, the red cells were centrifuged again for 10 min, the supernatant discarded, and the cells washed three times with 10 mL of the above mentioned buffer, in order to eliminate all unbound inhibitor [81, 96, 98]. The cells were then lysed in 25 mL of distilled water, centrifuged for eliminating membranes and other insoluble impurities. The obtained solution was heated at 100° C. for 5 minutes (in order to denature CA-s) and sulfonamides possibly present have been assayed in each sample by three methods: a HPLC method [36]; spectrophotometrically [4] and enzymatically [76].

HPLC: A variant of the methods of Gomaa [36] has been developed by us, as follows: a commercially available 5 μm Bondapak C-18 column was used for the separation, with a mobile phase made of acetonitrile-methanol-phosphate buffer (pH 7.4) 10:2:88 (v/v/v), at a flow rate of 3 mL/min, with 0.3 mg/mL sulphadiazine (Sigma) as internal standard. The retention times were: 12.69 min for acetazolamide; 4.55 min for sulphadiazine; 10.54 min for benzolamide; 12.32 min for aminobenzolamide; 3.15 min for 71; 4.41 min for 76; 3.54 min for 89; and 4.24 min for 91. The eluent was monitored continuously for absorbance (at 254 nm for acetazolamide, and wavelength in the range of 270-310 nm in the case of the other sulfonamides.

Spectrophotometrically: A variant of the pH-induced spectrophotometric assay of Abdine et al. [4] has been used, working for instance at 260 and 292 nm, respectively, for acetazolamide; at 225 and 265 nm, respectively, for sulfanilamide, etc. Standardized solutions of each inhibitor have been prepared in the same buffer as the one used for the membrane penetrability experiments.

Enzymatically: the amount of sulfonamide present in the lysate has been evaluated based on hCA II inhibition measured with the esterase method, as described above [76]. Standard inhibition curves have been obtained previously for each sulfonamide, using the pure compound, which were used thereafter for determining the amount of inhibitor present in the lysate. Mention should be made that the three methods presented above led to results in good agreement, within the limits of the experimental errors.

Statistical analysis: Values are expressed±standard error of measurement. Statistical significance was determined using an unpaired t-test with p<0.05 considered significant.

The following examples are for purposes of illustration only and are not meant to limit the invention in any way.

EXAMPLE 1

Inhibition of the Tumor-Associated Isozyme IX with Aromatic and Heterocyclic Sulfonamides The inhibition of the tumor-associated transmembrane carbonic anhydrase IX (CA IX) isozyme has been investigated with a series of aromatic and heterocyclic sulfonamides, including the six clinically used derivatives acetazolamide, methazolamide, ethoxzolamide, dichlorophenamide, dorzolamide and brinzolamide. Inhibition data for the physiologically relevant isozymes I and II (cytosolic forms) and IV (membrane-bound) Were also provided for comparison.

Chemistry. Sulfonamides investigated for the inhibition of the tumor-associated isozyme CA IX, of types 1-26 are shown in FIGS. 4A-B. Compounds 1-6, 11-12, 20 and 26 are commercially available, whereas 7-10 [43], 13-19 [24, 79, 90, 97] and 21-25 [79] were prepared as reported earlier. The six clinically used compounds were also assayed, since no such data are available in the literature.

CA inhibition data. Inhibition data against four CA isozymes, CA I, II, IV and IX [44, 72, 116], with the above mentioned compounds 1-26 and the six clinically used inhibitors, are shown in Table 1.

TABLE 1

CA I, II, IV and IX inhibition data with sulfonamides 1–26 and clinically used inhibitors.

| Inhibitor | $K_I$* (nM) | | | |
|---|---|---|---|---|
| | hAG I[a] | hCA II[a] | bCA IV[b] | hCA IX[c] |
| 1 | 45400 | 295 | 1310 | 33 |
| 2 | 25000 | 240 | 2200 | 238 |
| 3 | 28000 | 300 | 3000 | 294 |
| 4 | 78500 | 320 | 3215 | 305 |
| 5 | 25000 | 170 | 2800 | 103 |
| 6 | 21000 | 160 | 2450 | 33 |
| 7 | 8300 | 60 | 180 | 245 |
| 8 | 9800 | 110 | 320 | 264 |
| 9 | 6500 | 40 | 66 | 269 |
| 10 | 6000 | 70 | 125 | 285 |
| 11 | 5800 | 63 | 154 | 24 |
| 12 | 8400 | 75 | 160 | 39 |
| 13 | 8600 | 60 | 540 | 41 |
| 14 | 9300 | 19 | 355 | 30 |
| 15 | 6 | 2 | 5 | 38 |
| 16 | 164 | 46 | 129 | 34 |
| 17 | 185 | 50 | 144 | 20 |
| 18 | 109 | 33 | 72 | 31 |
| 19 | 95 | 30 | 72 | 24 |
| 20 | 690 | 12 | 154 | 16 |
| 21 | 55 | 8 | 17 | 14 |
| 22 | 21000 | 125 | 415 | 32 |
| 23 | 23000 | 133 | 438 | 30 |
| 24 | 24000 | 125 | 560 | 21 |
| 25 | 18000 | 110 | 450 | 22 |
| 26 | 135 | 40 | 86 | 26 |
| AAZ | 250 | 12 | 70 | 25 |
| MZA | 50 | 14 | 36 | 27 |
| EZA | 25 | 8 | 13 | 34 |
| DCP | 1200 | 38 | 380 | 50 |
| DZA | 50000 | 9 | 43 | 52 |
| BRZ | — | 3 | 45 | 37 |

[a]Human cloned isozymes, esterase assay method [76];
[b]Isolated from bovine lung microsomes, esterase assay method [76];
[c]Human cloned isozyme, $CO_2$ hydrase assay method [44, 72, 116].

We report here the first inhibition study of the tumor-associated, transmembrane isozyme CA IX with a series of aromatic and heterocyclic sulfonamides, including also the six clinically used derivatives acetazolamide, methazolamide, ethoxzolamide, dichlorophenamide, dorzolamide and brinzolamide. Inhibition data for the physiologically relevant isozymes I and II (cytosolic forms) and IV (membrane-bound) are also provided for comparison. Very interesting inhibition profile against CA IX with these sulfonamides has been detected, which is a promising discovery for the potential design of CA IX-specific inhibitors, with applications as antitumor agents. Several nanomolar CA IX inhibitors have been detected, both among the aromatic (such as orthanilamide, homosulfanilamide, 4-carboxy-benzenesulfonamide, 1-naphthalene-sulfonamide and 1,3-benzenedisulfonamide derivatives) as well as the heterocyclic (such as 1,3,4-thiadiazole-2-sulfonamide, benzothiazole-2-sulfonamide, etc.) sulfonamides investigated.

EXAMPLE 2

The First Selective, Membrane-impermeant Inhibitors Targeting the Tumor-Associated Isozyme IX Up to now no CA IX inhibition studies with this type of membrane-impermeant CAIs have been reported. Thus, we decided to explore some of the pyridinium derivatives of general formula (A) for their interaction with the catalytic domain of tumor-associated isozyme IX, recently cloned and purified by the inventors [33, 43, 114, 115, 117], as well as the cytosolic, physiologically relevant isozymes CA I, II and the membrane-anchored isozyme CA IV [88, 96].

The inhibition of the tumor-associated transmembrane carbonic anhydrase IX (CA IX) isozyme has been investigated with a series of positively-charged, pyridinium derivatives of sulfanilamide, homosulfanilamide and 4-aminoethyl-benzenesulfonamide. Inhibition data for the physiologically relevant isozymes I and II (cytosolic forms) and IV (membrane-bound) were also provided for comparison. This is the first report of inhibitors that may selectively target CA IX, due to their membrane-impermeability and high affinity for this clinically relevant isozyme.

CA Inhibition

Data of Table 2 clearly show that most of the compounds 27-70 act as efficient CA IX inhibitors, and that their affinity for this isozyme differs considerably as compared to affinities for the cytosolic isozymes CA I and II, and the other membrane-associated isozyme investigated, CA IV.

In a series of substituted-pyridinium derived sulfanilamides, homosulfanilamides and p-aminoethylbenzenesulfonamides, a large number of effective hCA IX inhibitors were detected. Some low nanomolar CA IX inhibitors were reported for the first time. Since these compounds are membrane-impermeant due to their salt-like character, and as hCA IX is present on the extracellular side of many tumors with poor clinical prognosis, compounds of this type target specifically this tumor-associate CA isozyme without affecting the cytosolic CAs known to play important physiological functions. Thus, compounds of this type may constitute the basis of new anticancer therapies based on CA inhibitors.

TABLE 2

Inhibition of isozymes hCA I, hCA II, bCA IV and hCA IX with the pyridinium salts 27-70.

A

| Compound | $R^2$ | $R^3$ | $R^4$ | $R^6$ | hCA I[a] (µM) | hCA II[a] (nM) | bCA IV[b] (nM) | hCA IX[c] (nM) |
|---|---|---|---|---|---|---|---|---|
| 27 | Me | H | Me | Me | 10 | 150 | 290 | 165 |
| 28 | Me | H | Ph | Me | 7 | 60 | 211 | 48 |
| 29 | Et | H | Ph | Et | 6 | 60 | 182 | 43 |
| 30 | n-Pr | H | Ph | n-Pr | 10 | 120 | 194 | 178 |
| 31 | i-Pr | H | Ph | i-Pr | 5 | 50 | 90 | 160 |
| 32 | Me | H | Ph | Ph | 40 | 210 | 852 | 280 |
| 33 | Et | H | Ph | Ph | 43 | 400 | 1300 | 450 |
| 34 | n-Pr | H | Ph | Ph | 140 | 580 | 1483 | >500 |
| 35 | i-Pr | H | Ph | Ph | 125 | 440 | 2102 | >500 |
| 36 | n-Bu | H | Ph | Ph | 305 | 620 | 2155 | >500 |
| 37 | Ph | H | Ph | Ph | 290 | 510 | 2500 | >500 |
| 38 | Me | Me | Me | Me | 5 | 40 | 61 | 72 |
| 39 | Me | H | Me | Me | 7 | 50 | 92 | 38 |
| 40 | i-Pr | H | Me | Me | 6 | 50 | 80 | 42 |
| 41 | i-Pr | H | Me | i-Pr | 11 | 80 | 144 | 54 |
| 42 | Me | H | Ph | Me | 4 | 20 | 70 | 26 |
| 43 | Et | H | Ph | Et | 2 | 21 | 52 | 29 |
| 44 | n-Pr | H | Ph | n-Pr | 24 | 90 | 163 | 230 |
| 45 | i-Pr | H | Ph | i-Pr | 12 | 61 | 101 | 100 |
| 46 | Me | H | Ph | Ph | 32 | 121 | 161 | 64 |
| 47 | Et | H | Ph | Ph | 42 | 314 | 983 | 79 |
| 48 | n-Pr | H | Ph | Ph | 130 | 390 | 1260 | 85 |
| 49 | i-Pr | H | Ph | Ph | 112 | 370 | 1214 | 80 |
| 50 | n-Bu | H | Ph | Ph | 300 | 595 | 2104 | 135 |
| 51 | t-Bu | H | Ph | Ph | 110 | 321 | 1070 | >500 |
| 52 | Ph | H | Ph | Ph | 280 | 472 | 1956 | 120 |
| 53 | Ph | H | H | Ph | 280 | 493 | 1954 | 106 |
| 54 | Me | Me | Me | Me | 3 | 30 | 51 | 35 |
| 55 | Me | H | Me | Me | 4 | 21 | 60 | 14 |
| 56 | i-Pr | H | Me | Me | 2 | 15 | 32 | 31 |
| 57 | i-Pr | H | Me | i-Pr | 3 | 20 | 70 | 49 |
| 58 | Me | H | Ph | Me | 1 | 8 | 20 | 6 |
| 59 | Et | H | Ph | Et | 1 | 9 | 21 | 8 |
| 60 | n-Pr | H | Ph | n-Pr | 7 | 42 | 82 | 205 |
| 61 | i-Pr | H | Ph | i-Pr | 6 | 21 | 70 | 89 |
| 62 | Me | H | Ph | Ph | 18 | 103 | 144 | 37 |
| 63 | Et | H | Ph | Ph | 40 | 220 | 761 | 70 |
| 64 | n-Pr | H | Ph | Ph | 112 | 270 | 1055 | 84 |
| 65 | i-Pr | H | Ph | Ph | 94 | 350 | 864 | 78 |
| 66 | n-Bu | H | Ph | Ph | 290 | 544 | 2008 | 120 |
| 67 | t-Bu | H | Ph | Ph | 92 | 275 | 1000 | >500 |
| 68 | Ph | H | Ph | Ph | 270 | 419 | 1830 | 95 |
| 69 | Ph | H | H | Ph | 265 | 420 | 1905 | 81 |
| 70 | Me | Me | Me | Me | 2 | 10 | 21 | 8 |
| acetazolamide | | | | | 0.25 | 12 | 70 | 25 |
| methazolamide | | | | | 0.05 | 14 | 36 | 27 |
| dichlorophenamide | | | | | 1.2 | 38 | 380 | 50 |
| indisulam | | | | | 0.03 | 15 | 65 | 24 |

[a]Human (cloned) isozymes;
[b]From bovine lung microsomes;
[c]Catalytic domain of the human, cloned isozyme.
*errors in the range of ±10% of the reported value, from three different determinations.
For compounds 27-38; n = 0; 39-54: n = 1; 55-70: n = 2

EXAMPLE 3

Design of Selective, Membrane-impermeant Heterocyclic Sulphonamide Inhibitors Targeting the Human Tumor-associated Isozyme IX A series of positively-charged sulfonamides were obtained by reaction of aminobenzolamide (5-(4-aminobenzenesulfonylamino)-1,3,4-thiadiazole-2-sulfonamide) with tri-/tetra-substituted pyrilium salts possessing alkyl-, aryl- or combinations of alkyl and aryl groups at the pyridinium ring. These new compounds are membrane-impermeant due to their salt-like character and were assayed for the inhibition of four physiologically relevant carbonic anhydrase (CA, EC 4.2.1.1) isozymes, the cytosolic hCA I and II, the membrane-anchored bCA IV and the membrane-bound, tumor associated isozyme hCA IX. The high affinity of these new derivatives for the tumor-associated isozyme CA IX and their membrane impermeability, make this type of CA inhibitors interesting candidates for the selective inhibition of only the tumor associated isozyme and not the cytosolic ones, for which they also show high potency.

Results

CA inhibition. Inhibition data against isozymes I, II, IV and IX with compounds 71-91 reported here are shown in Table 3.

TABLE 3

Inhibition of isozymes hCA I, hCA II, bCA IV and hCA IX with the pyridinium salts 71-91.

B

| | $R^1$ | $R^2$ | $R^3$ | $R^4$ | $R^5$ | hCA $I^a$ | hCA $II^a$ | bCA $IV^b$ | hCA $IX^c$ |
|---|---|---|---|---|---|---|---|---|---|
| 71 | Me | H | Me | H | Me | 4 | 0.26 | 2.1 | 3 |
| 72 | i-Pr | H | Me | H | Me | 4 | 0.39 | 3.0 | 5 |
| 73 | i-Pr | H | Me | H | i-Pr | 7 | 1.54 | 4.7 | 16 |
| 74 | t-Bu | H | Me | H | t-Bu | 11 | 3.13 | 9.4 | 34 |
| 75 | Me | H | Ph | H | Me | 3 | 0.20 | 2.0 | 6 |
| 76 | Et | H | Ph | H | Et | 4 | 0.21 | 2.3 | 9 |
| 77 | n-Pr | H | Ph | H | n-Pr | 9 | 3.45 | 8.1 | 35 |
| 78 | n-Bu | H | Ph | H | n-Bu | 10 | 4.62 | 10.3 | 40 |
| 79 | i-Pr | H | Ph | H | i-Pr | 5 | 1.61 | 4.1 | 30 |
| 80 | Me | H | Ph | H | Ph | 4 | 1.21 | 3.0 | 24 |
| 81 | Et | H | Ph | H | Ph | 5 | 1.14 | 3.8 | 29 |
| 82 | n-Pr | H | Ph | H | Ph | 8 | 3.90 | 6.0 | 40 |
| 83 | i-Pr | H | Ph | H | Ph | 6 | 3.74 | 4.5 | 32 |
| 84 | n-Bu | H | Ph | H | Ph | 8 | 4.95 | 8.4 | 45 |
| 85 | t-Bu | H | Ph | H | Ph | 12 | 4.11 | 7.0 | 43 |
| 86 | Ph | H | Me | H | Ph | 6 | 4.78 | 5.8 | 12 |
| 87 | Ph | H | Ph | H | Ph | 5 | 5.96 | 5.6 | 12 |
| 88 | Ph | H | H | H | Ph | 5 | 4.93 | 5.4 | 16 |
| 89 | Me | Me | Me | H | Me | 3 | 0.30 | 2.4 | 5 |
| 90 | Me | Me | Ph | H | Me | 3 | 1.24 | 5.2 | 15 |
| 91 | Me | $R^3,R^5 =$ (CH$_2$)$_9$; $R^4$ = Me | | | Me | 3 | 1.37 | 4.6 | 12 |
| aminobenzolamide | | | | | | 6 | 2.04 | 5.1 | 38 |
| acetazolamide | | | | | | 250 | 12 | 70 | 25 |
| methazolamide | | | | | | 50 | 14 | 36 | 27 |
| dichlorophenamide | | | | | | 1200 | 38 | 380 | 50 |
| indisulam | | | | | | 30 | 15 | 65 | 24 |

$^a$Human (cloned) isozymes, esterase assay method [76].
$^b$From bovine lung microsomes, esterase assay method [76].
$^c$Catalytic domain of the human, cloned isozyme, CO$_2$ hydrase assay method [44].
*Errors in the range of ±10% of the reported value, from three different determinations.

Ex vivo penetration through red blood cells. Levels of sulfonamides in red blood cells after incubation of human erythrocytes with millimolar solutions of inhibitor for 30-60 min (both classical as well as positively-charged sulfonamides were used in such experiments) are shown in Table 4 [4, 12, 36, 45, 53, 54, 58, 59, 84, 116, 118].

TABLE 4

Levels of sulfonamide CA inhibitors (μM) in red blood cells at 30 and 60 min, after exposure of 10 mL of blood to solutions of sulfonamide (2 mM sulfonamide in 5 mM Tris buffer, pH 7.4). The concentrations of sulfonamide has been determined by three methods: HPLC; electronic spectroscopy (ES) and the enzymatic method (EI) - see Experimental for details.

| | [sulfonamide], μM* | | | | | |
|---|---|---|---|---|---|---|
| | t = 30 min | | | t = 60 min | | |
| Inhibitor | HPLC$^a$ | ES$^b$ | EI$^c$ | HPLC$^a$ | ES$^b$ | EI$^c$ |
| AAZ | 136 | 139 | 140 | 160 | 167 | 163 |
| MZA | 170 | 169 | 165 | 168 | 168 | 167 |
| Benzolamide | 110 | 108 | 112 | 148 | 146 | 149 |
| Aminobenzolamide | 125 | 127 | 122 | 154 | 156 | 158 |
| 71 | 0.3 | 0.5 | 0.5 | 0.4 | 0.5 | 0.3 |
| 76 | 1.0 | 1.1 | 1.0 | 1.1 | 1.2 | 1.1 |
| 89 | 0.3 | 0.2 | 0.5 | 0.3 | 0.6 | 0.4 |
| 91 | 0.4 | 0.3 | 0.5 | 0.3 | 0.6 | 0.5 |

*Standard error (from 3 determinations) < 5% by: $^a$the HPLC method [36]; $^b$the electronic spectroscopic method [4]; $^c$the enzymatic method [76].

The new compounds reported in the present work were characterized by standard chemical and physical methods (elemental analysis, within ±0.4% of the theoretical values; IR and NMR spectroscopy) that confirmed their structure (see Materials and Methods and Table 5 below for details) and were assayed for the inhibition of isozymes hCA I, hCA II, bCA IV and hCA IX.

TABLE 5

Elemental analysis data for the compounds described in Example 3

| No | Formula | % C | % H | % N |
|----|---------|-----|-----|-----|
| 71 | $C_{16}H_{18}N_5O_4S_3^+ ClO_4^-$ | 35.59/35.32 | 3.36/3.62 | 12.97/12.93 |
| 72 | $C_{18}H_{22}N_5O_4S_3^+ ClO_4^-$ | 38.06/37.95 | 3.90/4.16 | 12.33/12.18 |
| 73 | $C_{20}H_{26}N_5O_4S_3^+ ClO_4^-$ | 40.30/39.99 | 4.40/4.54 | 11.75/11.63 |
| 74 | $C_{22}H_{30}N_5O_4S_3^+ ClO_4^-$ | 42.34/42.56 | 4.84/4.76 | 11.22/11.03 |
| 75 | $C_{21}H_{20}N_5O_4S_3^+ ClO_4^-$ | 41.89/42.02 | 3.35/3.03 | 11.63/11.48 |
| 76 | $C_{23}H_{24}N_5O_4S_3^+ ClO_4^-$ | 43.84/43.88 | 3.84/3.62 | 11.11/10.95 |
| 77 | $C_{25}H_{28}N_5O_4S_3^+ ClO_4^-$ | 45.62/45.60 | 4.29/4.36 | 10.64/10.50 |
| 78 | $C_{27}H_{32}N_5O_4S_3^+ ClO_4^-$ | 47.26/47.45 | 4.70/4.89 | 10.21/10.14 |
| 79 | $C_{25}H_{28}N_5O_4S_3^+ ClO_4^-$ | 45.62/45.49 | 4.29/4.18 | 10.64/10.61 |
| 80 | $C_{26}H_{22}N_5O_4S_3^+ ClO_4^-$ | 47.02/46.79 | 3.34/3.33 | 10.55/10.23 |
| 81 | $C_{27}H_{24}N_5O_4S_3^+ ClO_4^-$ | 47.82/47.73 | 3.57/3.73 | 10.33/10.40 |
| 82 | $C_{28}H_{26}N_5O_4S_3^+ ClO_4^-$ | 48.59/48.83 | 3.79/3.91 | 10.12/10.24 |
| 83 | $C_{28}H_{26}N_5O_4S_3^+ ClO_4^-$ | 48.59/48.27 | 3.79/3.82 | 10.12/10.05 |
| 84 | $C_{29}H_{28}N_5O_4S_3^+ ClO_4^-$ | 49.32/49.59 | 4.00/4.23 | 9.92/9.67 |
| 85 | $C_{29}H_{28}N_5O_4S_3^+ ClO_4^-$ | 49.32/49.16 | 4.00/3.94 | 9.92/9.71 |
| 86 | $C_{26}H_{22}N_5O_4S_3^+ ClO_4^-$ | 47.02/47.25 | 3.34/3.18 | 10.55/10.46 |
| 87 | $C_{31}H_{24}N_5O_4S_3^+ ClO_4^-$ | 51.72/51.50 | 3.33/3.60 | 9.64/9.67 |
| 88 | $C_{25}H_{20}N_5O_4S_3^+ ClO_4^-$ | 46.19/46.28 | 3.10/2.95 | 10.77/10.67 |
| 89 | $C_{17}H_{20}N_5O_4S_3^+ ClO_4^-$ | 36.86/36.72 | 3.64/3.53 | 12.64/12.45 |
| 90 | $C_{22}H_{22}N_5O_4S_3^+ ClO_4^-$ | 42.89/42.70 | 3.60/3.84 | 11.37/11.15 |
| 91 | $C_{24}H_{32}N_5O_4S_3^+ ClO_4^-$ | 44.34/44.57 | 4.96/4.99 | 10.77/10.51 |

Conclusions

We report here a general approach for the preparation of positively-charged, membrane-impermeant sulfonamide CA inhibitors with high affinity for the cytosolic isozymes CA I and CA II, as well as for the membrane-bound ones CA IV and CA IX. They were obtained by attaching substituted-pyridinium moieties to aminobenzolamide, a very potent CA inhibitor itself. Ex vivo studies showed the new class of inhibitors reported here to discriminate for the membrane-bound versus the cytosolic isozymes. Correlated with the low nanomolar affinity of some of these compounds for the tumor-associated isozyme CA IX, this report constitutes the basis of selectively inhibiting only the target, tumor-associated CA IX in vivo, whereas the cytosolic isozymes would remain unaffected.

Characterization of Compounds 71-91 (For preparation, see Materials and Methods Section)

1-N-[5-Sulfamoyl-1,3,4-thiadiazol-2-yl-(aminosulfonyl-4-phenyl)]-2,4,6-trimethyl-pyridinium perchlorate 71: white crystals, mp>300° C.; IR (KBr), cm$^{-1}$ (bands in italics are due to the anion): 595, 625, 664, 787, 803, 884, 915, 1100, 1150, 1190, 1200, 1285, 1360, 1495, 1604, 3065; $^1$H-NMR (D$_2$O), δ, ppm: 3.08 (s, 6H, 2,6-Me$_2$); 3.11 (s, 3H, 4-Me), 7.30-8.06 (m, AA'BB',4H, ArH from phenylene); 9.05 (s,2H, ArH, 3,5-H from pyridinium); in this solvent the sulfonamido protons are not seen, being in fast exchange with the solvent. Anal $C_{16}H_{18}N_5O_4S_3^+ ClO_4^-$ (C, H, N).

1-N-[5-Sulfamoyl-1,3,4-thiadiazol-2-yl-(aminosulfonyl-4-phenyl)]-2-iso-propyl-4,6-dimethylpyridinium perchlorate 72, colorless crystals, mp 29o-1° C.; IR (KBr), cm$^{-1}$: 625, 680, 720, 1100, 1165, 1330, 1640, 3020, 3235; $^1$H-NMR (TFA), δ, ppm: 1.50 (d, 6H, 2Me from i-Pr); 2.80 (s, 3H, 6-Me); 2.90 (s, 3H, 4-Me); 3.49 (heptet, 1H, CH from i-Pr); 7.25-8.43 (m, AA'BB', 4H, ArH from 1,4-phenylene); 7.98 (s, 2H, ArH, 3,5-H from pyridinium). Anal $C_{18}H_{22}N_5O_4S_3^+ ClO_4^-$ (C, H, N).

1-N-[5-Sulfamoyl-1,3,4-thiadiazol-2-yl-(aminosulfonyl-4-phenyl)]-2,6-di-iso-propyl-4-methylpyridinium perchlorate 73, tan crystals, mp 278-9° C.; IR (KBr), cm$^{-1}$: 625, 685, 820, 1100, 1165, 1340, 1635, 3030, 3250; $^1$H-NMR (TFA), δ, ppm: 1.51 (d, 12H, 4Me from 2 i-Pr); 2.83 (s, 3H, 4-Me); 3.42 (heptet, 2H, 2CH from 2 i-Pr); 7.31-8.51 (m, AA'BB', 4H, ArH from 1,4-phenylene); 8.05 (s, 2H, ArH, 3,5-H from pyridinium). Anal $C_{20}H_{26}N_5O_4S_3^+ ClO_4^-$ (C, H, N).

1-N-[5-Sulfamoyl-1,3,4-thiadiazol-2-yl-(aminosulfonyl-4-phenyl)]-2,6-dimethyl-4-phenylpyridinium perchlorate 75, white crystals, mp>300° C.; IR (KBr), cm$^{-1}$: 625, 690, 770, 1100, 1170, 1330, 1635, 3030, 3260, 3330; $^1$H-NMR (TFA), δ, ppm: 2.62 (s, 6H, 2,6-(Me)$_2$); 8.10-9.12 (m, 11H, ArH from 1,4-phenylene, pyridinium and 4-Ph). Anal $C_{21}H_{20}N_5O_4S_3^+ ClO_4^-$ (C, H, N).

1-N-[5-Sulfamoyl-1,3,4-thiadiazol-2-yl-(aminosulfonyl-4-phenyl)]-2,6-diethyl-4-phenylpyridinium perchlorate 76, tan crystals, mp 267-8° C.; IR (KBr), cm$^{-1}$: 625, 695, 765, 1100, 1180, 1340, 1630, 3040, 3270, 3360; $^1$H-NMR (TFA), δ, ppm: 1.43 (t, 6H, 2 Me from ethyl); 2.82 (q, 4H, 2 CH$_2$ from Et); 7.68-8.87 (m, 11H, ArH from 1,4-phenylene, pyridinium and 4-Ph). Anal $C_{23}H_{24}N_5O_4S_3^+ ClO_4^-$ (C, H, N).

1-N-[5-Sulfamoyl-1,3,4-thiadiazol-2-yl-(aminosulfonyl-4-phenyl)]-2,6-di-n-propyl-4-phenylpyridinium perchlorate 77, colorless crystals, mp 235-7° C.; IR (KBr), cm$^{-1}$: 625, 695, 770, 1100, 1180, 1340, 1630, 3050, 3220, 3315; $^1$H-NMR (TFA), δ, ppm: 1.06 (t, 6H, 2 Me from propyl); 1.73 (sextet, 4H, 2CH$_2$ (β) from n-Pr); 2.84 (t, 4H, 2 CH$_2$ (α) from n-Pr); 7.55-8.71 (m, 11H, ArH from 1,4-phenylene, pyridinium and 4-Ph). Anal $C_{25}H_{28}N_5O_4S_3^+ ClO_4^-$ (C, H, N).

1-N-[5-Sulfamoyl-1,3,4-thiadiazol-2-yl-(aminosulfonyl-4-phenyl)]-2,6-di-isopropyl-4-phenylpyridinium perchlorate 79, white crystals, mp 278-9° C.; IR (KBr), cm$^{-1}$: 625, 690, 765, 1100, 1180, 1340, 1625, 3040, 3270, 3315; $^1$H-NMR (TFA), δ, ppm: 1.45 (d, 12H, 4 Me from i-Pr); 2.95 (heptet, 2H, 2 CH from i-Pr); 7.92-8.97 (m, 11H, ArH from 1,4-phenylene, pyridinium and 4-Ph). Anal $C_{25}H_{28}N_5O_4S_3^+ ClO_4^-$ (C, H, N).

1-N-[5-Sulfamoyl-1,3,4-thiadiazol-2-yl-(aminosulfonyl-4-phenyl)]-2-methyl-4,6-diphenylpyridinium perchlorate 80, white crystals, mp 298-99° C.; IR (KBr), cm$^{-1}$: 625, 710, 770, 1100, 1170, 1345, 1625, 3040, 3245, 3350; $^1$H-NMR (TFA), δ, ppm: 2.75 (s, 3H, 2-Me); 7.53-8.70 (m, 16H, ArH from 1,4-phenylene, pyridinium and 4,6-Ph$_2$). Anal $C_{26}H_{22}N_5O_4S_3^+ ClO_4^-$ (C, H, N).

1-N-[5-Sulfamoyl-1,3,4-thiadiazol-2-yl-(aminosulfonyl-4-phenyl)]-2-ethyl-4,6-diphenylpyridinium perchlorate 81, white crystals, mp 254-5° C.; IR (KBr), cm$^{-1}$: 625, 700, 770, 1100, 1180, 1340, 1620, 3040, 3250, 3350; $^1$H-NMR (TFA), δ, ppm: 1.52 (t, 3H, Me from ethyl); 2.97 (q, 2H, CH$_2$); 7.40-8.57 (m, 16H, ArH from 1,4-phenylene and 4,6-Ph$_2$). Anal $C_{27}H_{24}N_5O_4S_3^+ ClO_4^-$ (C, H, N).

1-N-[5-Sulfamoyl-1,3,4-thiadiazol-2-yl-(aminosulfonyl-4-phenyl)]-2-n-propyl-4,6-diphenylpyridinium perchlorate 82, white crystals, mp 214-5° C.; IR (KBr), cm$^{-1}$: 625, 700, 770, 1100, 1180, 1340, 1620, 3030, 3270, 3350; $^1$H-NMR (TFA), δ, ppm: 1.03 (t, 3H, Me from propyl); 1.95 (sextet, 2H, β-CH$_2$ from n-Pr); 2.88 (t, 2H, α-CH$_2$ from n-Pr); 7.39-8.55 (m, 16H, ArH from 1,4-phenylene and 4,6-Ph$_2$). Anal $C_{28}H_{26}N_5O_4S_3^+ ClO_4^-$ (C, H, N).

1-N-[5-Sulfamoyl-1,3,4-thiadiazol-2-yl-(aminosulfonyl-4-phenyl)]-2-iso-propyl-4,6-diphenylpyridinium perchlorate 83, white crystals, mp 186-8° C.; IR (KBr), cm$^{-1}$: 625, 700, 770, 1100, 1170, 1340, 1620, 3040, 3250, 3360; $^1$H-NMR (TFA), δ, ppm: 1.51 (d, 6H, 2 Me from i-propyl); 2.50-3.27 (m, 1H, CH from i-Pr); 7.32-8.54 (m, 16H, ArH from 1,4-phenylene, pyridinium and 4,6-Ph$_2$). Anal $C_{28}H_{26}N_5O_4S_3^+ ClO_4^-$ (C, H, N).

1-N-[5-Sulfamoyl-1,3,4-thiadiazol-2-yl-(aminosulfonyl-4-phenyl)]-2-n-butyl-4,6-diphenylpyridinium perchlorate 84, white crystals, mp 241-3° C.; IR (KBr), cm$^{-1}$: 625, 710, 770, 1100, 1180, 1335, 1625, 3040, 3260, 3345; $^1$H-NMR (TFA), δ, ppm: 0.93 (t, 3H, Me from butyl); 1.12-2.14 (m, 4H, CH$_3$—CH$_2$—CH$_2$—CH$_2$ from n-Bu); 2.96 (t, 2H, α-CH$_2$ from n-Bu); 7.21-8.50 (m, 16H, ArH from 1,4-phenylene, pyridinium and 4,6-Ph$_2$). Anal C$_{29}$H$_{28}$N$_5$O$_4$S$_3$$^+$ ClO$_4$$^-$ (C, H, N).

1-N-[5-Sulfamoyl-1,3,4-thiadiazol-2-yl-(aminosulfonyl-4-phenyl)]-2-tert-butyl-4,6-diphenylpyridinium perchlorate 85, white crystals, mp 203-5° C.; IR (KBr), cm$^{-1}$: 625, 705, 765, 1100, 1160, 1310, 1620, 3060, 3270; $^1$H-NMR (TFA), δ, ppm: 1.91 (s, 9H, t-Bu); 6.80-8.74 (m, 16H, ArH from 1,4-phenylene, 4,6-Ph$_2$ and 3,5-H from pyridinium). Anal C$_{29}$H$_{28}$N$_5$O$_4$S$_3$$^+$ ClO$_4$$^-$ (C, H, N).

1-N-[5-Sulfamoyl-1,3,4-thiadiazol-2-yl-(aminosulfonyl-4-phenyl)]-2,4,6-triphenhyl-pyridinium perchlorate 87: pale yellow crystals, mp>300° C.; IR (KBr),$^{-1}$ (bands in italics are due to the anion): 625, 635, 703, 785, 896, 1100, 1150, 1204, 1355, 1410, 1520, 1600, 3065; $^1$H-NMR (D$_2$O), δ, ppm: 7.50-8.60 (m, 19H, ArH, 3Ph +C$_6$H$_4$); 9.27 (s,2H, ArH, 3,5-H from pyridinium); in this solvent the sulfonamido protons are not seen, being in fast exchange with the solvent. Anal C$_{31}$H$_{24}$N$_5$O$_4$S$_3$$^+$ ClO$_4$$^-$ (C, H, N).

1-N-[5-Sulfamoyl-1,3,4-thiadiazol-2-yl-(aminosulfonyl-4-phenyl)]-2,6-diphenylpyridinium perchlorate 88, yellow crystals, mp 218-20° C.; IR (KBr), cm$^{-1}$: 625, 705, 765, 1100, 1160, 1335, 1615, 3050, 3260; $^1$H-NMR (TFA), δ, ppm: 6.75-8.43 (m, 17H, ArH from 1,4-phenylene, 2,6-Ph$_2$ and 3,4,5-H from pyridinium). Anal C$_{25}$H$_{20}$N$_5$O$_4$S$_3$$^+$ ClO$_4$$^-$ (C, H, N).

1-N-[5-Sulfamoyl-1,3,4-thiadiazol-2-yl-(aminosulfonyl-4-phenyl)]-2,3,4,6-tetramethylpyridinium perchlorate 89, tan crystals, mp>300° C.; IR (KBr), cm$^{-1}$: 625, 800, 1100, 1165, 1330, 1630, 3030, 3305; $^1$H-NMR (TFA), δ, ppm: 2.62 (s, 3H, 4-Me); 2.74 (s, 3H, 3-Me); 2.88 (s, 6H, 2,6-(Me)$_2$); 7.21-8.50 (m, AA'BB', 4H, ArH from 1,4-phenylene); 7.93 (s, 1H, ArH, 5-H from pyridinium). Anal C$_{17}$H$_{20}$N$_5$O$_4$S$_3$$^+$ ClO$_4$$^-$ (C, H, N).

The description of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to explain the principles of the invention and its practical application to enable thereby others skilled in the art to utilize the invention in various embodiments and with various modifications as are suited to the particular use contemplated.

All references cited herein are hereby incorporated by reference.

The invention claimed is:

1. A method that is diagnostic or diagnostic and prognostic for a preneoplastic/neoplastic disease associated with abnormal MN/CA IX expression comprising contacting a mammalian sample with a potent MN/CA IX-specific inhibitor conjugated to a label or a visualizing means, and detecting or detecting and quantifying binding of said potent MN/CA IX-specific inhibitor to MN/CA IX on cells in said sample by detecting or detecting and quantifying said label or said visualizing means on cells in said sample, wherein said detection or said detection and quantitation at a level above that for a control sample is indicative of preneoplastic/neoplastic cells that overexpress MN/CA IX in said sample;

wherein said inhibitor is selected from the group consisting of organic heterocyclic and aromatic sulfonamides, and wherein said inhibitor is determined to be a potent inhibitor of MN/CA IX enzymatic activity in a screening assay comprising determining the inhibition constant $K_I$ of said compound; wherein if said inhibition constant $K_I$ is determined to be less than about 50 nanomolar, said inhibitor is determined be a potent inhibitor of MN/CA IX enzymatic activity; and wherein said potent inhibitor is determined to be an MN/CA IX-specific inhibitor if it is a more potent inhibitor of MN/CA IX enzymatic activity than of the enzymatic activity of each of the carbonic anhydrases in the group consisting of CA I, CA II and CA IV.

2. The method of claim 1 wherein MN/CA IX is detected or detected and quantitated, and the mammal from whom the sample was taken is considered to have a poor prognosis, and decisions on treatment for said mammal are made in view of the level of said MN/CA IX.

3. A method for imaging tumors and/or metastases that express MN/CA IX in a patient comprising the administration of a potent MN/CA IX-specific inhibitor linked to an imaging agent to said patient;

wherein said inhibitor is selected from the group consisting of heterocyclic and aromatic organic sulfonamides, and wherein said inhibitor is determined to be a potent inhibitor of MN/CA IX enzymatic activity in a screening assay comprising determining the inhibition constant $K_I$ of said compound;

wherein if said inhibition constant $K_I$ is determined to be less than about 50 nanomolar, said inhibitor is determined be a potent inhibitor of MN/CA IX enzymatic activity; and wherein said potent inhibitor is determined to be an MN/CA IX-specific inhibitor if it is a more potent inhibitor of MN/CA IX enzymatic activity than of the enzymatic activity of each of the carbonic anhydrases in the group consisting of CA I, CA II and CA IV.

4. A diagnostic/prognostic method for a preneoplastic/neoplastic disease associated with abnormal MN/CA IX expression, comprising detecting or detecting and quantifying MN/CA IX in a vertebrate sample, comprising:

a) contacting said sample with a cell membrane-impermeant, potent specific inhibitor of MN/CA IX conjugated to a label or a visualizing means, and b) detecting or detecting and quantifying binding of said specific inhibitor of MN/CA IX in said sample by detecting or detecting and quantifying said label or said visualizing means on cells in said sample, wherein said detecting or said detecting and quantifying at a level above that for a control sample is indicative of preneoplastic/neoplastic cells that abnormally express MN/CA IX in said sample;

wherein said inhibitor is selected from the group consisting of cell membrane-impermeant heterocyclic and aromatic organic sulfonamides, and wherein said inhibitor is determined to be a potent inhibitor of MN/CA IX enzymatic activity in a screening assay comprising determining the inhibition constant $K_I$ of said inhibitor;

wherein if said inhibition constant $K_I$ is determined to be less than about 50 nanomolar, said inhibitor is determined be a potent inhibitor of MN/CA IX enzymatic activity; and wherein said potent inhibitor is determined to be an MN/CA IX-specific inhibitor if it is a more potent inhibitor of MN/CA IX enzymatic activity than of the enzymatic activity of CA IV.

5. The method of claim 4, wherein said MNICA IX-specific aromatic or heterocyclic sulfonamide is a cell membrane-impermeant pyridinium derivative of an aromatic or heterocyclic sulfonamide.

6. The method of claim 4, wherein said MN/CA IX-specific aromatic or heterocyclic sulfonamide is selected from the group consisting of Compounds 1, 6, 11-14, 16-26, 28, 29, 39, 40, 42, 43, 54-59, 62 and 70.

7. The method of claim 4, wherein said MN/CA IX-specific sulfonamide is selected from the group consisting of Compounds 1, 6, 11-14 and 16-26.

8. The method of claim 4, wherein said label is fluorescein isothiocyanate.

9. The method of claim 4, wherein said method is used as an aid in selection of patient therapy.

10. The method of claim 9, wherein said binding to MN/CA IX is detectable at a level above that for a control sample, and said method is used in the decision to use MN/CA IX-targeted therapy.

11. The method of claim 9, wherein said therapy comprises the use of MN/CA IX-specific inhibitors, conventional anticancer drugs, chemotherapeutic agents, different inhibitors of cancer-related pathways, bioreductive drugs, radiotherapy, MN/CA IX-specific antibodies and MN/CA IX-specific antibody fragments that are biologically active.

12. The method of claim 4, wherein said method is used to monitor the status of a cancer patient.

13. The method of claim 12, wherein said method is used to monitor cancer chemotherapy and tumor reappearance, detect the presence of cancer metastasis, and/or confirm the absence or removal of all tumor tissue following surgery, cancer chemotherapy and/or radiation therapy.

14. A method of imaging a tumor or tumors and/or metastases that express MN/CA IX in a patient, comprising:

a) administering to said patient a cell membrane-impermeant, potent specific inhibitor of MN/CA IX, said inhibitor linked to an imaging agent; and b) detecting the binding of said inhibitor;

wherein said inhibitor is selected from the group consisting of cell membrane-impermeant heterocyclic and aromatic sulfonamides, and wherein said inhibitor is determined to be a potent inhibitor of MN/CA IX enzymatic activity in a screening assay comprising determining the inhibition constant $K_I$ of said inhibitor, wherein if said inhibition constant $K_I$ is determined to be less than about 50 nanomolar, said inhibitor is determined be a potent inhibitor of MN/CA IX enzymatic activity; and wherein said potent inhibitor is determined to be an MN/CA IX-specific inhibitor if it is a more potent inhibitor of MN/CA IX enzymatic activity than of the enzymatic activity of CA IV.

15. The method of claim 14 wherein said specific inhibitor of MN/CA IX is positively-charged, membrane-impermeant aromatic or heterocyclic sulfonamide.

16. The method of claim 15 wherein said membrane-impermeant sulfonamide is a pyridinium derivative of an aromatic or heterocyclic sulfonamide.

17. The method of claim 4, wherein said MN/CA IX-specific sulfonamide is selected from the group consisting of Compounds 28, 29, 39, 40, 42, 43, 54-59, 62 and 70.

18. The method of claim 1, wherein said group consists of Compounds 1, 6, 11-13, 16-19, 22.26, 28, 29, 39, 40, 55, 58, 59, 62 and 70.

19. The method of claim 3, wherein said group consists of Compounds 1, 6, 11-13, 16-19, 22-26, 28, 29, 39, 40, 55, 58, 59, 62 and 70.

* * * * *

UNITED STATES PATENT AND TRADEMARK OFFICE
CERTIFICATE OF CORRECTION

| | | |
|---|---|---|
| PATENT NO. | : 7,550,424 B2 | Page 1 of 1 |
| APPLICATION NO. | : 10/723795 | |
| DATED | : June 23, 2009 | |
| INVENTOR(S) | : Claudiu Supuran et al. | |

It is certified that error appears in the above-identified patent and that said Letters Patent is hereby corrected as shown below:

Column 69, line 2
"CA I1" should read -- CA II --.

Column 70, line 57
"22.26" should read -- 22-26 --.

Signed and Sealed this
Thirty-first Day of May, 2011

David J. Kappos
Director of the United States Patent and Trademark Office

SEQUENCE LISTING

```
<160> NUMBER OF SEQ ID NOS: 9

<210> SEQ ID NO 1
<211> LENGTH: 1522
<212> TYPE: DNA
<213> ORGANISM: Homo sapiens
<220> FEATURE:
<221> NAME/KEY: CDS
<222> LOCATION: (13)..(1389)
<220> FEATURE:
<221> NAME/KEY: mat_peptide
<222> LOCATION: (124)..(1389)

<400> SEQUENCE: 1
acagtcagcc gc atg gct ccc ctg tgc ccc agc ccc tgg ctc cct ctg ttg        51
              Met Ala Pro Leu Cys Pro Ser Pro Trp Leu Pro Leu Leu
                  -35              -30                  -25 atc ccg gcc cct gct cca ggc ctc act gtg caa ctg ctg ctg tca ctg         99
Ile Pro Ala Pro Ala Pro Gly Leu Thr Val Gln Leu Leu Leu Ser Leu
            -20                 -15                 -10 ctg ctt ctg atg cct gtc cat ccc cag agg ttg ccc cgg atg cag gag        147
Leu Leu Leu Met Pro Val His Pro Gln Arg Leu Pro Arg Met Gln Glu
         -5                 -1  1                  5 gat tcc ccc ttg gga gga ggc tct tct ggg gaa gat gac cca ctg ggc        195
Asp Ser Pro Leu Gly Gly Gly Ser Ser Gly Glu Asp Asp Pro Leu Gly
        10                  15                  20 gag gag gat ctg ccc agt gaa gag gat tca ccc aga gag gag gat cca        243
Glu Glu Asp Leu Pro Ser Glu Glu Asp Ser Pro Arg Glu Glu Asp Pro
 25                  30                  35                  40 ccc gga gag gag gat cta cct gga gag gag gat cta cct gga gag gag        291
Pro Gly Glu Glu Asp Leu Pro Gly Glu Glu Asp Leu Pro Gly Glu Glu
                 45                  50                  55 gat cta cct gaa gtt aag cct aaa tca gaa gaa gag ggc tcc ctg aag        339
Asp Leu Pro Glu Val Lys Pro Lys Ser Glu Glu Glu Gly Ser Leu Lys
             60                  65                  70
```

```
tta gag gat cta cct act gtt gag gct cct gga gat cct caa gaa ccc        387
Leu Glu Asp Leu Pro Thr Val Glu Ala Pro Gly Asp Pro Gln Glu Pro
         75                  80                  85 cag aat aat gcc cac agg gac aaa gaa ggg gat gac cag agt cat tgg        435
Gln Asn Asn Ala His Arg Asp Lys Glu Gly Asp Asp Gln Ser His Trp
 90                  95                 100 cgc tat gga ggc gac ccg ccc tgg ccc cgg gtg tcc cca gcc tgc gcg        483
Arg Tyr Gly Gly Asp Pro Pro Trp Pro Arg Val Ser Pro Ala Cys Ala
105                 110                 115                 120 ggc cgc ttc cag tcc ccg gtg gat atc cgc ccc cag ctc gcc gcc ttc        531
Gly Arg Phe Gln Ser Pro Val Asp Ile Arg Pro Gln Leu Ala Ala Phe
                125                 130                 135 tgc ccg gcc ctg cgc ccc ctg gaa ctc ctg ggc ttc cag ctc ccg ccg        579
Cys Pro Ala Leu Arg Pro Leu Glu Leu Leu Gly Phe Gln Leu Pro Pro
                140                 145                 150 ctc cca gaa ctg cgc ctg cgc aac aat ggc cac agt gtg caa ctg acc        627
Leu Pro Glu Leu Arg Leu Arg Asn Asn Gly His Ser Val Gln Leu Thr
                155                 160                 165 ctg cct cct ggg cta gag atg gct ctg ggt ccc ggg cgg gag tac cgg        675
Leu Pro Pro Gly Leu Glu Met Ala Leu Gly Pro Gly Arg Glu Tyr Arg
170                 175                 180 gct ctg cag ctg cat ctg cac tgg ggg gct gca ggt cgt ccg ggc tcg        723
Ala Leu Gln Leu His Leu His Trp Gly Ala Ala Gly Arg Pro Gly Ser
185                 190                 195                 200 gag cac act gtg gaa ggc cac cgt ttc cct gcc gag atc cac gtg gtt        771
Glu His Thr Val Glu Gly His Arg Phe Pro Ala Glu Ile His Val Val
                205                 210                 215 cac ctc agc acc gcc ttt gcc aga gtt gac gag gcc ttg ggg cgc ccg        819
His Leu Ser Thr Ala Phe Ala Arg Val Asp Glu Ala Leu Gly Arg Pro
                220                 225                 230 gga ggc ctg gcc gtg ttg gcc gcc ttt ctg gag gag ggc ccg gaa gaa        867
Gly Gly Leu Ala Val Leu Ala Ala Phe Leu Glu Glu Gly Pro Glu Glu
                235                 240                 245 aac agt gcc tat gag cag ttg ctg tct cgc ttg gaa gaa atc gct gag        915
Asn Ser Ala Tyr Glu Gln Leu Leu Ser Arg Leu Glu Glu Ile Ala Glu
250                 255                 260 gaa ggc tca gag act cag gtc cca gga ctg gac ata tct gca ctc ctg        963
Glu Gly Ser Glu Thr Gln Val Pro Gly Leu Asp Ile Ser Ala Leu Leu
265                 270                 275                 280 ccc tct gac ttc agc cgc tac ttc caa tat gag ggg tct ctg act aca        1011
Pro Ser Asp Phe Ser Arg Tyr Phe Gln Tyr Glu Gly Ser Leu Thr Thr
                285                 290                 295 ccg ccc tgt gcc cag ggt gtc atc tgg act gtg ttt aac cag aca gtg        1059
Pro Pro Cys Ala Gln Gly Val Ile Trp Thr Val Phe Asn Gln Thr Val
                300                 305                 310 atg ctg agt gct aag cag ctc cac acc ctc tct gac acc ctg tgg gga        1107
Met Leu Ser Ala Lys Gln Leu His Thr Leu Ser Asp Thr Leu Trp Gly
                315                 320                 325 cct ggt gac tct cgg cta cag ctg aac ttc cga gcg acg cag cct ttg        1155
Pro Gly Asp Ser Arg Leu Gln Leu Asn Phe Arg Ala Thr Gln Pro Leu
330                 335                 340 aat ggg cga gtg att gag gcc tcc ttc cct gct gga gtg gac agc agt        1203
Asn Gly Arg Val Ile Glu Ala Ser Phe Pro Ala Gly Val Asp Ser Ser
345                 350                 355                 360 cct cgg gct gct gag cca gtc cag ctg aat tcc tgc ctg gct gct ggt        1251
Pro Arg Ala Ala Glu Pro Val Gln Leu Asn Ser Cys Leu Ala Ala Gly
                365                 370                 375 gac atc cta gcc ctg gtt ttt ggc ctc ctt ttt gct gtc acc agc gtc        1299
Asp Ile Leu Ala Leu Val Phe Gly Leu Leu Phe Ala Val Thr Ser Val
```

-continued

```
           380              385              390
gcg ttc ctt gtg cag atg aga agg cag cac aga agg gga acc aaa ggg      1347
Ala Phe Leu Val Gln Met Arg Arg Gln His Arg Arg Gly Thr Lys Gly
        395              400              405 ggt gtg agc tac cgc cca gca gag gta gcc gag act gga gcc              1389
Gly Val Ser Tyr Arg Pro Ala Glu Val Ala Glu Thr Gly Ala
    410              415              420 tagaggctgg atcttggaga atgtgagaag ccagccagag gcatctgagg gggagccggt    1449
aactgtcctg tcctgctcat tatgccactt ccttttaact gccaagaaat tttttaaaat    1509
aaatatttat aat                                                       1522

<210> SEQ ID NO 2
<211> LENGTH: 459
<212> TYPE: PRT
<213> ORGANISM: Homo sapiens

<400> SEQUENCE: 2

Met Ala Pro Leu Cys Pro Ser Pro Trp Leu Pro Leu Leu Ile Pro Ala
        -35              -30              -25

Pro Ala Pro Gly Leu Thr Val Gln Leu Leu Ser Leu Leu Leu Leu
    -20              -15              -10

Met Pro Val His Pro Gln Arg Leu Pro Arg Met Gln Glu Asp Ser Pro
-5           -1  1               5                       10

Leu Gly Gly Gly Ser Ser Gly Glu Asp Asp Pro Leu Gly Glu Glu Asp
            15              20              25

Leu Pro Ser Glu Glu Asp Ser Pro Arg Glu Glu Asp Pro Pro Gly Glu
        30              35              40

Glu Asp Leu Pro Gly Glu Glu Asp Leu Pro Gly Glu Glu Asp Leu Pro
    45              50              55

Glu Val Lys Pro Lys Ser Glu Glu Gly Ser Leu Lys Leu Glu Asp
60              65              70              75

Leu Pro Thr Val Glu Ala Pro Gly Asp Pro Gln Glu Pro Gln Asn Asn
            80              85              90

Ala His Arg Asp Lys Glu Gly Asp Asp Gln Ser His Trp Arg Tyr Gly
        95              100             105

Gly Asp Pro Pro Trp Pro Arg Val Ser Pro Ala Cys Ala Gly Arg Phe
    110             115             120

Gln Ser Pro Val Asp Ile Arg Pro Gln Leu Ala Ala Phe Cys Pro Ala
    125             130             135

Leu Arg Pro Leu Glu Leu Leu Gly Phe Gln Leu Pro Pro Leu Pro Glu
140             145             150             155

Leu Arg Leu Arg Asn Asn Gly His Ser Val Gln Leu Thr Leu Pro Pro
            160             165             170

Gly Leu Glu Met Ala Leu Gly Pro Gly Arg Glu Tyr Arg Ala Leu Gln
        175             180             185

Leu His Leu His Trp Gly Ala Ala Gly Arg Pro Gly Ser Glu His Thr
    190             195             200

Val Glu Gly His Arg Phe Pro Ala Glu Ile His Val Val His Leu Ser
    205             210             215

Thr Ala Phe Ala Arg Val Asp Glu Ala Leu Gly Arg Pro Gly Gly Leu
220             225             230             235

Ala Val Leu Ala Ala Phe Leu Glu Glu Gly Pro Glu Glu Asn Ser Ala
            240             245             250

Tyr Glu Gln Leu Leu Ser Arg Leu Glu Glu Ile Ala Glu Glu Gly Ser
```

-continued

```
                            255                 260                 265
Glu Thr Gln Val Pro Gly Leu Asp Ile Ser Ala Leu Leu Pro Ser Asp
            270                 275                 280

Phe Ser Arg Tyr Phe Gln Tyr Glu Gly Ser Leu Thr Thr Pro Pro Cys
    285                 290                 295

Ala Gln Gly Val Ile Trp Thr Val Phe Asn Gln Thr Val Met Leu Ser
300                 305                 310                 315

Ala Lys Gln Leu His Thr Leu Ser Asp Thr Leu Trp Gly Pro Gly Asp
                320                 325                 330

Ser Arg Leu Gln Leu Asn Phe Arg Ala Thr Gln Pro Leu Asn Gly Arg
            335                 340                 345

Val Ile Glu Ala Ser Phe Pro Ala Gly Val Asp Ser Ser Pro Arg Ala
        350                 355                 360

Ala Glu Pro Val Gln Leu Asn Ser Cys Leu Ala Ala Gly Asp Ile Leu
    365                 370                 375

Ala Leu Val Phe Gly Leu Leu Phe Ala Val Thr Ser Val Ala Phe Leu
380                 385                 390                 395

Val Gln Met Arg Arg Gln His Arg Arg Gly Thr Lys Gly Gly Val Ser
                400                 405                 410

Tyr Arg Pro Ala Glu Val Ala Glu Thr Gly Ala
            415                 420
```

<210> SEQ ID NO 3
<211> LENGTH: 10898
<212> TYPE: DNA
<213> ORGANISM: Homo sapiens
<220> FEATURE:
<221> NAME/KEY: gene
<222> LOCATION: (1)..(10898)
<220> FEATURE:
<221> NAME/KEY: misc_feature
<222> LOCATION: (1974)..(1974)
<223> OTHER INFORMATION: n is a, c, g, or t

<400> SEQUENCE: 3

```
ggatcctgtt gactcgtgac cttaccccca accctgtgct ctctgaaaca tgagctgtgt    60
ccactcaggg ttaaatggat taagggcggt gcaagatgtg ctttgttaaa cagatgcttg   120
aaggcagcat gctcgttaag agtcatcacc aatccctaat ctcaagtaat cagggacaca   180
aacactgcgg aaggccgcag ggtcctctgc ctaggaaaac cagagacctt tgttcacttg   240
tttatctgac cttccctcca ctattgtcca tgaccctgcc aaatccccct ctgtgagaaa   300
cacccaagaa ttatcaataa aaaataaatt ttaaaaaaaa aatacaaaaa aaaaaaaaaa   360
aaaaaaaaaa gacttacgaa tagttattga taaatgaata gctattggta aagccaagta   420
aatgatcata ttcaaaacca gacggccatc atcacagctc aagtctacct gatttgatct   480
ctttatcatt gtcattcttt ggattcacta gattagtcat catcctcaaa attctccccc   540
aagttctaat tacgttccaa acatttaggg gttacatgaa gcttgaacct actaccttct   600
ttgcttttga gccatgagtt gtaggaatga tgagtttaca ccttacatgc tggggattaa   660
tttaaacttt acctctaagt cagttgggta gcctttggct tattttttgta gctaattttg   720
tagttaatgg atgcactgtg aatcttgcta tgatagtttt cctccacact ttgccactag   780
gggtaggtag gtactcagtt ttcagtaatt gcttacctaa gacccctaagc cctatttctc   840
ttgtactggc ctttatctgt aatatgggca tatttaatac aatataattt ttggagtttt   900
tttgtttgtt tgtttgtttg ttttttttgag acggagtctt gcatctgtca tgcccaggct   960
```

```
ggagtagcag tggtgccatc tcggctcact gcaagctcca cctcccgagt tcacgccatt    1020
ttcctgcctc agcctcccga gtagctggga ctacaggcgc ccgccaccat gcccggctaa    1080 tttttttgtat ttttggtaga cacggggttt caccgtgtta gccagaatgg tctcgatctc   1140
ctgacttcgt gatccacccg cctcggcctc ccaaagttct gggattacag gtgtgagcca    1200
ccgcacctgg ccaattttttt gagtctttta aagtaaaaat atgtcttgta agctggtaac   1260
tatggtacat ttccttttat taatgtgtg ctgacggtca tataggttct tttgagtttg     1320
gcatgcatat gctactttttt gcagtccttt cattacattt ttctctcttc atttgaagag   1380
catgttatat cttttagctt cacttggctt aaaaggttct ctcattagcc taacacagtg    1440
tcattgttgg taccacttgg atcataagtg gaaaacagt caagaaattg cacagtaata     1500
cttgtttgta agagggatga ttcaggtgaa tctgacacta gaaactccc ctacctgagg     1560 tctgagattc ctctgacatt gctgtatata ggcttttcct ttgacagcct gtgactgcgg    1620 actattttc ttaagcaaga tatgctaaag ttttgtgagc ctttttccag agagaggtct     1680
catatctgca tcaagtgaga acatataatg tctgcatgtt tccatatttc aggaatgttt    1740
gcttgtgttt tatgctttta tatagacagg gaaacttgtt cctcagtgac ccaaaagagg    1800
tgggaattgt tattggatat catcattggc ccacgctttc tgaccttgga aacaattaag    1860
ggttcataat ctcaattctg tcagaattgg tacaagaaat agctgctatg tttcttgaca    1920
ttccacttgg taggaaataa gaatgtgaaa ctcttcagtt ggtgtgtgtc cctngttttt    1980
ttgcaatttc cttcttactg tgttaaaaaa agtatgatc ttgctctgag aggtgaggca     2040
ttcttaatca tgatctttaa agatcaataa tataatcctt tcaaggatta tgtctttatt    2100
ataataaaga taatttgtct ttaacagaat caataatata atcccttaaa ggattatatc    2160
tttgctgggc gcagtggctc acacctgtaa tcccagcact ttgggtggcc aaggtggaag    2220
gatcaaattt gcctacttct atattatctt ctaaagcaga attcatctct cttccctcaa    2280
tatgatgata ttgacagggt tgccctcac tcactagatt gtgagctcct gctcagggca    2340
ggtagcgttt tttgttttg ttttgtttt tcttttttga dacagggtct tgctctgtca      2400
cccaggccag agtgcaatgg tacagtctca gctcactgca gcctcaaccg cctcggctca    2460
aaccatcatc ccatttcagc ctcctgagta gctgggacta caggcacatg ccattacacc    2520
tggctaattt ttttgtattt ctagtagaga cagggtttgg ccatgttgcc cgggctggtc    2580
tcgaactcct ggactcaagc aatccaccca cctcagcctc ccaaaatgag gaccgtgtc     2640 ttattcattt ccatgtccct agtccatagc ccagtgctgg acctatggta gtactaaata    2700
aatatttgtt gaatgcaata gtaaatagca tttcagggag caagaactag attaacaaag    2760
gtggtaaaag gtttggagaa aaaaataata gtttaatttg gctagagtat gagggagagt    2820
agtaggagac aagatggaaa ggtctcttgg gcaaggtttt gaaggaagtt ggaagtcaga    2880
agtacacaat gtgcatatcg tggcaggcag tggggagcca atgaaggctt ttgagcagga   2940
gagtaatgtg ttgaaaaata aatataggtt aaacctatca gagcccctct gacacataca    3000
cttgcttttc attcaagctc aagtttgtct cccacatacc cattacttaa ctcaccctcg    3060
ggctccccta gcagcctgcc ctacctcttt acctgcttcc tggtggagtc agggatgtat    3120
acatgagctg ctttccctct cagccagagg acatgggggg cccagctcc cctgcctttc     3180 cccttctgtg cctggagctg ggaagcaggc cagggttagc tgaggctggc tggcaagcag    3240
ctgggtggtg ccaggagag cctgcatagt gccaggtggt gccttgggtt ccaagctagt     3300
ccatggcccc gataaccttc tgcctgtgca cacacctgcc cctcactcca ccccatcct     3360
```

```
agctttggta tgggggagag ggcacagggc cagacaaacc tgtgagactt tggctccatc    3420
tctgcaaaag ggcgctctgt gagtcagcct gctcccctcc aggcttgctc ctcccccacc    3480
cagctctcgt ttccaatgca cgtacagccc gtacacaccg tgtgctggga cacccacag    3540 tcagccgcat ggctcccctg tgccccagcc cctggctccc tctgttgatc ccggcccctg    3600
ctccaggcct cactgtgcaa ctgctgctgt cactgctgct tctggtgcct gtccatcccc    3660
agaggttgcc ccggatgcag gaggattccc ccttgggagg aggctcttct ggggaagatg    3720
acccactggg cgaggaggat ctgcccagtg aagaggattc acccagagag gaggatccac    3780
ccggagagga ggatctacct ggagaggagg atctacctgg agaggaggat ctacctgaag    3840
ttaagcctaa atcagaagaa gagggctccc tgaagttaga ggatctacct actgttgagg    3900
ctcctggaga tcctcaagaa ccccagaata atgcccacag ggacaaagaa ggtaagtggt    3960
catcaatctc caaatccagg ttccaggagg ttcatgactc ccctcccata ccccagccta    4020
ggctctgttc actcagggaa ggaggggaga ctgtactccc cacagaagcc cttccagagg    4080
tcccatacca atatccccat ccccactctc ggaggtagaa agggacagat gtggagagaa    4140
aataaaaagg gtgcaaaagg agagaggtga gctggatgag atgggagaga aggggaggc    4200 tggagaagag aaagggatga gaactgcaga tgagagaaaa aatgtgcaga cagaggaaaa    4260
aaataggtgg agaaggagag tcagagagtt tgaggggaag agaaaaggaa agcttgggag    4320
gtgaagtggg taccagagac aagcaagaag agctggtaga agtcatctca tcttaggcta    4380
caatgaggaa ttgagaccta ggaagaaggg acacagcagg tagagaaacg tggcttcttg    4440
actcccaagc caggaatttg gggaaagggg ttggagacca tacaaggcag agggatgagt    4500
ggggagaaga aagaagggag aaaggaaaga tggtgtactc actcatttgg gactcaggac    4560
tgaagtgccc actcactttt ttttttttt ttttttgagac aaactttcac ttttgttgcc    4620
caggctggag tgcaatggcg cgatctcggc tcactgcaac ctccacctcc cgggttcaag    4680
tgattctcct gcctcagcct ctagccaagt agctgcgatt acaggcatgc gccaccacgc    4740
ccggctaatt tttgtatttt tagtagagac ggggtttcgc catgttggtc aggctggtct    4800
cgaactcctg atctcaggtg atccaaccac cctggcctcc caaagtgctg ggattatagg    4860
cgtgagccac agcgcctggc ctgaagcagc cactcacttt tacagaccct aagcaatga    4920 ttgcaagctg gtaggattgc tgtttggccc acccagctgc ggtgttgagt ttgggtgcgg    4980
tctcctgtgc tttgcacctg gcccgcttaa ggcatttgtt acccgtaatg ctcctgtaag    5040
gcatctgcgt ttgtgacatc gttttggtcg ccaggaaggg attggggctc taagcttgag    5100
cggttcatcc ttttcattta tacagggggat gaccagagtc attggcgcta tggaggtgag    5160
acacccaccc gctgcacaga cccaatctgg gaacccagct ctgtggatct cccctacagc    5220
cgtccctgaa cactggtccc gggcgtccca ccgccgccc accgtccacc ccctcacct    5280 tttctacccg ggttccctaa gttcctgacc taggcgtcag acttcctcac tatactctcc    5340
cacccccagc gacccgccct ggccccgggt gtcccagcc tgcgcgggcc gcttccagtc    5400
cccggtggat atccgccccc agctcgccgc cttctgcccg gccctgcgcc cctggaact    5460 cctgggcttc cagctcccgc cgctcccaga actgcgcctg cgcaacaatg ccacagtgg    5520 tgaggggtc tccccgccga gacttgggga tggggcgggg cgcagggaag ggaaccgtcg    5580
cgcagtgcct gcccggggt tgggctggcc ctaccgggcg gggccggctc acttgcctct    5640
ccctacgcag tgcaactgac cctgcctcct gggctagaga tggctctggg tcccgggcgg    5700
```

```
gagtaccggg ctctgcagct gcatctgcac tgggggctg caggtcgtcc gggctcggag      5760
cacactgtgg aaggccaccg tttccctgcc gaggtgagcg cggactggcc gagaagggc      5820 aaaggagcgg ggcggacggg ggccagagac gtggccctct cctaccctcg tgtccttttc      5880
agatccacgt ggttcacctc agcaccgcct ttgccagagt tgacgaggcc ttggggcgcc      5940
cgggaggcct ggccgtgttg gccgcctttc tggaggtacc agatcctgga cacccctac       6000 tccccgcttt cccatcccat gctcctcccg gactctatcg tggagccaga gaccccatcc      6060
cagcaagctc actcaggccc ctggctgaca aactcattca cgcactgttt gttcatttaa      6120
cacccactgt gaaccaggca ccagccccca acaaggattc tgaagctgta ggtccttgcc      6180
tctaaggagc ccacagccag tggggaggc tgacatgaca gacacatagg aaggacatag       6240
taaagatggt ggtcacagag gagtgacac ttaaagcctt cactggtaga aagaaaagg        6300 aggtgttcat tgcagaggaa acagaatgtg caaagactca gaatatggcc tatttaggga     6360
atggctacat acaccatgat tagaggaggc ccagtaaagg gaagggatgg tgagatgcct     6420
gctaggttca ctcactcact tttatttatt tatttatttt tttgacagtc tctctgtcgc     6480
ccaggctgga gtgcagtggt gtgatcttgg gtcactgcaa cttccgcctc ccgggttcaa     6540
gggattctcc tgcctcagct tcctgagtag ctggggttac aggtgtgtgc caccatgccc     6600
agctaatttt tttttgtatt tttagtagac agggttcac catgttggtc aggctggtct      6660
caaactcctg gcctcaagtg atccgcctga ctcagcctac caaagtgctg attacaagtg     6720
tgagccaccg tgcccagcca cactcactga ttctttaatg ccagccacac agcacaaagt     6780
tcagagaaat gcctccatca tagcatgtca atatgttcat actcttaggt tcatgatgtt     6840
cttaacatta ggttcataag caaaataaga aaaagaata ataataaaa gaagtggcat       6900 gtcaggacct cacctgaaaa gccaaacaca gaatcatgaa ggtgaatgca gaggtgacac     6960
caacacaaag gtgtatatat ggtttcctgt ggggagtatg tacggaggca gcagtgagtg     7020
agactgcaaa cgtcagaagg gcacgggtca ctgagagcct agtatcctag taaagtgggc     7080
tctctccctc tctctccagc ttgtcattga aaccagtcc accagcttg ttggttcgca       7140 cagcaagagt acatagagtt tgaaataata cataggattt taagagggag acactgtctc     7200
taaaaaaaaa aacaacagca acaacaaaaa gcaacaacca ttacaatttt atgttccctc     7260
agcattctca gagctgagga atgggagagg actatgggaa ccccttcat gttccggcct     7320 tcagccatgg ccctggatac atgcactcat ctgtcttaca atgtcattcc cccaggaggg     7380
cccggaagaa aacagtgcct atgagcagtt gctgtctcgc ttggaagaaa tcgctgagga     7440
aggtcagttt gttggtctgg ccactaatct ctgtggccta gttcataaag aatcacccct    7500
tggagcttca ggtctgaggc tggagatggg ctccctccag tgcaggaggg attgaagcat     7560
gagccagcgc tcatcttgat aataaccatg aagctgacag acacagttac ccgcaaacgg     7620
ctgcctacag attgaaaacc aagcaaaaac cgccgggcac ggtggctcac gcctgtaatc     7680
ccagcacttt gggaggccaa ggcaggtgga tcacgaggtc aagagatcaa gaccatcctg     7740
gccaacatgg tgaaacccca tctctactaa aaatacgaaa aaatagccag gcgtggtggc     7800
gggtgcctgt aatcccagct actcgggagg ctgaggcagg agaatggcat gaacccggga     7860
ggcagaagtt gcagtgagcc gagatcgtgc cactgcactc cagcctgggc aacagagcga     7920
gactcttgtc tcaaaaaaaa aaaaaaaaa gaaaaccaag caaaaccaa atgagacaa        7980 aaaaaacaag accaaaaaat ggtgtttgga aattgtcaag gtcaagtctg gagagctaaa     8040 cttttttctga gaactgttta tctttaataa gcatcaaata ttttaacttt gtaaatactt    8100
```

```
ttgttggaaa tcgttctctt cttagtcact cttgggtcat tttaaatctc acttactcta    8160
ctagaccttt taggtttctg ctagactagg tagaactctg cctttgcatt tcttgtgtct    8220
gttttgtata gttatcaata ttcatattta tttacaagtt attcagatca ttttttcttt    8280
tctttttttt tttttttttt tttttacat ctttagtaga gacagggttt caccatattg     8340
gccaggctgc tctcaaactc ctgaccttgt gatccaccag cctcggcctc ccaaagtgct    8400
gggattcatt ttttcttttt aatttgctct gggcttaaac ttgtggccca gcactttatg    8460
atggtacaca gagttaagag tgtagactca gacggtctt cttctttcct tctcttcctt     8520
cctcccttcc ctcccacctt cccttctctc cttccttct ttcttcctct cttgcttcct     8580
caggcctctt ccagttgctc caaagccctg tactttttt tgagttaacg tcttatggga     8640
agggcctgca cttagtgaag aagtggtctc agagttgagt taccttggct tctgggaggt    8700
gaaactgtat ccctatacc tgaagcttta aggggtgca atgtagatga accccaaca       8760
tagatcctct tcacaggctc agagactcag gtcccaggac tggacatatc tgcactcctg    8820
ccctctgact tcagccgcta cttccaatat gaggggtctc tgactacacc gccctgtgcc    8880
cagggtgtca tctggactgt gtttaaccag acagtgatgc tgagtgctaa gcaggtgggc    8940
ctggggtgtg tgtggacaca gtgggtgcgg gggaagagg atgtaagatg agatgagaaa     9000
caggagaaga aagaaatcaa ggctgggctc tgtggcttac gcctataatc ccaccacgtt    9060
gggaggctga ggtgggagaa tggtttgagc ccaggagttc aagacaaggc ggggcaacat    9120
agtgtgaccc catctctacc aaaaaaaccc caacaaaacc aaaatagcc gggcatggtg     9180
gtatgcggcc tagtcccagc tactcaagga ggctgaggtg ggaagatcgc ttgattccag    9240
gagtttgaga ctgcagtgag ctatgatccc accactgcct accatcttta ggatacattt    9300
atttatttat aaaagaaatc aagaggctgg atggggaata caggagctgg agggtggagc    9360
cctgaggtgc tggttgtgag ctggcctggg acccttgttt cctgtcatgc catgaaccca    9420
cccacactgt ccactgacct ccctagctcc acccctctc tgacaccctg tggggacctg     9480
gtgactctcg gctacagctg aacttccgag cgacgcagcc tttgaatggg cgagtgattg    9540
aggcctcctt ccctgctgga gtggacagca gtcctcgggc tgctgagcca ggtacagctt    9600
tgtctggttt ccccccagcc agtagtccct tatcctccca tgtgtgtgcc agtgtctgtc    9660
attggtggtc acagcccgcc tctcacatct cctttttctc tccagtccag ctgaattcct    9720
gcctggctgc tggtgagtct gcccctcctc ttggtcctga tgccaggaga ctcctcagca    9780
ccattcagcc ccagggctgc tcaggaccgc ctctgctccc tctcctttc tgcagaacag     9840
acccccaaccc caatattaga gaggcagatc atggtgggga ttcccccatt gtccccagag   9900
gctaattgat tagaatgaag cttgagaaat ctcccagcat ccctctcgca aaagaatccc    9960
ccccccttt tttaaagata gggtctcact ctgtttgccc caggctgggg tgttgtggca    10020
cgatcatagc tcactgcagc ctcgaactcc taggctcagg caatcctttc accttagctt   10080
ctcaaagcac tgggactgta ggcatgagcc actgtgcctg gccccaaacg gccctttttac 10140
ttggctttta ggaagcaaaa acggtgctta tcttacccct tctcgtgtat ccaccctcat   10200
cccttggctg gcctcttctg gagactgagg cactatgggg ctgcctgaga actcgggca   10260
ggggtggtgg agtgcactga ggcaggtgtt gaggaactct gcagacccct cttccttccc  10320
aaagcagccc tctctgctct ccatcgcagg tgacatccta gccctggttt ttggcctcct  10380
ttttgctgtc accagcgtcg cgttccttgt gcagatgaga aggcagcaca ggtattacac  10440
```

-continued

```
tgacccttc ttcaggcaca agcttccccc acccttgtgg agtcacttca tgcaaagcgc    10500
atgcaaatga gctgctcctg ggccagtttt ctgattagcc tttcctgttg tgtacacaca    10560 gaagggaac caaaggggt gtgagctacc gcccagcaga ggtagccgag actggagcct      10620
agaggctgga tcttggagaa tgtgagaagc cagccagagg catctgaggg ggagccggta    10680
actgtcctgt cctgctcatt atgccacttc cttttaactg ccaagaaatt ttttaaaata    10740
aatatttata ataaaatatg tgttagtcac ctttgttccc caaatcagaa ggaggtattt    10800
gaatttccta ttactgttat tagcaccaat ttagtggtaa tgcatttatt ctattacagt    10860
tcggcctcct tccacacatc actccaatgt gttgctcc                            10898
```

<210> SEQ ID NO 4
<211> LENGTH: 59
<212> TYPE: PRT
<213> ORGANISM: Homo sapiens

<400> SEQUENCE: 4

Ser Ser Gly Glu Asp Asp Pro Leu Gly Glu Glu Asp Leu Pro Ser Glu
1               5                   10                  15

Glu Asp Ser Pro Arg Glu Glu Asp Pro Pro Gly Glu Glu Asp Leu Pro
            20                  25                  30

Gly Glu Glu Asp Leu Pro Gly Glu Glu Asp Leu Pro Glu Val Lys Pro
        35                  40                  45

Lys Ser Glu Glu Glu Gly Ser Leu Lys Leu Glu
    50                  55

<210> SEQ ID NO 5
<211> LENGTH: 257
<212> TYPE: PRT
<213> ORGANISM: Homo sapiens

<400> SEQUENCE: 5

Gly Asp Asp Gln Ser His Trp Arg Tyr Gly Gly Asp Pro Pro Trp Pro
1               5                   10                  15

Arg Val Ser Pro Ala Cys Ala Gly Arg Phe Gln Ser Pro Val Asp Ile
            20                  25                  30

Arg Pro Gln Leu Ala Ala Phe Cys Pro Ala Leu Arg Pro Leu Glu Leu
        35                  40                  45

Leu Gly Phe Gln Leu Pro Pro Leu Pro Glu Leu Arg Leu Arg Asn Asn
    50                  55                  60

Gly His Ser Val Gln Leu Thr Leu Pro Pro Gly Leu Glu Met Ala Leu
65                  70                  75                  80

Gly Pro Gly Arg Glu Tyr Arg Ala Leu Gln Leu His Leu His Trp Gly
                85                  90                  95

Ala Ala Gly Arg Pro Gly Ser Glu His Thr Val Glu Gly His Arg Phe
            100                 105                 110

Pro Ala Glu Ile His Val Val His Leu Ser Thr Ala Phe Ala Arg Val
        115                 120                 125

Asp Glu Ala Leu Gly Arg Pro Gly Gly Leu Ala Val Leu Ala Ala Phe
    130                 135                 140

Leu Glu Glu Gly Pro Glu Glu Asn Ser Ala Tyr Glu Gln Leu Leu Ser
145                 150                 155                 160

Arg Leu Glu Glu Ile Ala Glu Glu Gly Ser Glu Thr Gln Val Pro Gly
                165                 170                 175

Leu Asp Ile Ser Ala Leu Leu Pro Ser Asp Phe Ser Arg Tyr Phe Gln
            180                 185                 190

```
Tyr Glu Gly Ser Leu Thr Thr Pro Pro Cys Ala Gln Gly Val Ile Trp
            195                 200                 205

Thr Val Phe Asn Gln Thr Val Met Leu Ser Ala Lys Gln Leu His Thr
        210                 215                 220

Leu Ser Asp Thr Leu Trp Gly Pro Gly Asp Ser Arg Leu Gln Leu Asn
225                 230                 235                 240

Phe Arg Ala Thr Gln Pro Leu Asn Gly Arg Val Ile Glu Ala Ser Phe
                245                 250                 255

Pro

<210> SEQ ID NO 6
<211> LENGTH: 37
<212> TYPE: PRT
<213> ORGANISM: Homo sapiens

<400> SEQUENCE: 6

Met Ala Pro Leu Cys Pro Ser Pro Trp Leu Pro Leu Leu Ile Pro Ala
1               5                   10                  15

Pro Ala Pro Gly Leu Thr Val Gln Leu Leu Leu Ser Leu Leu Leu Leu
            20                  25                  30

Met Pro Val His Pro
        35

<210> SEQ ID NO 7
<211> LENGTH: 377
<212> TYPE: PRT
<213> ORGANISM: Homo sapiens

<400> SEQUENCE: 7

Gln Arg Leu Pro Arg Met Gln Glu Asp Ser Pro Leu Gly Gly Gly Ser
1               5                   10                  15

Ser Gly Glu Asp Asp Pro Leu Gly Glu Glu Asp Leu Pro Ser Glu Glu
            20                  25                  30

Asp Ser Pro Arg Glu Glu Asp Pro Pro Gly Glu Glu Asp Leu Pro Gly
        35                  40                  45

Glu Glu Asp Leu Pro Gly Glu Glu Asp Leu Pro Glu Val Lys Pro Lys
    50                  55                  60

Ser Glu Glu Glu Gly Ser Leu Lys Leu Glu Asp Leu Pro Thr Val Glu
65                  70                  75                  80

Ala Pro Gly Asp Pro Gln Glu Pro Gln Asn Asn Ala His Arg Asp Lys
                85                  90                  95

Glu Gly Asp Asp Gln Ser His Trp Arg Tyr Gly Gly Asp Pro Pro Trp
            100                 105                 110

Pro Arg Val Ser Pro Ala Cys Ala Gly Arg Phe Gln Ser Pro Val Asp
        115                 120                 125

Ile Arg Pro Gln Leu Ala Ala Phe Cys Pro Ala Leu Arg Pro Leu Glu
    130                 135                 140

Leu Leu Gly Phe Gln Leu Pro Pro Leu Pro Glu Leu Arg Leu Arg Asn
145                 150                 155                 160

Asn Gly His Ser Val Gln Leu Thr Leu Pro Pro Gly Leu Glu Met Ala
                165                 170                 175

Leu Gly Pro Gly Arg Glu Tyr Arg Ala Leu Gln Leu His Leu His Trp
            180                 185                 190

Gly Ala Ala Gly Arg Pro Gly Ser Glu His Thr Val Glu Gly His Arg
        195                 200                 205
```

```
-continued

Phe Pro Ala Glu Ile His Val His Leu Ser Thr Ala Phe Ala Arg
    210             215                 220

Val Asp Glu Ala Leu Gly Arg Pro Gly Gly Leu Ala Val Leu Ala Ala
225                 230                 235                 240

Phe Leu Glu Glu Gly Pro Glu Glu Asn Ser Ala Tyr Glu Gln Leu Leu
                245                 250                 255

Ser Arg Leu Glu Glu Ile Ala Glu Glu Gly Ser Glu Thr Gln Val Pro
                260                 265                 270

Gly Leu Asp Ile Ser Ala Leu Leu Pro Ser Asp Phe Ser Arg Tyr Phe
            275                 280                 285

Gln Tyr Glu Gly Ser Leu Thr Thr Pro Pro Cys Ala Gln Gly Val Ile
        290                 295                 300

Trp Thr Val Phe Asn Gln Thr Val Met Leu Ser Ala Lys Gln Leu His
305                 310                 315                 320

Thr Leu Ser Asp Thr Leu Trp Gly Pro Gly Asp Ser Arg Leu Gln Leu
                325                 330                 335

Asn Phe Arg Ala Thr Gln Pro Leu Asn Gly Arg Val Ile Glu Ala Ser
                340                 345                 350

Phe Pro Ala Gly Val Asp Ser Ser Pro Arg Ala Ala Glu Pro Val Gln
            355                 360                 365

Leu Asn Ser Cys Leu Ala Ala Gly Asp
    370                 375

<210> SEQ ID NO 8
<211> LENGTH: 20
<212> TYPE: PRT
<213> ORGANISM: Homo sapiens

<400> SEQUENCE: 8

Ile Leu Ala Leu Val Phe Gly Leu Leu Phe Ala Val Thr Ser Val Ala
1               5                   10                  15

Phe Leu Val Gln
            20

<210> SEQ ID NO 9
<211> LENGTH: 25
<212> TYPE: PRT
<213> ORGANISM: Homo sapiens

<400> SEQUENCE: 9

Met Arg Arg Gln His Arg Arg Gly Thr Lys Gly Gly Val Ser Tyr Arg
1               5                   10                  15

Pro Ala Glu Val Ala Glu Thr Gly Ala
            20                  25
```